(12) United States Patent
Chan Chun Kong et al.

(10) Patent No.: US 7,960,403 B2
(45) Date of Patent: Jun. 14, 2011

(54) SPIROTROPANE COMPOUNDS AND METHODS FOR THE MODULATION OF CHEMOKINE RECEPTOR ACTIVITY

(75) Inventors: Laval Chan Chun Kong, Kirkland (CA); Christophe Moinet, Laval (CA); Marc Courchesne, Laval (CA); Louis Vaillancourt, Mascouche (CA); Charles Blais, Beaconsfield (CA); Monica Bubenik, Montreal (CA)

(73) Assignee: Virochem Pharma Inc., Quebec (CA)

( * ) Notice: Subject to any disclaimer, the term of this patent is extended or adjusted under 35 U.S.C. 154(b) by 784 days.

(21) Appl. No.: 11/792,581

(22) PCT Filed: Dec. 9, 2005

(86) PCT No.: PCT/CA2005/001878
§ 371 (c)(1),
(2), (4) Date: Feb. 21, 2008

(87) PCT Pub. No.: WO2006/060919
PCT Pub. Date: Jun. 15, 2006

(65) Prior Publication Data
US 2008/0267906 A1    Oct. 30, 2008

Related U.S. Application Data

(60) Provisional application No. 60/634,266, filed on Dec. 9, 2004, provisional application No. 60/693,051, filed on Jun. 23, 2005.

(51) Int. Cl.
*A61K 31/438* (2006.01)
*C07D 471/20* (2006.01)
(52) U.S. Cl. .................... 514/278; 546/18; 546/20
(58) Field of Classification Search .......... 514/278; 546/18, 20
See application file for complete search history.

(56) References Cited

U.S. PATENT DOCUMENTS

| | | | |
|---|---|---|---|
| 5,407,938 | A | 4/1995 | Fisher et al. |
| 5,534,520 | A | 7/1996 | Fisher et al. |
| 5,852,029 | A | 12/1998 | Fisher et al. |

FOREIGN PATENT DOCUMENTS

| | | |
|---|---|---|
| CA | 2310458 | 6/1991 |
| CA | 2 310 458 A1 | 6/1999 |
| WO | WO 95/03303 A2 | 2/1995 |
| WO | WO 01/66546 A1 | 9/2001 |
| WO | WO 02/13824 A1 | 2/2002 |
| WO | WO 2004/041279 A1 | 5/2004 |
| WO | WO 2005/007656 A1 | 1/2005 |
| WO | WO 2005007656 A1 | 1/2005 |
| WO | WO 2005/023809 A1 | 3/2005 |
| WO | WO 2005/023810 A1 | 3/2005 |
| WO | WO 2005023810 A1 | 3/2005 |
| WO | WO 2006/000096 A1 | 1/2006 |
| WO | WO 2006/060918 A1 | 6/2006 |
| WO | WO 2006/060919 A1 | 6/2006 |
| WO | WO 2007/143847 A1 | 12/2007 |

OTHER PUBLICATIONS

International Search Report for International Application No. PCT/CA2005/001878 mailed Mar. 29, 2006.
International Preliminary Report on Patentability for International Application No. PCT/CA2005/001878 issued Jun. 13, 2007.
Dr. Rolf Eberbard Nitz, et al., Arzneimittel-Forschung, pp. 357-364, Jul. 1955.
Por A. Garcia Sacristan, et al., Arch. De. Farmacol y Toxicol, 1977, pp. 57-66.
George W. Smith, et al., Journal of the American Chemical Society, vol. 77, pp. 3541-3543, Jul. 5, 1955.
Abstract of Dr. Rolf Eberbard Nitz, et al., Arzneimittel-Forschung, pp. 357-364, Jul. 1955.
Abstract of Por A. Garcia Sacristan, et al., Arch. De. Farmcol y Toxicol, 1977, pp. 57-66.
International Search Report for International Application No. PCT/CA2007/001062 mailed Sep. 6, 2007.
Supplementary European Search Report for European Application No: 05 81 9431.7—2117/ 1831222 of Sep. 18, 2009.
Written Opinion of the International Searching Authority for International Application No. PCT/CA2005/001877 mailed Mar. 29, 2006.
Extended European Search Report in European Application No. 05 819 950.6—2101 / 1824853 dated Oct. 5, 2010.
International Search Report for International Application No: PCT/CA2005/001877 mailed Mar. 29, 2006.
International Preliminary Report on Patentability for International Application No. PCT/CA2005/001877 issued Jun. 13, 2007.
Fujio, M. et al. "Spiro compounds, process for preparing the same and use thereof as drugs", Abstract of WO2001066546 A1. Publication date: Sep. 13, 2001. Application No: WO2001JP1793A. Filing date: Mar. 7, 2001. (Thomson Innovation Record View).
Bellanto, J. et al. "Raman spectra and hydrogen bonding of azabicyclospirohydantoins", Accession No. 1981:207963, CAPULUS 77699151 (1980).
Bellanto, J. et al. "Hydrogen bonding and IR spectra of N-substituted granatanine- and nortropane-3-spiro-5'-hydantoins", Accession No. 1980:40819, CAPULUS 72402245 (1979).
Castro, V. et al. "Local-anesthetic-antiinflammatory activity of some spiro[hydantoin] derivatives of N-substituted nortropane.", Accession No. 1978:590809, CAPULUS 64192796 (1978).

*Primary Examiner* — Charanjit S Aulakh
(74) *Attorney, Agent, or Firm* — Millen, White, Zelano & Branigan, P.C.

(57) ABSTRACT

Compounds according to formula (I):

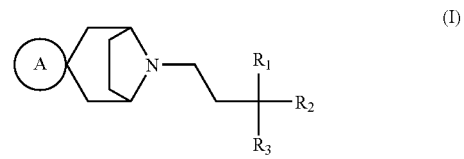

wherein A, $R_1$, $R_2$ and $R_3$ are defined as defined herein, and the pharmaceutically acceptable salts, hydrates and solvates thereof, are useful for the modulation of CCR5 chemokine receptor activity.

38 Claims, No Drawings

SPIROTROPANE COMPOUNDS AND METHODS FOR THE MODULATION OF CHEMOKINE RECEPTOR ACTIVITY

The application claims the benefit of U.S. Ser. No. 60/634,266 filed on Dec. 9, 2004 and U.S. Ser. No. 60/693,051 filed on Jun. 23, 2005 which are herein incorporated by reference.

FIELD OF THE INVENTION

The present invention relates to novel spirotropane compounds and a method of modulating chemokine receptor activity using these compounds. The present invention is also directed to novel spirotropane compounds which are useful in the prevention or treatment of diseases associated with the modulation of CCR5 chemokine receptor activity. The present invention is further directed to a method of blocking cellular entry of HIV in a subject and to compositions using these compounds.

BACKGROUND OF THE INVENTION

Chemokines are chemotactic cytokines that are released by a wide variety of cells to attract macrophages, T cells, eosinophils, basophils and neutrophils to sites of inflammation and they also play a role in the maturation of cells of the immune system. Chemokines play an important role in immune and inflammatory responses in various diseases and disorders, including asthma, rhinitis and allergic diseases, as well as autoimmune pathologies such as rheumatoid arthritis and atherosclerosis. Chemokines are small 70 to 80 amino acid proteins with well-characterized three-dimensional structures, usually stabilized by two disulfide bridges. They are divided into four families on the basis of pattern of conserved cysteine residues. Chemokine receptors have been designated such as, CCR1, CCR2, CC2A, CCR2B, CCR3, CCR4, CCR5, CCR6, CCR7, CCR8, CCR9, CCR10, CXCR1, CXCR2, CXCR3, and CXCR4 and therefore agents which modulate these receptors may be useful in the prevention and treatment of diseases as mentioned above.

One of them, the C—C chemokines family, includes potent chemoattractants of monocytes and lymphocytes such as RANTES (Regulated on Activation, Normal T Expressed and Secreted), eotaxin, MIP-1α and MIP-1β (Macrophage Inflammatory Proteins) and human monocyte chemotactic proteins 1-3 (MCP-1, MCP-2 and MCP-3). More specifically, C—C chemokine receptor 5 (CCR5), a β-chemokine receptor with a seven-transmembrane-protein structure, was found to serve as a coreceptor for non-syncytium-inducing or macrophage-tropic HIV-1 (R5 viruses). It was also established that CCR5 is the principal chemokine receptor required for the entry of HIV into the cell during primary infection. Therefore, interfering with the interaction between the viral receptor CCR5 and HIV can block HIV entry into the cell. It would therefore be useful to provide novel compounds which are modulators of chemokine receptor activity.

SUMMARY OF THE INVENTION

In one aspect, the present invention provides novel compounds represented by formula (I):

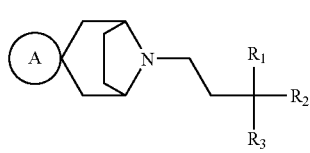

(I)

or pharmaceutically acceptable salts, hydrates or solvates thereof,

Wherein:

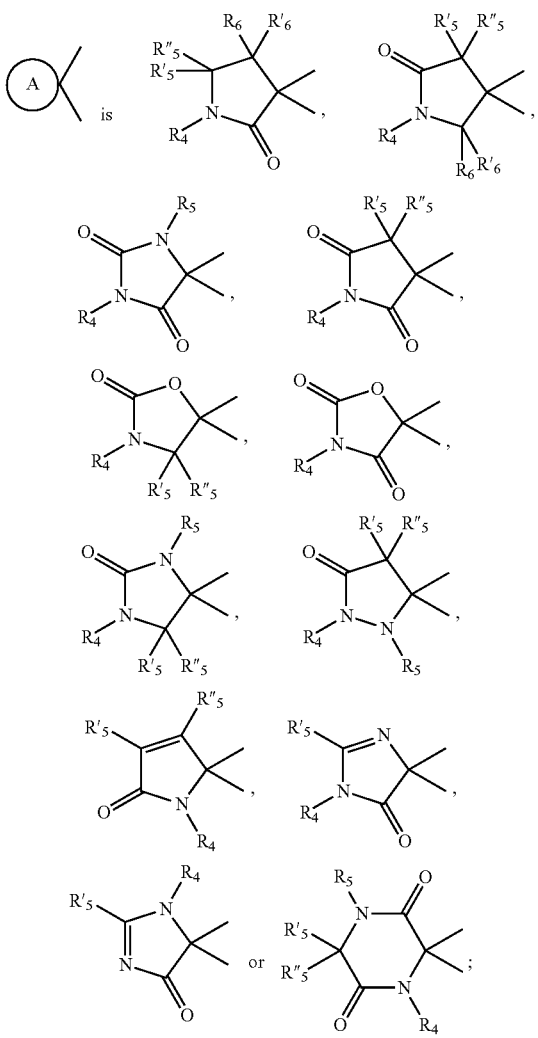

$R_1$ is $NR_7R_9$,

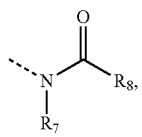

(II)

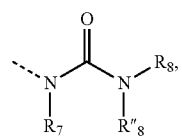

(III)

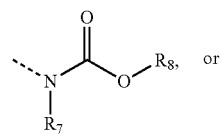

(IV)

or

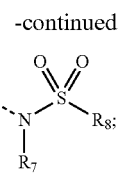

R$_2$ is optionally substituted C$_{1-10}$ alkyl, optionally substituted C$_{2-10}$ alkenyl (e.g. C$_{2-6}$ alkenyl), optionally substituted C$_{2-10}$ alkynyl (e.g. C$_{2-6}$ alkynyl), optionally substituted C$_{6-12}$ aryl or optionally substituted 3 to 10 membered heterocycle;

R$_3$ is chosen from H, optionally substituted C$_{1-10}$ alkyl or optionally substituted C$_{6-12}$ aryl;

R$_4$, R$_5$, R'$_5$, R''$_5$, R$_6$ and R'$_6$ are each, independently, H, optionally substituted C$_{1-10}$ alkyl, optionally substituted C$_{2-10}$ alkenyl (e.g. C$_{2-6}$ alkenyl), optionally substituted C$_{2-10}$ alkynyl (e.g. C$_{2-6}$ alkynyl), optionally substituted C$_{6-12}$ aryl, optionally substituted 3 to 10 membered heterocycle, optionally substituted C$_{7-12}$ aralkyl or optionally substituted heteroaralkyl (e.g., wherein the heteroaryl portion has 3 to 10 members and the alkyl portion has 1 to 6 carbon atoms);

R$_7$ and R''$_8$ are each independently H, optionally substituted C$_{1-10}$ alkyl (e.g. C$_{1-4}$ alkyl), optionally substituted C$_{2-10}$ alkenyl (e.g. C$_{2-4}$ alkenyl), or optionally substituted C$_{2-10}$ alkynyl (e.g. C$_{2-4}$ alkynyl);

R$_8$ is H, optionally substituted C$_{6-10}$ alkyl, optionally substituted C$_{2-10}$ alkenyl, optionally substituted C$_{2-10}$ alkynyl, optionally substituted C$_{6-12}$ aryl, optionally substituted 3 to 10 membered heterocycle, optionally substituted C$_{7-12}$ aralkyl or optionally substituted heteroaralkyl (e.g., wherein the heteroaryl portion has 3 to 10 members and the alkyl portion has 1 to 6 carbon atoms);

R''$_8$ and R$_8$ can be taken together to form an optionally substituted 3 to 10 membered heterocycle; and R$_9$ is H or optionally substituted C$_{1-10}$ alkyl.

In another aspect, there is provided a method of modulating chemokine receptor activity in a subject comprising administering to the subject an effective amount of a compound of formula (I) or composition of the invention.

In still another aspect, there is provided a method for prevention or treatment of certain inflammatory diseases, immunoregulatory diseases, organ transplantation reactions and in the prevention and treatment of infectious diseases such as HIV infections in a subject in need of such treatment comprising administering to the subject a therapeutically effective amount of a compound of formula (I) or composition of the invention.

In still another aspect, there is provided a method for the prevention or treatment of diseases associated with the modulation of CCR5 chemokine receptor activity in a subject in need of such treatment comprising administering to the subject a therapeutically effective amount of a compound of formula (I) or composition of the invention.

In still another aspect, there is provided a method for blocking cellular entry of HIV in a subject comprising administering to the subject in need thereof an effective amount of a compound of formula (I) or composition of the invention to block HIV from cellular entry in said subject.

In still another aspect, there is provided a method for the prevention or treatment of diseases associated with the modulation of chemokine receptor activity in a subject in need of such treatment comprising administering to the subject a pharmaceutical combination comprising at least one compound of formula (I) and at least one further therapeutic agent.

In another aspect, there is provided a pharmaceutical formulation comprising the compound of the invention in combination with a pharmaceutically acceptable carrier or excipient.

In another aspect of the invention is the use of a compound according to formula (I), for the manufacture of a medicament for the prevention or treatment of diseases associated with the modulation of chemokine receptor activity.

DETAILED DESCRIPTION OF THE INVENTION

In one embodiment, compounds of the present invention comprise those wherein the following embodiments are present, either independently or in combination.

In one embodiment, the present invention provides novel compounds represented by formula I:

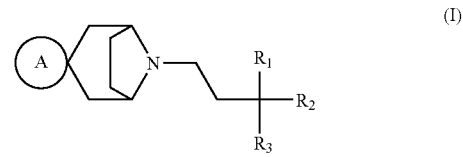

or pharmaceutically acceptable salts, hydrates or solvates thereof wherein A, R$_1$, R$_2$ and R$_3$ are defined above.

In one embodiment, the present invention provides novel compounds represented by formula (Ia):

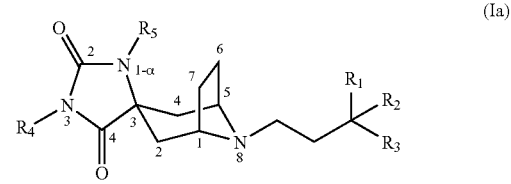

or pharmaceutically acceptable salts, hydrates or solvates thereof wherein R$_1$, R$_2$, R$_3$, R$_4$ and R$_5$ are defined above.

In one embodiment, the present invention provides novel compounds represented by formula (Ib):

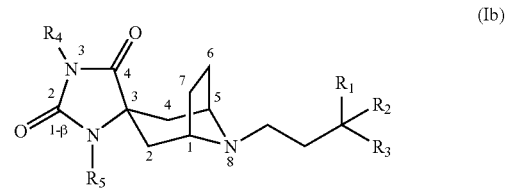

or pharmaceutically acceptable salts, hydrates or solvates thereof wherein R$_1$, R$_2$, R$_3$, R$_4$ and R$_5$ are defined above.

In one embodiment, the present invention provides novel compounds represented by formula (Ic) and (Ic'):

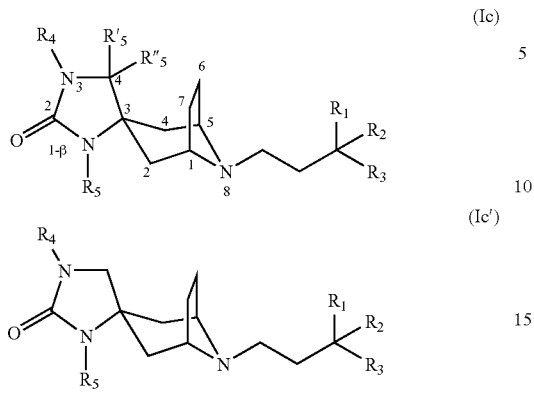

(Ic)

(Ic')

or pharmaceutically acceptable salts, hydrates or solvates thereof wherein $R_1$, $R_2$, $R_3$, $R_4$, $R_5$, $R'_5$ and $R''_5$ are defined above.

In one embodiment, the present invention provides novel compounds represented by formula (Id) and (Id'):

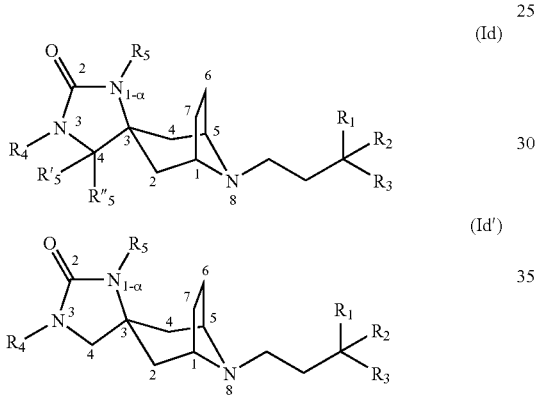

(Id)

(Id')

or pharmaceutically acceptable salts, hydrates or solvates thereof wherein $R_1$, $R_2$, $R_3$, $R_4$, $R_5$, $R'_5$ and $R''_5$ are defined above.

In one embodiment, the compounds of the present invention are in the (S)-enantiomer as represented by formula (I):

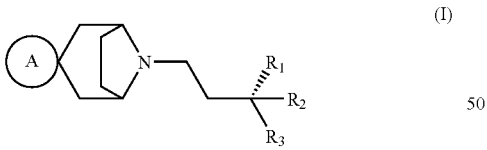

(I)

or pharmaceutically acceptable salts, hydrates or solvates thereof wherein A, $R_1$, $R_2$ and $R_3$ are defined above.

In one embodiment, the compounds of the present invention are in the (R)-enantiomer as represented by formula (I):

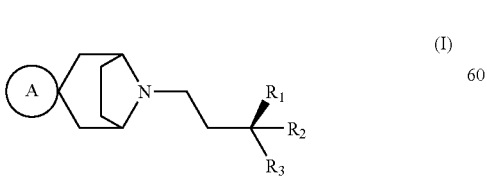

(I)

or pharmaceutically acceptable salts, hydrates or solvates thereof wherein A, $R_1$, $R_2$ and $R_3$ are defined above.

In a further embodiment, $R_1$ is chosen from:

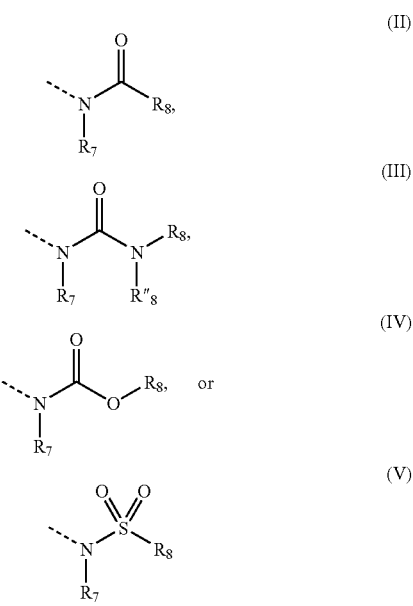

(II)

(III)

(IV) or (V)

In a further embodiment, $R_1$ is:

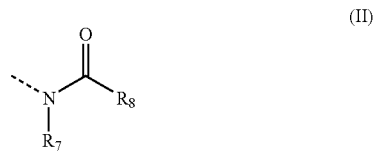

(II)

In further embodiments, $R_1$ is:

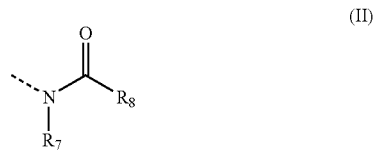

(II)

In a further embodiment, $R_1$ is:

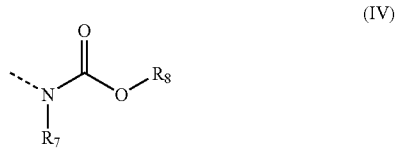

(IV)

In further embodiments, $R_1$ is:

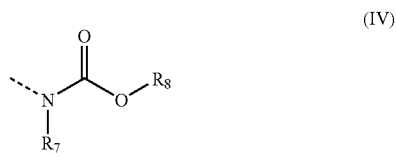

(IV)

In a further embodiment, $R_2$ is chosen from a $C_{6-12}$ aryl, and 3-10 member heterocycle which in each case are optionally substituted.

In a further embodiment, $R_2$ is a $C_{6-12}$ aryl, or a 3-6 member heterocycle which in each case are optionally substituted.

In a further embodiment, $R_2$ is $C_{6-12}$ aryl.

In a further embodiment, $R_2$ is an aryl chosen from phenyl, indenyl, naphthyl and biphenyl which in each case are optionally substituted.

In a further embodiment, $R_2$ is unsubstituted phenyl or phenyl substituted with at least one substituent chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, $NR_{63}R_{64}$, $C(O)OR_{62}$, cyano, azido, amidino and guanido;
  wherein $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, $C_{7-18}$ aralkyl,
  or $R_{65}$ and $R_{66}$ are taken together with the oxygen atoms to form a 5 to 10 member heterocycle,
  or $R_{63}$ and $R_{64}$ are taken together with the nitrogen atom to form a 3 to 10 member heterocycle.

In a further embodiment, $R_2$ is unsubstituted phenyl or phenyl substituted with at least one substituent chosen from halogen, nitro, $CONR_{63}R_{64}$, $C_{1-6}$ alkyl, $C_{2-6}$ alkenyl, $C_{1-6}$ alkyloxy, $C_{2-6}$ alkenyloxy, $C_{2-6}$ alkynyloxy, $C(O)C_{1-6}$ alkyl, $C_{6-12}$ aryl, 3-10 member heterocycle, 4-16 member heteroaralkyl, hydroxyl, $NR_{63}R_{64}$, $C(O)OR_{62}$, cyano, and azido;
  wherein $R_{62}$, $R_{63}$ and $R_{64}$ are each independently chosen from H, $C_{1-12}$ alkyl, $C_{6-12}$ aryl, 3-12 member heterocycle, 4-16 member heteroaralkyl, and $C_{7-18}$ aralkyl,
  or $R_{63}$ and $R_{64}$ are taken together with the nitrogen to form a 3 to 10 member heterocycle.

In a further embodiment, $R_2$ is unsubstituted phenyl or phenyl substituted with at least one substituent chosen from halogen, $C_{1-6}$ alkyl, $NR_{63}R_{64}$, nitro, $CONR_{63}R_{64}$, $C(O)OC_{1-6}$ alkyl, $C_{1-6}$ alkyloxy, $C(O)OR_{62}$, cyano, and azido;
  wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl,
  or $R_{63}$ and $R_{64}$ are taken together with the nitrogen to form a 3 to 10 member heterocycle.

In a further embodiment, $R_2$ is unsubstituted phenyl or phenyl substituted with at least one substituent chosen from a halogen, $C_{1-6}$ alkyl, $C_{1-6}$ alkyloxy, $CF_3$, COOH, $COOC_{1-6}$ alkyl, cyano, $NH_2$, nitro, $NH(C_{1-6}$ alkyl), $N(C_{1-6}$ alkyl)$_2$ and a 3-8 member heterocycle.

$R_2$ is optionally substituted $C_{6-12}$ aryl.
$R_2$ is phenyl;
$R_2$ is phenyl substituted with halogen;
$R_2$ is phenyl substituted with Cl;
$R_2$ is phenyl substituted with F;
$R_2$ is phenyl substituted with at least one halogen.

In a further embodiment, $R_2$ is chosen from thienyl, furanyl, pyridyl, oxazolyl, thiazolyl, pyrrolyl, benzofuranyl, indolyl, benzoxazolyl, benzothienyl, benzothiazolyl and quinolinyl, any of which can be unsubstituted or substituted by at least one substituent chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O) C_{1-6}$ alkyl, $C(O)C_{2-6}$ alkenyl, $C(O)C_{2-6}$ alkynyl, $C(O)C_{6-12}$ aryl, $C(O)$ $C_{7-12}$ aralkyl, 3-10 member heterocycle, 4-16 member heteroaralkyl, hydroxyl, $NR_{63}R_{64}$, $C(O) OR_{62}$, cyano, azido, amidino and guanido;
  wherein $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl,
  or $R_{65}$ and $R_{66}$ are taken together with the oxygen atoms to form a 5 to 10 member heterocycle,
  or $R_{63}$ and $R_{64}$ are taken together with the nitrogen atom to form a 3 to 10 member heterocycle.

In a further embodiment, $R_2$ is chosen from thienyl, furanyl, pyridyl, oxazolyl, thiazolyl, pyrrolyl, benzofuranyl, indolyl, benzoxazolyl, benzothienyl, benzothiazolyl and quinolinyl, any of which can be unsubstituted or substituted by at least one substituent chosen from $C_{1-6}$ alkyl, amino, halogen, nitro, amido, CN, $COOC_{1-6}$ alkyl, $C_{1-6}$ alkyloxy.

In a further embodiment, $R_2$ is chosen from pyridinyl, thiophenyl, benzofuran, thiazole, and pyrazole, any of which can be unsubstituted or substituted with at least one substituent chosen from a halogen, $C_{1-6}$ alkyl, $C_{1-6}$ alkyloxy, $CF_3$, COOH, $COOC_{1-6}$ alkyl, cyano, $NH_2$, nitro, $NH(C_{1-6}$ alkyl), $N(C_{1-6}$ alkyl)$_2$ and a 3-8 member heterocycle.

In a further embodiment, $R_3$ is H or optionally substituted $C_{1-10}$ alkyl.
$R_3$ is $C_{1-6}$ alkyl optionally substituted.
$R_3$ is $C_{3-12}$ cycloalkyl optionally substituted.
$R_3$ is $C_{3-10}$ cycloalkyl optionally substituted.
$R_3$ is $C_{5-7}$ cycloalkyl optionally substituted.
$R_3$ is optionally substituted $C_{6-7}$ cycloalkyl.
$R_3$ is optionally substituted $C_6$ cycloalkyl.

In a further embodiment, $R_3$ is chosen from methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl, any of which unsubstituted or substituted by one or more substituents chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)$ $C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, oxo, oxime, $NR_{63}R_{64}$, $C(O)$ $OR_{62}$, cyano, azido, amidino and guanido;
  wherein $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl,
  or $R_{65}$ and $R_{66}$ are taken together with the oxygen atoms to form a 5 to 10 member heterocycle,
  or $R_{63}$ and $R_{64}$ are taken together with the nitrogen atom to form a 3 to 10 member.

In a further embodiment, $R_3$ is chosen from methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl any of which unsubstituted or substituted by one or more substituents chosen from halogen, nitro, $CONR_{63}R_{64}$, $C_{1-6}$ alkyl, $C_{2-6}$ alkenyl, $C_{1-6}$ alkyloxy, $C_{2-6}$ alkenyloxy, $C_{2-6}$ alkynyloxy, $C(O)C_{1-6}$ alkyl, $C_{6-12}$ aryl, 3-10 member heterocycle, 4-16 member heteroaralkyl, hydroxyl, $NR_{63}R_{64}$, $C(O)OR_{62}$, cyano, and azido;
  wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl,
  or $R_{63}$ and $R_{64}$ are taken together with the nitrogen to form a 3 to 10 member heterocycle.

In a further embodiment, $R_3$ is methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl any of which unsubstituted or substituted by one or two substituents chosen from halogen, $C_{1-6}$ alkyl, $NR_{63}R_{64}$, nitro, $CONR_{63}R_{64}$, $C_{1-6}$ alkyloxy, $C(O)OR_{62}$, cyano, and azido;

wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen to form a 3 to 10 member heterocycle.

In a further embodiment, $R_3$ is methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl any of which unsubstituted or substituted by one or more substituents chosen from a halogen, $C_{1-6}$ alkyl, $C_{1-6}$ alkyloxy, $CF_3$, COOH, $COOC_{1-6}$ alkyl, cyano, $NH_2$, nitro, $NH(C_{1-6}$ alkyl), $N(C_{1-6}$ alkyl)$_2$ and a 3-8 heterocycle.

In a further embodiment, $R_3$ is chosen from methyl, ethyl, vinyl, propyl, propenyl, isopropyl, butyl, isobutyl, pentyl, neopentyl, or tert-butyl.

In one embodiment, $R_3$ is methyl.

In one embodiment, $R_3$ is H.

In one embodiment, $R_4$ or $R_5$ are independently optionally substituted $C_{6-12}$ aryl, optionally substituted 3 to 10 membered heterocycle, optionally substituted $C_{7-12}$ aralkyl or optionally substituted 4-16 member heteroaralkyl.

In a further embodiment, $R_4$ or $R_5$ are independently optionally substituted $C_{6-12}$ aryl.

In a further embodiment, $R_4$ or $R_5$ are independently optionally substituted 3 to 10 membered heterocycle.

In a further embodiment, $R_4$ or $R_5$ are independently optionally substituted $C_{7-12}$ aralkyl.

In a further embodiment, $R_4$ or $R_5$ are independently optionally substituted 4-16 member heteroaralkyl.

In a further embodiment, $R_4$ or $R_5$ are independently $C_{6-12}$ aryl, $C_{7-12}$ aralkyl, 3 to 10 membered heterocycle or 4-16 member heteroaralkyl which are unsubstituted or substituted by one or more substituents chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, oxo, oxime, $NR_{63}R_{64}$, $C(O)OR_{62}$, cyano, azido, amidino and guanido;

wherein $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl, or $R_{65}$ and $R_{66}$ are taken together with the oxygen atoms to form a 5 to 10 member heterocycle, or $R_{63}$ and $R_{64}$ are taken together with the nitrogen atom to form a 3 to 10 member heterocycle.

In a further embodiment, $R_4$ or $R_5$ are independently $C_{6-12}$ aryl, $C_{7-12}$ aralkyl, 3 to 10 membered heterocycle or 4-16 member heteroaralkyl which are unsubstituted or substituted by one or more substituents chosen from halogen, $C_{1-6}$ alkyl, $NR_{63}R_{64}$, nitro, $CONR_{63}R_{64}$, $C_{1-6}$ alkyloxy, $C(O)$ $OR_{62}$, cyano, and azido;

wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen to form a 3 to 10 member heterocycle.

In a further embodiment, $R_4$ or $R_5$ are independently $C_{6-12}$ aryl, $C_{7-12}$ aralkyl, 3 to 10 membered heterocycle or 4-16 member heteroaralkyl which are unsubstituted or substituted by one or more substituents chosen from a halogen, $C_{1-6}$ alkyl, $C_{1-6}$ alkyloxy, $CF_3$, COOH, $COOC_{1-6}$ alkyl, cyano, $NH_2$, nitro, $NH(C_{1-6}$ alkyl), $N(C_{1-6}$alkyl)$_2$ and a 3-8 member heterocycle.

In a further embodiment, $R_4$ or $R_5$ are independently phenyl or benzyl which are unsubstituted or substituted by one or more substituents chosen from halogen, nitro, $CONR_{63}R_{64}$, $C_{1-6}$ alkyl, $C_{2-6}$ alkenyl, $C_{1-6}$ alkyloxy, $C_{2-6}$ alkenyloxy, $C_{2-6}$ alkynyloxy, $C(O)C_{1-6}$ alkyl, $C_{6-12}$ aryl, 3-10 member heterocycle, 4-16 member heteroaralkyl, hydroxyl, $NR_{63}R_{64}$, $C(O)$ $OR_{62}$, cyano, and azido;

wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen to form a 3 to 10 member heterocycle.

In a further embodiment, $R_4$ or $R_5$ are independently phenyl or benzyl which are unsubstituted or substituted by one or more substituents chosen from halogen, $C_{1-6}$ alkyl, $NR_{63}R_{64}$, nitro, $CONR_{63}R_{64}$, $C_{1-6}$ alkyloxy, $C(O)OR_{62}$, cyano, and azido;

wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen to form a 3 to 10 member heterocycle.

In a further embodiment, $R_4$ or $R_5$ are independently benzyl which are unsubstituted or substituted by one or more substituents chosen from halogen, $C_{1-6}$ alkyl, $NR_{63}R_{64}$, nitro, $CONR_{63}R_{64}$, $C_{1-6}$ alkyloxy, $C(O)OR_{62}$, cyano, and azido;

wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen to form a 3 to 10 member heterocycle.

In a further embodiment, $R_4$ or $R_5$ are independently chosen from phenyl, benzyl, pyridinyl, thiophenyl, benzofuran, thiazole, and pyrazole, which are unsubstituted or substituted by one or more substituents chosen from a halogen, $C_{1-6}$ alkyl, $C_{1-6}$ alkyloxy, $CF_3$, COOH, $COOC_{1-6}$ alkyl, cyano, $NH_2$, nitro, $NH(C_{1-6}$ alkyl), $N(C_{1-6}$ alkyl)$_2$ and a 3-8 member heterocycle.

$R_4$ or $R_5$ are independently benzyl unsubstituted or substituted by one or more substituents chosen from halogen, $C_{1-3}$ alkoxy, $SO_2C_{1-3}$alkyl, difluoromethoxy, trifluoromethoxy, trifluoromethyl, CN and pyrazoyl.

$R_4$ or $R_5$ are independently benzyl optionally substituted in the para (p) position.

In further embodiments:

$R_4$ or $R_5$ are independently benzyl;

$R_4$ or $R_5$ are independently benzyl substituted with a halogen;

$R_4$ or $R_5$ are independently benzyl substituted with Br;

$R_4$ or $R_5$ are independently benzyl substituted with F;

$R_4$ or $R_5$ are independently benzyl substituted with Cl;

$R_4$ or $R_5$ are independently benzyl substituted with at least one halogen;

$R_4$ or $R_5$ are independently benzyl substituted with a $C_{1-3}$ alkoxy;

$R_4$ or $R_5$ are independently benzyl substituted with methoxy;

$R_4$ or $R_5$ are independently benzyl substituted with ethoxy;

$R_4$ or $R_5$ are independently benzyl substituted with $SO_2C_{1-3}$alkyl;

$R_4$ or $R_5$ are independently benzyl substituted with methanesulfonyl;

$R_4$ or $R_5$ are independently benzyl substituted with difluoromethoxy;

$R_4$ or $R_5$ are independently benzyl substituted with trifluoromethoxy;

$R_4$ or $R_5$ are independently benzyl substituted with trifluoromethyl;

$R_4$ or $R_5$ are independently benzyl substituted with CN;

$R_4$ or $R_5$ are independently benzyl substituted with pyrrazoyl;

$R_4$ or $R_5$ are independently benzyl optionally substituted in the para (p) position.

In a further embodiment, $R_4$ or $R_5$ are independently azetidinyl, pyrrolidinyl, piperazinyl, piperidyl, piperidino, oxetanyl, tetrahydropyranyl, tetrahydrofuranyl, morpholinyl, $CH_2$-azetidinyl, $CH_2$-pyrrolidinyl, $CH_2$-piperazinyl, $CH_2$-piperidyl, $CH_2$-oxetanyl, $CH_2$-tetrahydropyranyl, $CH_2$-tetrahydrofuranyl, $CH_2$-morpholinyl any of which can be unsubstituted or substituted by one or more substituents chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, oxo, oxime, $NR_{63}R_{64}$, $C(O)OR_{62}$, cyano, azido, amidino and guanido;

wherein $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl, or $R_{65}$ and $R_{66}$ are taken together with the oxygen atoms to form a 5 to 10 member heterocycle, or $R_{63}$ and $R_{64}$ are taken together with the nitrogen atom to form a 3 to 10 member heterocycle.

In a further embodiment, $R_4$ or $R_5$ are independently azetidinyl, pyrrolidinyl, piperazinyl, piperidyl, piperidino, oxetanyl, tetrahydropyranyl, tetrahydrofuranyl, morpholinyl, $CH_2$-azetidinyl, $CH_2$-pyrrolidinyl, $CH_2$-piperazinyl, $CH_2$-piperidyl, $CH_2$-oxetanyl, $CH_2$-tetrahydropyranyl, $CH_2$-tetrahydrofuranyl, $CH_2$-morpholinyl any of which can be unsubstituted or substituted by one or more substituents chosen from halogen, $C_{1-6}$ alkyl, $NR_{63}R_{64}$, nitro, $CONR_{63}R_{64}$, $C_{1-6}$ alkyloxy, $C(O)OR_{62}$, cyano, and azido;

wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen to form a 3 to 10 member heterocycle.

In a further embodiment, $R_4$ or $R_5$ are independently azetidinyl, pyrrolidinyl, piperazinyl, piperidyl, piperidino, oxetanyl, tetrahydropyranyl, tetrahydrofuranyl, morpholinyl, $CH_2$-azetidinyl, $CH_2$-pyrrolidinyl, $CH_2$-piperazinyl, $CH_2$-piperidyl, $CH_2$-oxetanyl, $CH_2$-tetrahydropyranyl, $CH_2$-tetrahydrofuranyl, $CH_2$-morpholinyl any of which can be unsubstituted or substituted by one or more substituents chosen from a halogen, $C_{1-6}$ alkyl, $C_{1-6}$ alkyloxy, $CF_3$, COOH, $COOC_{1-6}$ alkyl, cyano, $NH_2$, nitro, $NH(C_{1-6}$ alkyl), $N(C_{1-6}$ alkyl)$_2$ and a 3-8 member heterocycle.

$R_4$ or $R_5$ are independently oxetanyl, tetrahydropyranyl, tetrahydrofuranyl, morpholinyl, $CH_2$-oxetanyl, $CH_2$-tetrahydropyranyl, $CH_2$-tetrahydrofuranyl, any of which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido.

$R_4$ or $R_5$ are independently $CH_2$-oxetanyl, $C_2$-tetrahydropyranyl, $CH_2$-tetrahydrofuranyl any of which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido.

$R_4$ or $R_5$ are independently optionally substituted $C_{1-12}$ alkyl (e.g., methyl, ethyl, isopropyl, cyclopropyl, cyclobutyl, tert-butyl, cyclopentyl, cyclohexyl, or cycloheptyl).

$R_4$ or $R_5$ are independently $C_{1-12}$ alkyl optionally substituted.

$R_4$ or $R_5$ are independently $C_{1-6}$ alkyl optionally substituted.

$R_4$ or $R_5$ are independently $C_{3-12}$ cycloalkyl optionally substituted.

$R_4$ or $R_5$ are independently $C_{3-10}$ cycloalkyl optionally substituted.

$R_4$ or $R_5$ are independently $C_{5-7}$ cycloalkyl optionally substituted.

$R_4$ or $R_5$ are independently optionally substituted $C_{6-7}$ cycloalkyl.

$R_4$ or $R_5$ are independently optionally substituted $C_6$ cycloalkyl.

In a further embodiment, $R_4$ or $R_5$ are independently chosen from methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl, any of which unsubstituted or substituted by one or more substituents chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, oxo, oxime, $NR_{63}R_{64}$, $C(O)OR_{62}$, cyano, azido, amidino and guanido;

wherein $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl, or $R_{65}$ and $R_{66}$ are taken together with the oxygen atoms to form a 5 to 10 member heterocycle, or $R_{63}$ and $R_{64}$ are taken together with the nitrogen atom to form a 3 to 10 member.

In a further embodiment, $R_4$ or $R_5$ are independently chosen from methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl any of which unsubstituted or substituted by one or more substituents chosen from halogen, nitro, $CONR_{63}R_{64}$, $C_{1-6}$ alkyl, $C_{2-6}$ alkenyl, $C_{1-6}$ alkyloxy, $C_{2-6}$ alkenyloxy, $C_{2-6}$ alkynyloxy, $C(O)C_{1-6}$ alkyl, $C_{6-12}$ aryl, 3-10 member heterocycle, 4-16 member heteroaralkyl, hydroxyl, $NR_{63}R_{64}$, $C(O)OR_{62}$, cyano, and azido;

wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen to form a 3 to 10 member heterocycle.

In a further embodiment, $R_4$ or $R_5$ are independently methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl any of which unsubstituted or substituted by one or two substituents chosen from halogen, $C_{1-6}$ alkyl, $NR_{63}R_{64}$, nitro, $CONR_{63}R_{64}$, $C_{1-6}$ alkyloxy, $C(O)OR_{62}$, cyano, and azido;

wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen to form a 3 to 10 member heterocycle.

In a further embodiment, $R_4$ or $R_5$ are independently methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl any of which unsubstituted or substituted by one or more substituents chosen from a halogen, $C_{1-6}$ alkyl, $C_{1-6}$ alkyloxy, $CF_3$, COOH, $COOC_{1-6}$ alkyl, cyano, $NH_2$, nitro, $NH(C_{1-6}$ alkyl), $N(C_{1-6}$ alkyl)$_2$ and a 3-8 member heterocycle.

In a further embodiment, $R_4$ or $R_5$ are independently chosen from methyl, ethyl, vinyl, propyl, propenyl, isopropyl, butyl, isobutyl, pentyl, neopentyl, or tert-butyl.

In a further embodiment, $R_4$ or $R_5$ are independently unsubstituted methyl or methyl substituted by one or more halogens.

In a further embodiment, $R_4$ or $R_5$ are independently unsubstituted methyl or methyl substituted by one or more fluoro.

In one embodiment, $R_4$ or $R_5$ are independently chosen from H, optionally substituted $C_{1-10}$ alkyl or optionally substituted $C_{7-12}$ aralkyl.

In a further embodiment, $R_4$ or $R_5$ are independently optionally substituted $C_{1-10}$ alkyl.

In a further embodiment, $R_4$ or $R_5$ are independently optionally substituted $C_{7-12}$ aralkyl.

In a further embodiment, $R_4$ is chosen from methyl, ethyl, vinyl, propyl, propenyl, isopropyl, butyl, isobutyl, pentyl, neopentyl, or tert-butyl.

In a further embodiment, $R_4$ is isopropyl or isobutyl.

$R_4$ is H.

$R_4$ is methyl.

$R_4$ is ethyl.

$R_4$ is isopropyl.

$R_4$ is isobutyl.

In a further embodiment, $R_5$ is isopropyl or isobutyl.

$R_5$ is H.

$R_5$ is methyl.

$R_5$ is ethyl.

$R_5$ is isopropyl.

$R_5$ is isobutyl.

$R_8$ is optionally substituted $C_{1-10}$ alkyl, optionally substituted $C_{6-12}$ aryl or optionally substituted 3 to 10 membered heterocycle.

$R_8$ is optionally substituted $C_{1-10}$ alkyl.

$R_8$ is H, optionally substituted $C_{1-10}$ alkyl, optionally substituted $C_{2-10}$ alkenyl, optionally substituted $C_{2-10}$ alkynyl, optionally substituted $C_{6-12}$ aryl, optionally substituted $C_{7-12}$ aralkyl, optionally substituted 3 to 10 membered heterocycle, or optionally substituted heteroaralkyl (e.g., wherein the heterocycle portion has 3 to 10 members and the alkyl portion has 1 to 6 carbon atoms).

$R_8$ is $C_{1-10}$ alkyl, $C_{2-10}$ alkenyl, 3 to 10 membered heterocycle, or heteroaralkyl (e.g., wherein the heterocycle portion has 3 to 10 members and the alkyl portion has 1 to 6 carbon atoms) which in each case are optionally substituted.

$R_8$ is 3 to 10 membered heterocycle or 4-16 member heteroaralkyl any of which can be unsubstituted or substituted by one or more substituents chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, C(O)$C_{1-6}$ alkyl, C(O)$C_{2-6}$ alkenyl, C(O)$C_{2-6}$ alkynyl, C(O)$C_{6-12}$ aryl, C(O)$C_{7-12}$ aralkyl, 3-10 member heterocycle, 4-16 member heteroaralkyl, hydroxyl, $NR_{63}R_{64}$, C(O)$OR_{62}$, cyano, azido, amidino and guanido;
wherein $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl,
or $R_{65}$ and $R_{66}$ are taken together with the oxygen atoms to form a 5 to 10 member heterocycle,
or $R_{63}$ and $R_{64}$ are taken together with the nitrogen atom to form a 3 to 10 member heterocycle.

$R_8$ is 3 to 10 membered heterocycle or 4-16 member heteroaralkyl any of which can be unsubstituted or substituted by one or more substituents chosen from halogen, nitro, $CONR_{63}R_{64}$, $C_{1-6}$ alkyl, $C_{2-6}$ alkenyl, $C_{1-6}$ alkyloxy, $C_{2-6}$ alkenyloxy, $C_{2-6}$ alkynyloxy, C(O)$C_{1-6}$ alkyl, $C_{6-12}$ aryl, 3-10 member heterocycle, 4-16 member heteroaralkyl, hydroxyl, $NR_{63}R_{64}$, C(O)$OR_{62}$, cyano, and azido;
wherein $R_{62}$, $R_{63}$ and $R_{64}$ are each independently chosen from H, $C_{1-12}$ alkyl, $C_{6-12}$ aryl, 3-12 member heterocycle, 4-16 member heteroaralkyl, and $C_{7-18}$ aralkyl,
or $R_{63}$ and $R_{64}$ are taken together with the nitrogen to form a 3 to 10 member heterocycle.

$R_8$ is 3 to 10 membered heterocycle or 4-16 member heteroaralkyl any of which can be unsubstituted or substituted by one or more substituents chosen from halogen, $C_{1-6}$ alkyl, $NR_{63}R_{64}$, nitro, $CONR_{63}R_{64}$, $C_{1-6}$ alkyloxy, C(O)$OR_{62}$, cyano, and azido;
wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl,
or $R_{63}$ and $R_{64}$ are taken together with the nitrogen to form a 3 to 10 member heterocycle,.

$R_8$ is 3 to 10 membered heterocycle or 4-16 member heteroaralkyl any of which can be unsubstituted or substituted by one or more substituents chosen from halogen, $C_{1-6}$ alkyl, $NH_2$, nitro, C(O)O$C_{1-6}$ alkyl, COOH, $C_{1-6}$ alkyloxy, cyano, and azido.

$R_8$ is azetidinyl, pyrrolidinyl, piperazinyl, piperidyl, piperidino, oxetanyl, tetrahydropyranyl, tetrahydrofuranyl, morpholinyl, $CH_2$-azetidinyl, $CH_2$-pyrrolidinyl, $CH_2$-piperazinyl, $CH_2$-piperidyl, $CH_2$-oxetanyl, $CH_2$-tetrahydropyranyl, $CH_2$-tetrahydrofuranyl, $CH_2$-morpholinyl any of which can be unsubstituted or substituted by one or more substituents chosen from halogen, $C_{1-6}$ alkyl, $NH_2$, nitro, C(O)O$C_{1-6}$ alkyl, COOH, $C_{1-6}$alkyloxy, cyano, and azido.

$R_8$ is H, optionally substituted $C_{1-10}$ alkyl, optionally substituted $C_{2-10}$ alkenyl, optionally substituted $C_{2-10}$ alkynyl.

In accordance with a further aspect of the invention, $R_8$ is optionally substituted $C_{1-12}$ alkyl (e.g., methyl, ethyl, isopropyl, cyclopropyl, cyclobutyl, tert-butyl, cyclopentyl, cyclohexyl, or cycloheptyl, especially cyclohexyl).

In a further embodiment, $R_8$ is $C_{1-12}$ alkyl optionally substituted.

In a further embodiment, $R_7$ is $C_{3-12}$ cycloalkyl optionally substituted.

In a further embodiment, $R_8$ is $C_{3-10}$ cycloalkyl optionally substituted.

In a further embodiment, $R_8$ is $C_{5-7}$ cycloalkyl optionally substituted.

In one embodiment, $R_8$ is optionally substituted $C_{6-7}$ cycloalkyl.

In one embodiment, $R_8$ is optionally substituted $C_6$ cycloalkyl.

In a further embodiment, $R_8$ is $C_{1-12}$ alkyl unsubstituted or substituted by one or more substituents chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, C(O)$C_{1-6}$ alkyl, C(O)$C_{2-6}$ alkenyl, C(O)$C_{2-6}$ alkynyl, C(O)$C_{6-12}$ aryl, C(O)$C_{7-12}$ aralkyl, 3-10 member heterocycle, 4-16 member heteroaralkyl, hydroxyl, oxo, oxime, $NR_{63}R_{64}$, C(O)$OR_{62}$, cyano, azido, amidino and guanido;
wherein $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 4-10 member heterocycle, 4-16 member heteroaralkyl, and $C_{7-18}$ aralkyl, or $R_{65}$ and $R_{66}$ are taken together with the oxygen atoms to form a 5 to 10 member heterocycle, or $R_{63}$ and $R_{64}$ are taken together with the nitrogen atom to form a 3 to 10 member heterocycle.

In a further embodiment, $R_8$ is $C_{1-12}$ alkyl unsubstituted or substituted by one or more substituents chosen from halogen, nitro, $CONR_{63}R_{64}$, $C_{1-6}$ alkyl, $C_{2-6}$ alkenyl, $C_{1-6}$ alkyloxy, $C_{2-6}$ alkenyloxy, $C_{2-6}$ alkynyloxy, $C(O)C_{1-6}$ alkyl, $C_{6-12}$ aryl, 3-10 member heterocycle, 4-16 member heteroaralkyl, hydroxyl, $NR_{63}R_{64}$, $C(O)OR_{62}$, cyano, and azido;

wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen to form a 3 to 10 member heterocycle.

In a further embodiment, $R_8$ is $C_{1-12}$ alkyl unsubstituted or substituted by one or more substituents chosen from halogen, $C_{1-6}$ alkyl, $NR_{63}R_{64}$, nitro, $CONR_{63}R_{64}$, $C_{1-6}$ alkyloxy, $C(O)OR_{62}$, cyano, and azido;

wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen to form a 3 to 10 member heterocycle.

In a further embodiment, $R_8$ is $C_{3-12}$ cycloalkyl unsubstituted or substituted by one or more substituents chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)$ $C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, oxo, oxime, $NR_{63}R_{64}$, $C(O)OR_{62}$, cyano, azido, amidino, and guanido;

wherein $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl, or $R_{65}$ and $R_{66}$ are taken together with the oxygen atoms to form a 5 to 10 member heterocycle, or $R_{63}$ and $R_{64}$ are taken together with the nitrogen atom to form a 3 to 10 member heterocycle.

In a further embodiment, $R_8$ is $C_{3-12}$ cycloalkyl unsubstituted or substituted by one or more substituents chosen from halogen, nitro, $CONR_{63}R_{64}$, $C_{1-6}$ alkyl, $C_{2-6}$ alkenyl, $C_{1-6}$ alkyloxy, $C_{2-6}$ alkenyloxy, $C_{2-6}$ alkynyloxy, $C(O)C_{1-6}$ alkyl, $C_{6-12}$ aryl, 3-10 member heterocycle, 4-16 member heteroaralkyl, hydroxyl, $NR_{63}R_{64}$, $C(O)OR_{62}$, cyano, and azido;

wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen to form a 3 to 10 member heterocycle.

In a further embodiment, $R_8$ is $C_{3-12}$ cycloalkyl unsubstituted or substituted by one or more substituents chosen from halogen, $C_{1-6}$ alkyl, $NR_{63}R_{64}$, nitro, $CONR_{63}R_{64}$, $C_{1-6}$ alkyloxy, $C(O)OR_{62}$, cyano, and azido;

wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen to form a 3 to 10 member heterocycle.

In a further embodiment, $R_8$ is chosen from methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl, any of which can be unsubstituted or substituted by one or more substituents chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)$ $C_{6-12}$ aryl, $C(O)C_{7-12}$ aralkyl, 3-10 member heterocycle, 4-16 member heteroaralkyl, hydroxyl, oxo, oxime, $NR_{63}R_{64}$, $C(O)$ $OR_{62}$, cyano, azido, amidino, and guanido;

wherein $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl, or $R_{65}$ and $R_{66}$ are taken together with the oxygen atoms to form a 5 to 10 member heterocycle, or $R_{63}$ and $R_{64}$ are taken together with the nitrogen atom to form a 3 to 10 member heterocycle.

In a further embodiment, $R_8$ is chosen from methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl, any of which can be unsubstituted or substituted by one or more substituents chosen from halogen, nitro, $CONR_{63}R_{64}$, $C_{1-6}$ alkyl, $C_{2-6}$ alkenyl, $C_{1-6}$ alkyloxy, $C_{2-6}$ alkenyloxy, $C_{2-6}$ alkynyloxy, $C(O)C_{1-6}$ alkyl, $C_{6-12}$ aryl, 3-10 member heterocycle, 4-16 member heteroaralkyl, hydroxyl, $NR_{63}R_{64}$, $C(O)OR_{62}$, cyano, and azido;

wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen to form a 3 to 10 member heterocycle.

In a further embodiment, $R_8$ is chosen from methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl any of which can be unsubstituted or substituted by one or more substituents chosen from halogen, $C_{1-6}$ alkyl, $NR_{63}R_{64}$, nitro, $CONR_{63}R_{64}$, $C_{1-6}$ alkyloxy, $C(O)OR_{62}$, cyano, and azido;

wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen to form a 3 to 10 member heterocycle.

In a further embodiment, $R_8$ is cyclohexyl, cyclopentyl or cyclobutyl unsubstituted or substituted by one or more substituents independently chosen from halogen, nitro, nitroso, $SO_3Rf$, $SO_2Rf$, $PO_3R_{65}R_{66}$, $CONRgRh$, $C_{1-6}$ alkyl, $C_{7-18}$ aralkyl, $C_{6-12}$ aryl, $C_{1-6}$ alkyloxy, $C_{6-12}$ aryloxy, $C(O)C_{1-6}$ alkyl, $C(O)C_{6-12}$ aryl, $C(O)C_{7-12}$ aralkyl, $C(O)NHRf$, 3-10 member heterocycle, 4-16 member heteroaralkyl, hydroxyl, oxo, oxime, $NRgRh$, $C(O)ORf$, cyano, azido, amidino and guanido;

wherein Rf, $R_{65}$, $R_{66}$, Rg and Rh in each case are independently H, $C_{1-6}$ alkyl, $C_{2-6}$ alkenyl, $C_{2-6}$ alkynyl, $C_{6-12}$ aryl, 3-10 member heterocycle, 4-16 member heteroaralkyl, or $C_{7-18}$ aralkyl.

In still a further embodiment, $R_8$ is cyclohexyl, cyclopentyl or cyclobutyl unsubstituted or substituted by one or more substituents chosen from halogen, $SO_2Rf$, $CONRgRh$, $C_{1-6}$ alkyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{6-12}$ aryl, $C(O)C_{7-12}$ aralkyl, $C(O)NHRf$, 3-10 member heterocycle, 4-16 member heteroaralkyl, hydroxyl, oxo, oxime, $NRgRh$, $C(O)ORf$, cyano and azido;

wherein Rf, Rg and Rh in each case are independently H, $C_{1-6}$ alkyl, $C_{6-12}$ aryl, 3-10 member heterocycle, 4-16 member heteroaralkyl, $C_{7-18}$ aralkyl.

In one embodiment, $R_8$ is cyclohexyl, cyclopentyl or cyclobutyl unsubstituted or substituted by one or more substituents independently chosen from $C_{1-6}$ alkyl, halogen, $C_{2-6}$ alkenyl, $C_{2-6}$ alkynyl, $C_{1-6}$ alkyloxy, $C_{2-6}$ alkenyloxy and $C_{2-6}$ alkynyloxy.

In one embodiment, $R_8$ is cyclobutyl.

In one embodiment, $R_8$ is cyclobutyl substituted by one or more substituents independently chosen from fluoro, chloro, bromo and iodo.

In one embodiment, $R_8$ is cyclobutyl substituted by one or more fluoro.

In one embodiment, $R_8$ is cyclopentyl.

In one embodiment, $R_8$ is cyclopentyl substituted by one or more substituents independently chosen from fluoro, chloro, bromo and iodo.

In one embodiment, $R_8$ is cyclopentyl substituted by one or more fluoro.

In one embodiment, $R_8$ is cyclohexyl.

In one embodiment, $R_8$ is cyclohexyl substituted by one or more substituents independently chosen from fluoro, chloro, bromo and iodo.

In one embodiment, $R_8$ is cyclohexyl substituted by one or more fluoro.

In one embodiment, $R_8$ is 4,4-difluorocyclohexyl.

In a further embodiment, $R'_5$, $R''_5$, $R_6$, $R'_6$, $R_7$ and $R''_8$ are independently H or $C_{1-12}$ alkyl unsubstituted or substituted by one or more substituents chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, oxo, oxime, $NR_{63}R_{64}$, $C(O)OR_{62}$, cyano, azido, amidino and guanido;
  wherein $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 4-10 member heterocycle, 4-16 member heteroaralkyl, and $C_{7-18}$ aralkyl,
  or $R_{65}$ and $R_{66}$ are taken together with the oxygen atoms to form a 5 to 10 member heterocycle,
  or $R_{63}$ and $R_{64}$ are taken together with the nitrogen atom to form a 3 to 10 member heterocycle.

In a further embodiment, $R'_5$, $R''_5$, $R_6$, $R'_6$, $R_7$ and $R''_8$ are independently H or $C_{1-12}$ alkyl unsubstituted or substituted by one or more substituents chosen from halogen, nitro, $CONR_{63}R_{64}$, $C_{1-6}$ alkyl, $C_{2-6}$ alkenyl, $C_{1-6}$ alkyloxy, $C_{2-6}$ alkenyloxy, $C_{2-6}$ alkynyloxy, $C(O)C_{1-6}$ alkyl, $C_{6-12}$ aryl, 3-10 member heterocycle, 4-16 member heteroaralkyl, hydroxyl, $NR_{63}R_{64}$, $C(O)OR_{62}$, cyano, and azido;
  wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen to form a 3 to 10 member heterocycle.

In a further embodiment, $R'_5$, $R''_5$, $R_6$, $R'_6$, $R_7$ and $R''_8$ are independently H or $C_{1-6}$ alkyl unsubstituted or substituted by one or more substituents chosen from halogen, $C_{1-6}$ alkyl, $NR_{63}R_{64}$, nitro, $CONR_{63}R_{64}$, $C_{1-6}$ alkyloxy, $C(O)OR_{62}$, cyano, and azido;
  wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl,
  or $R_{63}$ and $R_{64}$ are taken together with the nitrogen to form a 3 to 10 member heterocycle.

In a further embodiment $R'_5$, $R''_5$, $R_6$, $R'_6$, $R_7$ and $R''_8$ are independently H, methyl, ethyl, vinyl, propyl, propenyl, isopropyl, butyl, isobutyl, pentyl, neopentyl, tert-butyl, cyclopropyl, cyclobutyl, cyclopentyl, cyclohexyl.

In a further embodiment $R'_5$, $R''_5$, $R_6$, $R'_6$, $R_7$ and $R''_8$ are H.

In one embodiment, the compounds of the present invention are the (+) enantiomer having an enantiomeric excess of 99%.

In one embodiment, the compounds of the present invention are the (+) enantiomer having an enantiomeric excess of 95%.

In one embodiment, the compounds of the present invention are the (+) enantiomer having an enantiomeric excess of 90%.

In one embodiment, the compounds of the present invention are the (−) enantiomer having an enantiomeric excess of 99%.

In one embodiment, the compounds of the present invention are the (−) enantiomer having an enantiomeric excess of 95%.

In one embodiment, the compounds of the present invention are the (−) enantiomer having an enantiomeric excess of 90%.

In one embodiment, there is provided a method of modulating chemokine receptor activity in a subject comprising administering to the subject a therapeutically effective amount of a compound of formula (I) or composition of the invention.

In another embodiment, there is provided a method for the prevention or treatment of diseases associated with the modulation of chemokine receptor activity in a subject in need of such treatment comprising administering to the subject a therapeutically effective amount of a compound of formula (I) or composition of the invention.

In a further embodiment, there is provided a method for prevention or treatment of certain inflammatory diseases, immunoregulatory diseases, organ transplantation reactions and in the prevention and treatment of infectious diseases such as HIV infections in a subject in need of such treatment comprising administering to the subject a therapeutically effective amount of a compound of formula (I) or composition of the invention.

In another embodiment, there is provided a method for the prevention or treatment of diseases associated with the modulation of CCR5 chemokine receptor activity in a subject in need of such treatment comprising administering to the subject a therapeutically effective amount of a compound of formula (I) or composition of the invention.

In still another aspect, there is provided a method for blocking cellular entry of HIV in a subject in need thereof comprising administering to the subject a therapeutically effective amount of a compound of formula (I) to block HIV from cellular entry in said subject.

In still another aspect, there is provided a method for prevention or treatment of HIV infections in a subject in need of such treatment comprising administering to the subject a therapeutically effective amount of a compound of formula (I) or composition of the invention.

In still another aspect, there is provided a method for delaying the onset of AIDS or treating AIDS in a subject in need of such treatment comprising administering to the subject a therapeutically effective amount of a compound of formula (I) or composition of the invention.

In a further embodiment, there is provided a method for the prevention or treatment of diseases associated with the modulation of chemokine receptor activity in a subject in need of such treatment comprising administering to the subject a pharmaceutical combination comprising at least one compound of formula (I) and at least one further therapeutic agent.

In a further embodiment, there is provided a method for the prevention or treatment of diseases associated with the modulation of CCR5 chemokine receptor activity in a subject in need of such treatment comprising administering to the subject a pharmaceutical combination comprising at least one compound of formula (I) and at least one further therapeutic agent.

In still another aspect, there is provided a method for blocking cellular entry of HIV in a subject or for the prevention or treatment of HIV infections in a subject in need of such treatment comprising administering to the subject a pharmaceutical combination comprising at least one compound of formula (I) and at least one further therapeutic agent.

In still another aspect, there is provided a method for delaying the onset of AIDS or treating AIDS in a subject in need of such treatment comprising administering to the subject a pharmaceutical combination comprising at least one compound of formula (I) and at least one further therapeutic agent.

In another embodiment, there is provided a combination useful for the prevention or treatment of diseases associated with the modulation of chemokine receptor activity which is a therapeutically effective amount of a compound of formula (I) and therapeutically effective amount of at least one further therapeutic agent.

In one embodiment, combinations of the present invention comprise those wherein the following embodiments are present, either independently or in combination.

In a further embodiments the pharmaceutical combinations of this invention may contain at least one further therapeutic agent chosen from an agent used in inflammatory diseases, immunoregulatory diseases and in organ transplantation reactions.

In another embodiment, the pharmaceutical combination of this invention may contain at least one further therapeutic agent which is an antiviral agent.

In one embodiment, the pharmaceutical combination of this invention may contain at least one further antiviral agent which is chosen from nucleoside and nucleotide analog reverse transcriptase inhibitors, non-nucleoside reverse transcriptase inhibitors, protease inhibitors, attachment and fusion inhibitors, integrase inhibitors or maturation inhibitors.

In one embodiment, the pharmaceutical combinations of this invention may contain at least one other antiviral agent which is a nucleoside and nucleotide analog reverse transcriptase inhibitors chosen from 3TC (lamivudine, Epivir®), AZT (zidovudine, Retrovir®), Emtricitabine (Coviracil®, formerly FTC), d4T (2',3'-dideoxy-2',3'-didehydro-thymidine, stavudine and Zerit®), tenofovir (Viread®), 2',3'-dideoxyinosine (ddI, didanosine, Videx®), 2',3'-dideoxycytidine (ddC, zalcitabine, Hivid®), Combivir® (AZT/3TC or zidovudine/lamivudine combination), Trivizir® (AZT/3TC/abacavir or zidovudine/lamivudine/abacavir combination), abacavir (1592U89, Ziagen®), SPD-754, ACH-126,443 (Beta-L-Fd4C), Alovudine (MIV-310), DAPD (amdoxovir), Racivir, 9-[(2-hydroxymethyl)-1,3-dioxolan-4-yl]guanine or 2-amino-9-[(2-hydroxymethyl)-1,3-dioxolan-4-yl]adenine.

In another embodiment, the pharmaceutical combination of this invention may contain at least one other antiviral agent which is a non-nucleoside reverse transcriptase inhibitor chosen from Nevirapine (Viramune®, NVP, BI-RG-587), delavirdine (Rescriptor®, DLV), efavirenz (DMP 266, Sustiva®), (+)-Calanolide A, Capravirine (AG1549, formerly S-1153), DPC083, MIV-150, TMC120, TMC125 or BHAP (delavirdine), calanolides or L-697,661 (2-Pyridinone 3benzoxazolMeNH derivative).

In another embodiment, the pharmaceutical combination of this invention may contain at least one other antiviral agent which is a protease inhibitor chosen from nelfinavir (Viracept®, NFV), amprenavir (141W94, Agenerase®), indinavir (MK-639, IDV, Crixivan®), saquinavir (Invirase®, Fortovase®, SQV), ritonavir (Norvir®, RTV), lopinavir (ABT-378, Kaletra®), Atazanavir (BMS232632), mozenavir (DMP-450), fosamprenavir (GW433908), RO033-4649, Tipranavir (PNU-140690), TMC114 or VX-385.

In another embodiment, the pharmaceutical combination of this invention may contain at least one other antiviral agent which is an attachment and fusion inhibitor chosen from T-20 (enfuvirtide, Fuzeon®), T-1249, Schering C (SCH-C), Schering D (SCH-D), FP21399, PRO-140, PRO 542, PRO 452, TNX-355, GW873140 (AK602), TAK-220, TAK-652, UK-427,857 or soluble CD4, CD4 fragments, CD4-hybrid molecules, BMS-806, BMS-488043, AMD3100, AMD070 or KRH-2731.

In another embodiment, the pharmaceutical combination of this invention may contain at least one other antiviral agent which is an integrase inhibitor chosen from S-1360, L-870, 810, JKT 303, L-870,812 or C-2507.

In another embodiment, the pharmaceutical combination of this invention may contain at least one other antiviral agent which is a maturation inhibitor and is PA-457.

In another embodiment, the pharmaceutical combination of this invention may contain at least one other antiviral agent which is a zinc finger inhibitor and is azodicarbonamide (ADA).

In another embodiment, the pharmaceutical combination of this invention may contain at least one other antiviral agent which is an antisense drug and is HGTV43.

In another embodiment, the pharmaceutical combination of this invention may contain at least one other antiviral agent which is an immunomodulator, immune stimulator or cytokine chosen from interleukin-2 (IL-2, Aldesleukin, Proleukin), granulocyte macrophage colony stimulating factor (GM-CSF), erythropoietin, Multikine, Ampligen, thymomodulin, thymopentin, foscarnet, HE2000, Reticulose, Murabutide, Resveratrol, HRG214, HIV-1 Immunogen (Remune) or EP HIV-1090.

In another embodiment, the pharmaceutical combination of this invention may contain at least one other antiviral agent chosen from 2',3'-dideoxyadenosine, 3'-deoxythymidine, 2',3'-dideoxy-2',3'-didehydrocytidine and ribavirin; acyclic nucleosides such as acyclovir, ganciclovir; interferons such as alpha-, beta- and gamma-interferon; glucuronation inhibitors such as probenecid; or TIBO drugs, HEPT, TSAO derivatives.

The combinations referred to above may conveniently be presented for use in the form of a pharmaceutical formulation and thus pharmaceutical formulations comprising a combination as defined above together with a pharmaceutically acceptable carrier thereof comprises a further aspect of the invention.

The individual components of such combinations may be administered either sequentially or simultaneously in separate or combined pharmaceutical formulations.

In a further embodiment, the said compound of formula (I) and said therapeutic agent are administered sequentially.

In a further embodiment, the said compound of formula (I) and said therapeutic agent are administered simultaneously.

The subject to which the compounds are administered can be, for example, a mammal or a human. Preferably, the subject is a human.

In one embodiment, the present invention further provides a pharmaceutical composition comprising at least one compound having the formula (I) or pharmaceutically acceptable salts or pharmaceutically acceptable hydrates or pharmaceutically acceptable solvates thereof and at least one pharmaceutically acceptable carrier or excipient.

In another embodiment, the invention provides the use of a compound having the formula (I) for the manufacture of a medicament for prevention and treatment of diseases associated with the modulation of CCR5 chemokine receptor activity in a host comprising administering a therapeutically effective amount of a compound of formula (I).

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

The term "alkyl" represents a linear, branched or cyclic hydrocarbon moiety having, for example, 1 to 10 carbon atoms, which may have one or more double bonds or triple bonds in the chain, and is optionally substituted. For example, unless otherwise stated, suitable substituents include halogen, amino, amidino, amido, azido, cyano, guanido, hydroxyl, nitro, nitroso, urea, $OS(O)_2R_{21}$ (wherein $R_{21}$ is selected from $C_{1-6}$ alkyl, $C_{6-12}$ aryl or 3 to 10 membered heterocycle), $OS(O)_2OR_{22}$ (wherein $R_{22}$ is selected from H, $C_{1-6}$ alkyl, $C_{6-12}$ aryl or 3 to 10 membered heterocycle), $S(O)_2OR_{23}$ (wherein $R_{23}$ is selected from H, $C_{1-6}$ alkyl, $C_{6-12}$ aryl or 3 to 10 membered heterocycle), $S(O)_{0-2}R_{24}$ (wherein $R_{24}$ is selected from H, $C_{1-6}$ alkyl, $C_{6-12}$ aryl or 3 to 10 membered heterocycle), $OP(O)OR_{25}OR_{26}$, $P(O)OR_{25}OR_{26}$ (wherein $R_{25}$ and $R_{26}$ are each independently selected from H or $C_{1-6}$ alkyl), $C(O)R_{27}$ (wherein $R_{27}$ is selected from H, $C_{1-6}$ alkyl, $C_{6-12}$ aryl or 3 to 10 membered heterocycle), $C(O)OR_{28}$ (wherein $R_{28}$ is selected from H, $C_{1-6}$ alkyl, $C_{6-12}$ aryl, $C_{6-12}$ aralkyl (e.g. $C_{7-12}$ aralkyl) or 3 to 10 membered heterocycle), $NR_{29}C(O)R_{30}$, $NR_{29}C(O)OR_{30}$, $NR_{31}C(O)NR_{29}R_{30}$, $C(O)NR_{29}R_{30}$, $OC(O)NR_{29}R_{30}$ (wherein $R_{29}$, $R_{30}$ and $R_{31}$ are each independently selected from H, $C_{1-6}$ alkyl, $C_{6-12}$ aryl, $C_{6-12}$ aralkyl (e.g. $C_{7-12}$ aralkyl) or 3 to 10 membered heterocycle, or $R_{29}$ and $R_{30}$ are taken together with the atoms to which they are attached to form a 3 to 10 membered heterocycle), $SO_2NR_{32}R_{33}$, $NR_{32}SO_2R_{33}$ (wherein $R_{32}$ and $R_{33}$ are each independently selected from the group consisting of H, $C_{1-6}$ alkyl, $C_{6-12}$ aryl, 3 to 10 membered heterocycle and $C_{6-12}$ aralkyl (e.g. $C_{7-12}$ aralkyl)), $C(R_{34})NR_{35}$ or $C(R_{34})NOR_{35}$ (wherein $R_{34}$ and $R_{35}$ are each independently selected from the group consisting of H, $C_{1-6}$ alkyl, or $C_{6-12}$ aryl).

Preferred substituents for the alkyl groups include halogen (Br, Cl, I or F), cyano, nitro, oxo, amino, COOH, COO—$C_{1-4}$ alkyl, CO—$C_{1-4}$ alkyl, and phenyl.

Examples of alkyl groups include but are not limited to methyl, ethyl, propyl, isopropyl, butyl, isobutyl, sec-butyl, tert-butyl, pentyl, isopentyl, neopentyl, tert-pentyl, hexyl, isohexyl, neohexyl, allyl, vinyl, acetylenyl, ethylenyl, propenyl, isopropenyl butenyl, isobutenyl, hexenyl, butadienyl, pentenyl, pentadienyl, hexenyl, hexadienyl, hexatrienyl, heptenyl, heptadienyl, heptatrienyl, octenyl, octadienyl, octatrienyl, octatetraenyl, propynyl, butynyl, pentynyl, hexynyl, cyclopropyl, cyclobutyl, cycloheptyl, cyclohexenyl, cyclohex-dienyl and cyclohexyl.

The term alkyl is also meant to include alkyls in which one or more hydrogen atom is replaced by a halogen, i.e. an alkylhalide. Examples include but are not limited to trifluoromethyl, difluoromethyl, fluoromethyl, trichloromethyl, dichloromethyl, chloromethyl, trifluoroethyl, difluoroethyl, fluoroethyl, trichloroethyl, dichloroethyl, chloroethyl, chlorofluoromethyl, chlorodifluoromethyl, dichlorofluoroethyl.

The term "alkenyl" refers to alkyl groups may have one or more double bonds in the chain. The term "alkynyl" refers to alkyl groups may have one or more triple bonds in their chain. The alkenyl and alkynyl groups can be optionally substituted as described above for the alkyl groups.

The term "alkoxy" represents an alkyl which is covalently bonded to the adjacent atom through an oxygen atom. Examples include but are not limited to methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy and neohexyloxy.

The term "alkylamino" represents an alkyl which is covalently bonded to the adjacent atom through a nitrogen atom and may be monoalkylamino or dialkylamino, wherein the alkyl groups may be the same or different. Examples include but are not limited to methylamino, dimethylamino, ethylamino, diethylamino, methylethylamino, propylamino, isopropylamino, butylamino, isobutylamino, sec-butylamino, tert-butylamino, pentylamino, isopentylamino, neopentylamino, tert-pentylamino, hexylamino, isohexylamino and neohexylamino.

The term "alkyloxycarbonyl" represents an alkyloxy which is covalently bonded to the adjacent atom through carbonyl (C=O). Examples include but are not limited to methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, tert-pentyloxycarbonyl, hexyloxycarbonyl, isohexyloxycarbonyl and neohexyloxycarbonyl.

The term "amidino" represents —C(=NR$_{10}$)NR$_{11}$R$_{12}$, wherein R$_{10}$, R$_{11}$ and R$_{12}$ are each independently selected from H, C$_{1-6}$ alkyl, C$_{6-12}$ aryl or C$_{6-12}$ aralkyl (e.g. C$_{7-12}$ aralkyl), or R$_{11}$ and R$_{12}$ are taken together with the nitrogen to which they are attached to form a 3 to 10 membered heterocycle.

The term "amido" represents —CONH$_2$, —CONHR$_{13}$ and —CONR$_{13}$R$_{14}$ wherein R$_{13}$ and R$_{14}$ are each independently selected from C$_{1-6}$ alkyl, C$_{6-12}$ aryl, 3 to 10 membered heterocycle or C$_{6-12}$ aralkyl (e.g. C$_{7-12}$ aralkyl), or R$_{13}$ and R$_{14}$ are taken together with the nitrogen to which they are attached to form a 3 to 10 membered heterocycle.

The term "amino" represents a derivative of ammonia obtained by substituting one or more hydrogen atom and include —NH$_2$, —NHR$_{15}$ and —NR$_{15}$R$_{16}$, wherein R$_{15}$ and R$_{16}$ are each independently selected from C$_{1-6}$ alkyl, C$_{6-12}$ aryl or C$_{6-12}$ aralkyl (e.g. C$_{7-12}$ aralkyl), or R$_{15}$ and R$_{16}$ are taken together with the nitrogen to which they are attached to form a 3 to 10 membered heterocycle.

The term "aryl" represents a carbocyclic moiety containing at least one benzenoid-type ring (i.e. the aryl group may be monocyclic or polycyclic), and which is optionally substituted with one or more substituents. For example, unless otherwise stated, suitable substituents include halogen, halogenated C$_{1-6}$ alkyl, halogenated C$_{1-6}$ alkoxy, amino, amidino, amido, azido, cyano, guanido, hydroxyl, nitro, nitroso, urea, OS(O)$_2$R$_{21}$ (wherein R$_{21}$ is selected from C$_{1-6}$ alkyl, C$_{6-12}$ aryl or 3 to 10 membered heterocycle), OS(O)$_2$OR$_{22}$ (wherein R$_{22}$ is selected from H, C$_{1-6}$ alkyl, C$_{6-12}$ aryl or 3 to 10 membered heterocycle), S(O)$_2$OR$_{23}$ (wherein R$_{23}$ is selected from H, C$_{1-6}$ alkyl, C$_{6-12}$ aryl or 3 to 10 membered heterocycle), S(O)$_{0-2}$R$_{24}$ (wherein R$_{24}$ is selected from H, C$_{1-6}$ alkyl, C$_{6-12}$ aryl or 3 to 10 membered heterocycle), OP(O)OR$_{25}$OR$_{26}$, P(O)OR$_{25}$OR$_{26}$ (wherein R$_{25}$ and R$_{26}$ are each independently selected from H or C$_{1-6}$ alkyl), C$_{1-6}$alkyl, C$_{6-12}$ aralkyl (e.g. C$_{7-12}$ aralkyl), C$_{1-6}$alkoxy, C$_{6-12}$aralkyloxy (e.g. C$_{7-12}$ aralkyloxy), C$_{6-12}$aryloxy, 3 to 10 membered heterocycle, C(O)R$_{27}$ (wherein R$_{27}$ is selected from H, C$_{1-6}$ alkyl, C$_{6-12}$ aryl or 3 to 10 membered heterocycle), C(O)OR$_{28}$ (wherein R$_{28}$ is selected from H, C$_{1-6}$ alkyl, C$_{6-12}$ aryl, C$_{6-12}$ aralkyl (e.g. C$_{7-12}$ aralkyl) or 3 to 10 membered heterocycle), NR$_{29}$C(O)R$_{30}$, NR$_{29}$C(O) OR$_{30}$, NR$_{31}$C(O) NR$_{29}$R$_{30}$, C(O)NR$_{29}$R$_{30}$, OC(O) NR$_{29}$R$_{30}$ (wherein R$_{29}$, R$_{30}$ and R$_{31}$ are each independently selected from H, C$_{1-6}$ alkyl, C$_{6-12}$ aryl, C$_{6-12}$ aralkyl (e.g. C$_{7-12}$ aralkyl) or 3 to 10 membered heterocycle, or R$_{29}$ and R$_{30}$ are taken together with the atoms to which they are attached to form a 3 to 10 membered heterocycle), SO$_2$NR$_{32}$R$_{33}$, NR$_{32}$SO$_2$R$_{33}$ (wherein R$_{32}$ and R$_{33}$ are each independently selected from the group consisting of H, C$_{1-6}$ alkyl, C$_{6-12}$ aryl, 3 to 10 membered heterocycle and C$_{6-12}$ aralkyl (e.g. C$_{7-12}$ aralkyl)), C(R$_{34}$)NR$_{35}$ or C(R$_{34}$)NOR$_{35}$ (wherein R$_{34}$ and R$_{35}$ are each independently selected from the group consisting of H, C$_{1-6}$ alkyl, or C$_{6-12}$ aryl).

Preferred substituents for the aryl groups include halogen (Br, Cl, I or F), cyano, nitro, oxo, amino, C$_{1-4}$ alkyl (e.g., CH$_3$, C$_2$H$_5$, isopropyl), C$_{1-4}$ alkoxy (e.g., OCH$_3$, OC$_2$H$_5$), halogenated C$_{1-4}$ alkyl (e.g., CF$_3$, CHF$_2$), halogenated C$_{1-4}$ alkoxy (e.g., OCF$_3$, OC$_2$F$_5$), COOH, COO—C$_{1-4}$ alkyl, CO—C$_{1-4}$ alkyl, C$_{1-4}$ alkyl-S— (e.g., CH$_3$S, C$_2$H$_5$S), halogenated C$_{1-4}$ alkyl-S— (e.g., CF$_3$S, C$_2$F$_5$S), benzyloxy, and pyrazolyl.

Examples of aryl include but are not limited to phenyl, tolyl, dimethylphenyl, aminophenyl, anilinyl, naphthyl, anthryl, phenanthryl or biphenyl.

The term "aralkyl" represents an aryl group attached to the adjacent atom by a C$_{1-6}$alkyl. Examples include but are not limited to benzyl, benzhydryl, trityl, phenethyl, 3-phenylpropyl, 2-phenylpropyl, 4-phenylbutyl and naphthylmethyl. The aryl and alkyl portions can be optionally substituted as described above.

The term "aralkyloxy" represents an aralkyl which is covalently bonded to the adjacent atom through an oxygen atom. Examples include but are not limited to benzyloxy, benzhydryloxy, trityloxy, phenethyloxy, 3-phenylpropyloxy, 2-phenylpropyloxy, 4-phenylbutyloxy and naphthylmethoxy. The aryl and alkyl portions can be optionally substituted as described above.

The term "aryloxy" represents an aryl which is covalently bonded to the adjacent atom through an oxygen atom. Examples include but are not limited to phenoxy and naphthyloxy. The aryl portion can be optionally substituted as described above.

There is also provided "enantiomers" and "diastereoisomers" of the present invention. It will be appreciated that the compounds in accordance with the present invention can contain one or more chiral centers. The compounds in accordance with the present invention may thus exist in the form of two different optical isomers, that is (+) or (−) enantiomers or in the form of different diastereomers. All such enantiomers, diastereomers and mixtures thereof, including racemic or other ratio mixtures of individual enantiomers and diastereomers, are included within the scope of the invention. The single diastereomer can be obtained by methods well known to those of ordinary skill in the art, such as HPLC, crystallization and chromatography. The single enantiomer can be obtained by methods well known to those of ordinary skill in the art, such as chiral HPLC, enzymatic resolution and chiral auxiliary derivatization.

The optical purity is numerically equivalent to the "enantiomeric excess". The term "enantiomeric excess" is defined in percentage (%) value as follows: [mole fraction (major enantiomer)−mole fraction (minor enantiomer)]×100. An example of enantiomeric excess of 99% represents a ratio of 99.5% of one enantiomer and 0.5% of the opposite enantiomer.

The term "guanido" or "guanidino" represents —NR$_{17}$C(=NR$_{18}$)NR$_{19}$R$_{20}$ wherein R$_{17}$, R$_{18}$, R$_{19}$ and R$_{20}$ are each independently selected from H, C$_{1-6}$ alkyl, C$_{6-12}$ aryl or C$_{6-12}$ aralkyl (e.g. C$_{7-12}$ aralkyl), or R$_{19}$ and R$_{20}$ are taken together with the nitrogen to which they are attached to form a 3 to 10 membered heterocycle.

The term "halogen" is specifically a fluoride atom, chloride atom, bromide atom or iodide atom.

The term "heterocycle" represents an optionally substituted saturated, unsaturated or aromatic cyclic moiety wherein said cyclic moiety is interrupted by at least one heteroatom selected from oxygen (O), sulfur (S) or nitrogen (N). Heterocycles may be monocyclic or polycyclic rings. For example, unless otherwise stated, suitable substituents include halogen, halogenated C$_{1-6}$ alkyl, halogenated C$_{1-6}$ alkoxy, amino, amidino, amido, azido, cyano, guanido, hydroxyl, nitro, nitroso, urea, OS(O)$_2$R$_{21}$ (wherein R$_{21}$ is selected from C$_{1-6}$ alkyl, C$_{6-12}$ aryl or 3 to 10 membered heterocycle), OS(O)$_2$OR$_{22}$ (wherein R$_{22}$ is selected from H, C$_{1-6}$ alkyl, C$_{6-12}$ aryl or 3 to 10 membered heterocycle), S(O)$_2$OR$_{23}$ (wherein R$_{23}$ is selected from H, C$_{1-6}$ alkyl, C$_{6-12}$ aryl or 3 to 10 membered heterocycle), $S(O)_{0-2}R_{24}$ (wherein $R_{24}$ is selected from H, $C_{1-6}$ alkyl, $C_{6-12}$ aryl or 3 to 10 membered heterocycle), $OP(O)OR_{25}OR_{26}$, $P(O)OR_{25}OR_{26}$ (wherein $R_{25}$ and $R_{26}$ are each independently selected from H or $C_{1-6}$ alkyl), $C_{1-6}$alkyl, $C_{6-12}$aralkyl (e.g. $C_{7-12}$ aralkyl), $C_{1-6}$alkoxy, $C_{6-12}$ aryl, $C_{6-12}$aralkyloxy (e.g. $C_{7-12}$ aralkyloxy), $C_{6-12}$aryloxy, $C(O)R_{27}$ (wherein $R_{27}$ is selected from H, $C_{1-6}$ alkyl, $C_{6-12}$ aryl or 3 to 10 membered heterocycle), $C(O)OR_{28}$ (wherein $R_{28}$ is selected from H, $C_{1-6}$ alkyl, $C_{6-12}$ aryl, $C_{6-12}$ aralkyl (e.g. $C_{7-12}$ aralkyl) or 3 to 10 membered heterocycle), $NR_{29}C(O)R_{30}$, $NR_{29}C(O)OR_{30}$, $NR_{31}C(O)NR_{29}R_{30}$, $C(O)NR_{29}R_{30}$, $OC(O)NR_{29}R_{30}$ (wherein $R_{29}$, $R_{30}$ and $R_{31}$ are each independently selected from H, $C_{1-6}$ alkyl, $C_{6-12}$ aryl, $C_{6-12}$ aralkyl (e.g. $C_{7-12}$ aralkyl) or 3 to 10 membered heterocycle, or $R_{29}$ and $R_{30}$ are taken together with the atoms to which they are attached to form a 3 to 10 membered heterocycle), $SO_2NR_{32}R_{33}$, $NR_{32}SO_2R_{33}$ (wherein $R_{32}$ and $R_{33}$ are each independently selected from the group consisting of H, $C_{1-6}$ alkyl, $C_{6-12}$ aryl, 3 to 10 membered heterocycle and $C_{6-12}$ aralkyl (e.g. $C_{7-12}$ aralkyl)), $C(R_{34})NR_{35}$ or $C(R_{34})NOR_{35}$ (wherein $R_{34}$ and $R_{35}$ are each independently selected from the group consisting of H, $C_{1-6}$ alkyl, or $C_{6-12}$ aryl).

Preferred substituents for the heterocycle groups include halogen (Br, Cl, I or F), cyano, nitro, oxo, amino, $C_{1-4}$ alkyl (e.g., $CH_3$, $C_2H_5$, isopropyl), $C_{1-4}$ alkoxy (e.g., $OCH_3$, $OC_2H_5$), halogenated $C_{1-4}$ alkyl (e.g., $CF_3$, $CHF_2$), halogenated $C_{1-4}$ alkoxy (e.g., $OCF_3$, $OC_2F_5$), COOH, COO—$C_{1-4}$ alkyl, CO—$C_{1-4}$ alkyl, $C_{1-4}$ alkyl-S— (e.g., $CH_3S$, $C_2H_5S$), halogenated $C_{1-4}$ alkyl-S— (e.g., $CF_3S$, $C_2F_5S$), benzyloxy, and pyrazolyl.

Examples of heterocycles include but are not limited to azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, morpholino, oxetanyl, oxadiazolyl, oxiranyl, oxazinyl, oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl, thiopyranyl furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl.

The term "heteroaralkyl" represents a heterocycle group attached to the adjacent atom by a $C_{1-6}$ alkyl. The heterocycle and alkyl portions can be optionally substituted as described above.

The term "independently" means that a substituent can be the same or a different definition for each item.

Unless otherwise stated, the term "optionally substituted" represents one or more halogen, halogenated $C_{1-6}$ alkyl, halogenated $C_{1-6}$ alkoxy, amino, amidino, amido, azido, cyano, guanido, hydroxyl, nitro, nitroso, urea, $OS(O)_2R_{21}$ (wherein $R_{21}$ is selected from $C_{1-6}$ alkyl, $C_{6-12}$ aryl or 3 to 10 membered heterocycle), $OS(O)_2OR_{22}$ (wherein $R_{22}$ is selected from H, $C_{1-6}$ alkyl, $C_{6-12}$ aryl or 3 to 10 membered heterocycle), $S(O)_2OR_{23}$ (wherein $R_{23}$ is selected from H, $C_{1-6}$ alkyl, $C_{6-12}$ aryl or 3 to 10 membered heterocycle), $S(O)_{0-2}R_{24}$ (wherein $R_{24}$ is selected from H, $C_{1-6}$ alkyl, $C_{6-12}$ aryl or 3 to 10 membered heterocycle), $OP(O)OR_{25}OR_{26}$, $P(O)OR_{25}OR_{26}$ (wherein $R_{25}$ and $R_{26}$ are each independently selected from H or $C_{1-6}$ alkyl), $C_{1-6}$ alkyl, $C_{6-12}$ aralkyl (e.g. $C_{7-12}$ aralkyl), $C_{6-12}$ aryl, $C_{1-6}$ alkoxy, $C_{6-12}$ aralkyloxy (e.g. $C_{7-12}$ aralkyloxy), $C_{6-12}$ aryloxy, 3 to 10 membered heterocycle, $C(O)R_{27}$ (wherein $R_{27}$ is selected from H, $C_{1-6}$ alkyl, $C_{6-12}$ aryl or 3 to 10 membered heterocycle), $C(O)OR_{28}$ (wherein $R_{28}$ is selected from H, $C_{1-6}$ alkyl, $C_{6-12}$ aryl, $C_{6-12}$ aralkyl (e.g. $C_{7-12}$ aralkyl) or 3 to 10 membered heterocycle), $NR_{29}C(O)R_{30}$, $NR_{29}C(O)OR_{30}$, $NR_{31}C(O)NR_{29}R_{30}$, $C(O)NR_{29}R_{30}$, $OC(O)NR_{29}R_{30}$ (wherein $R_{29}$, $R_{30}$ and $R_{31}$ are each independently selected from H, $C_{1-6}$ alkyl, $C_{6-12}$ aryl, $C_{6-12}$ aralkyl (e.g. $C_{7-12}$ aralkyl) or 3 to 10 membered heterocycle, or $R_{29}$ and $R_{30}$ are taken together with the atoms to which they are attached to form a 3 to 10 membered heterocycle), $SO_2NR_{32}R_{33}$, $NR_{32}SO_2R_{33}$ (wherein $R_{32}$ and $R_{33}$ are each independently selected from the group consisting of H, $C_{1-6}$ alkyl, $C_{6-12}$ aryl, 3 to 10 membered heterocycle and $C_{6-12}$ aralkyl (e.g. $C_{7-12}$ aralkyl)), $C(R_{34})NR_{35}$ or $C(R_{34})NOR_{35}$ (wherein $R_{34}$ and $R_{35}$ are each independently selected from the group consisting of H, $C_{1-6}$ alkyl, or $C_{6-12}$ aryl).

The term "urea" represents —$N(R_{36})CONR_{37}R_{38}$ wherein $R_{36}$ is H or $C_{1-6}$ alkyl and wherein $R_{37}$ and $R_{38}$ are each independently selected from the group consisting of H, $C_{1-6}$ alkyl, $C_{6-12}$ aryl, 3 to 10 membered heterocycle and $C_{6-12}$ aralkyl (e.g. $C_{7-12}$ aralkyl), or $R_{37}$ and $R_{38}$ are taken together with the nitrogen to which they are attached to form a 3 to 10 membered heterocycle.

"Oxidation levels": When there is a sulfur atom present, the sulfur atom can be at different oxidation levels, i.e. S, SO, or $SO_2$. All such oxidation levels are within the scope of the present invention. When there is a nitrogen atom present, the nitrogen atom can be at different oxidation levels, i.e. N or NO. All such oxidation levels are within the scope of the present invention.

There is also provided "pharmaceutically acceptable hydrates" of the compounds of the present invention. "Hydrates" exist when the compound of the invention incorporates water. The hydrate may contain one or more molecule of water per molecule of compound of the invention. Illustrative non-limiting examples include monohydrate, dihydrate, trihydrate and tetrahydrate. The hydrate may contain one or more molecule of compound of the invention per molecule of water. Illustrative non-limiting examples include semi-hydrate. In one embodiment, the water may be held in the crystal in various ways and thus, the water molecules may occupy lattice positions in the crystal, or they may form bonds with salts of the compounds as described herein. The hydrate must be "acceptable" in the sense of not being deleterious to the recipient thereof. The hydration may be assessed by methods known in the art such as Loss on Drying techniques (LOD) and Karl Fisher titration.

There is also provided "pharmaceutically acceptable salts" of the compounds of the present invention. By the term "pharmaceutically acceptable salts" of compounds are meant those derived from pharmaceutically acceptable inorganic and organic acids and bases. Examples of suitable acids include but are not limited to hydrochloric, hydrobromic, sulphuric, nitric, perchloric, fumaric, maleic, phosphoric, glycollic, lactic, salicylic, succinic, toleune-p-sulphonic, tartaric, acetic, trifluoroacetic, citric, methanesulphonic, formic, benzoic, malonic, naphthalene-2-sulphonic and benzenesulphonic acids. Other acids such as oxalic, while not in themselves pharmaceutically acceptable, may be useful as intermediates in obtaining the compounds of the invention and their pharmaceutically acceptable acid addition salts.

Salts derived from appropriate bases include alkali metal, alkaline earth metal or ammonium salts. The salt(s) must be "acceptable" in the sense of not being deleterious to the recipient thereof. Non-limiting examples of such salts known by those of ordinary skill in the art include without limitation calcium, potassium, sodium, choline, ethylenediamine, tromethamine, arginine, glycinelycine, lycine, magnesium and meglumine.

There is also provided a "pharmaceutically acceptable solvates" of the compounds of the present invention. The term "solvate" means that the compound of the invention incorporates one or more pharmaceutically acceptable solvent. The solvate may contain one or more molecule of solvent per molecule of compound of the invention or may contain one or more molecule of compound of the invention per molecule of solvent. In one embodiment, the solvent may be held in the crystal in various ways and thus, the solvent molecule may occupy lattice positions in the crystal, or they may form bonds with salts of the compounds as described herein. The solvate(s) must be "acceptable" in the sense of not being deleterious to the recipient thereof. The salvation may be assessed by methods known in the art such as Loss on Drying techniques (LOD).

Reference hereinafter to a compound according to the invention includes compounds of the general formula (I) and their pharmaceutically acceptable salts, hydrates and solvates.

"Polymorphs": It will be appreciated by those skilled in the art that the compounds in accordance with the present invention can exist in several different crystalline forms due to a different arrangement of molecules in the crystal lattice. This may include solvate or hydrate (also known as pseudopolymorphs) and amorphous forms. All such crystalline forms and polymorphs are included within the scope of the invention. The polymorphs may be characterized by methods well known in the art. Examples of analytical procedures that may be used to determine whether polymorphism occurs include: melting point (including hot-stage microscopy), infrared (not in solution), X-ray powder diffraction, thermal analysis methods (e.g. differential scanning calorimetry (DSC), differential thermal analysis (DTA), thermogravimetric analysis (TGA)), Raman spectroscopy, comparative intrinsic dissolution rate, scanning electron microscopy (SEM).

In one aspect, the present invention provides novel compounds including:

| CPD # | Name |
|---|---|
| 1 | 4,4-Difluoro-cyclohexanecarboxylic acid {(S)-3-[3-(4-methanesulfonyl-benzyl)-bicyclo[3.2.1]-2,4-dioxo-1β,3,8-triaza-spiro[4.5]dodec-8-yl]-1-phenyl-propyl}-amide; |
| 2 | 4,4-Difluoro-cyclohexanecarboxylic acid {(S)-3-[bicyclo[3.2.1]-2,4-dioxo-1α,3,8-triaza-spiro[4.5]dodec-8-yl]-1-phenyl-propyl}-amide; |
| 3 | 4,4-Difluoro-cyclohexanecarboxylic acid {(S)-3-[3-ethyl-bicyclo[3.2.1]-2,4-dioxo-1α,3,8-triaza-spiro[4.5]dodec-8-yl]-1-phenyl-propyl}-amide; |
| 4 | 4,4-Difluoro-cyclohexanecarboxylic acid {(S)-3-[1,3-diethyl-bicyclo[3.2.1]-2,4-dioxo-1α,3,8-triaza-spiro[4.5]dodec-8-yl]-1-phenyl-propyl}-amide; |
| 5 | 4,4-Difluoro-cyclohexanecarboxylic acid {(S)-3-[bicyclo[3.2.1]-2,4-dioxo-1β,3,8-triaza-spiro[4.5]dodec-8-yl]-1-phenyl-propyl}-amide; |
| 6 | 4,4-Difluoro-cyclohexanecarboxylic acid {(S)-3-[3-ethyl-bicyclo[3.2.1]-2,4-dioxo-1β,3,8-triaza-spiro[4.5]dodec-8-yl]-1-phenyl-propyl}-amide; |
| 7 | 4,4-Difluoro-cyclohexanecarboxylic acid {(S)-3-[1,3-diethyl-bicyclo[3.2.1]-2,4-dioxo-1β,3,8-triaza-spiro[4.5]dodec-8-yl]-1-phenyl-propyl}-amide; |
| 8 | 4,4-Difluoro-cyclohexanecarboxylic acid {(S)-3-[3-(4-dimethylsulfamoyl-benzyl)-bicyclo[3.2.1]-2,4-dioxo-1α,3,8-triaza-spiro[4.5]dodec-8-yl]-1-phenyl-propyl}-amide; |
| 9 | 4,4-Difluoro-cyclohexanecarboxylic acid {(S)-3-[3-(4-methanesulfonyl-benzyl)-bicyclo[3.2.1]-2,4-dioxo-1α,3,8-triaza-spiro[4.5]dodec-8-yl]-1-phenyl-propyl}-amide; |
| 10 | 4,4-Difluoro-cyclohexanecarboxylic acid {(S)-3-[1-ethyl-3-(4-methanesulfonyl-benzyl)-bicyclo[3.2.1]-2,4-dioxo-1β,3,8-triaza-spiro[4.5]dodec-8-yl]-1-phenyl-propyl}-amide; |
| 11 | 4,4-Difluoro-cyclohexanecarboxylic acid {(S)-3-[1,3-dimethyl-bicyclo[3.2.1]-2,4-dioxo-1β,3,8-triaza-spiro[4.5]dodec-8-yl]-1-phenyl-propyl}-amide; |
| 12 | 4,4-Difluoro-cyclohexanecarboxylic acid {(S)-3-[1-ethyl-3-methyl-bicyclo[3.2.1]-2,4-dioxo-1β,3,8-triaza-spiro[4.5]dodec-8-yl]-1-phenyl-propyl}-amide; |
| 13 | 4,4-Difluoro-cyclohexanecarboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide; |
| 14 | 4,4-Difluoro-cyclohexanecarboxylic acid {(S)-3-[1-propyl-3-methyl-bicyclo[3.2.1]-2,4-dioxo-1β,3,8-triaza-spiro[4.5]dodec-8-yl]-1-phenyl-propyl}-amide; |
| 15 | 4,4-Difluoro-cyclohexanecarboxylic acid {(S)-3-[1-isobutyl-3-methyl-bicyclo[3.2.1]-2,4-dioxo-1β,3,8-triaza-spiro[4.5]dodec-8-yl]-1-phenyl-propyl}-amide; |
| 16 | 4,4-Difluoro-cyclohexanecarboxylic acid {(S)-3-[1-cyclopropylmethyl-3-methyl-bicyclo[3.2.1]-2,4-dioxo-1β,3,8-triaza-spiro[4.5]dodec-8-yl]-1-phenyl-propyl}-amide; |
| 17 | 4,4-Difluoro-cyclohexanecarboxylic acid {(S)-3-[1-cyclohexylmethyl-3-methyl-bicyclo[3.2.1]-2,4-dioxo-1β,3,8-triaza-spiro[4.5]dodec-8-yl]-1-phenyl-propyl}-amide; |
| 18 | 4,4-Difluoro-cyclohexanecarboxylic acid {(S)-3-[1-benzyl-3-methyl-bicyclo[3.2.1]-2,4-dioxo-1β,3,8-triaza-spiro[4.5]dodec-8-yl]-1-phenyl-propyl}-amide; |

-continued

| CPD # | Name |
|---|---|
| 19 | 4,4-Difluoro-cyclohexanecarboxylic acid {(S)-3-[3-ethyl-1-methyl-bicyclo[3.2.1]-2,4-dioxo-1β,3,8-triaza-spiro[4.5]dodec-8-yl]-1-phenyl-propyl}-amide; |
| 20 | 4,4-Difluoro-cyclohexanecarboxylic acid {(S)-3-[3-ethyl-1-isopropyl-bicyclo[3.2.1]-2,4-dioxo-1β,3,8-triaza-spiro[4.5]dodec-8-yl]-1-phenyl-propyl}-amide; |
| 21 | 4,4-Difluoro-cyclohexanecarboxylic acid {(S)-3-[3-ethyl-1-propyl-bicyclo[3.2.1]-2,4-dioxo-1β,3,8-triaza-spiro[4.5]dodec-8-yl]-1-phenyl-propyl}-amide; |
| 22 | 4,4-Difluoro-cyclohexanecarboxylic acid {(S)-3-[3-ethyl-1-isobutyl-bicyclo[3.2.1]-2,4-dioxo-1β,3,8-triaza-spiro[4.5]dodec-8-yl]-1-phenyl-propyl}-amide; |
| 23 | 4,4-Difluoro-cyclohexanecarboxylic acid {(S)-3-[1-cyclopropylmethyl-3-ethyl-bicyclo[3.2.1]-2,4-dioxo-1β,3,8-triaza-spiro[4.5]dodec-8-yl]-1-phenyl-propyl}-amide; |
| 24 | 4,4-Difluoro-cyclohexanecarboxylic acid {(S)-3-[1-cyclohexylmethyl-3-ethyl-bicyclo[3.2.1]-2,4-dioxo-1β,3,8-triaza-spiro[4.5]dodec-8-yl]-1-phenyl-propyl}-amide; |
| 25 | 4,4-Difluoro-cyclohexanecarboxylic acid {(S)-3-[1-benzyl-3-ethyl-bicyclo[3.2.1]-2,4-dioxo-1β,3,8-triaza-spiro[4.5]dodec-8-yl]-1-phenyl-propyl}-amide; |
| 26 | 4,4-Difluoro-cyclohexanecarboxylic acid {(S)-3-[1-methyl-3-isopropyl-bicyclo[3.2.1]-2,4-dioxo-1β,3,8-triaza-spiro[4.5]dodec-8-yl]-1-phenyl-propyl}-amide; |
| 27 | 4,4-Difluoro-cyclohexanecarboxylic acid {(S)-3-[1-ethyl-3-isopropyl-bicyclo[3.2.1]-2,4-dioxo-1β,3,8-triaza-spiro[4.5]dodec-8-yl]-1-phenyl-propyl}-amide; |
| 28 | 4,4-Difluoro-cyclohexanecarboxylic acid {(S)-3-[1,3-diisopropyl-bicyclo[3.2.1]-2,4-dioxo-1β,3,8-triaza-spiro[4.5]dodec-8-yl]-1-phenyl-propyl}-amide; |
| 29 | 4,4-Difluoro-cyclohexanecarboxylic acid {(S)-3-[1-propyl-3-isopropyl-bicyclo[3.2.1]-2,4-dioxo-1β,3,8-triaza-spiro[4.5]dodec-8-yl]-1-phenyl-propyl}-amide; |
| 30 | 4,4-Difluoro-cyclohexanecarboxylic acid {(S)-3-[1-isobutyl-3-isopropyl-bicyclo[3.2.1]-2,4-dioxo-1β,3,8-triaza-spiro[4.5]dodec-8-yl]-1-phenyl-propyl}-amide; |
| 31 | 4,4-Difluoro-cyclohexanecarboxylic acid {(S)-3-[1-cyclopropylmethyl-3-isopropyl-bicyclo[3.2.1]-2,4-dioxo-1β,3,8-triaza-spiro[4.5]dodec-8-yl]-1-phenyl-propyl}-amide; |
| 32 | 4,4-Difluoro-cyclohexanecarboxylic acid {(S)-3-[1-cyclohexylmethyl-3-isopropyl-bicyclo[3.2.1]-2,4-dioxo-1β,3,8-triaza-spiro[4.5]dodec-8-yl]-1-phenyl-propyl}-amide; |
| 33 | 4,4-Difluoro-cyclohexanecarboxylic acid {(S)-3-[1-benzyl-3-isopropyl-bicyclo[3.2.1]-2,4-dioxo-1β,3,8-triaza-spiro[4.5]dodec-8-yl]-1-phenyl-propyl}-amide; |
| 34 | 4,4-Difluoro-cyclohexanecarboxylic acid {(S)-3-[1-methyl-3-benzyl-bicyclo[3.2.1]-2,4-dioxo-1β,3,8-triaza-spiro[4.5]dodec-8-yl]-1-phenyl-propyl}-amide; |
| 35 | 4,4-Difluoro-cyclohexanecarboxylic acid {(S)-3-[1-ethyl-3-benzyl-bicyclo[3.2.1]-2,4-dioxo-1β,3,8-triaza-spiro[4.5]dodec-8-yl]-1-phenyl-propyl}-amide; |
| 36 | 4,4-Difluoro-cyclohexanecarboxylic acid {(S)-3-[1-propyl-3-benzyl-bicyclo[3.2.1]-2,4-dioxo-1β,3,8-triaza-spiro[4.5]dodec-8-yl]-1-phenyl-propyl}-amide; |
| 37 | 4,4-Difluoro-cyclohexanecarboxylic acid {(S)-3-[1-cyclopropylmethyl-3-benzyl-bicyclo[3.2.1]-2,4-dioxo-1β,3,8-triaza-spiro[4.5]dodec-8-yl]-1-phenyl-propyl}-amide; |
| 38 | 4,4-Difluoro-cyclohexanecarboxylic acid {(S)-3-[1-isopropyl-3-benzyl-bicyclo[3.2.1]-2,4-dioxo-1β,3,8-triaza-spiro[4.5]dodec-8-yl]-1-phenyl-propyl}-amide; |
| 39 | 4,4-Difluoro-cyclohexanecarboxylic acid {(S)-3-[1,3-diethyl-bicyclo[3.2.1]-2-oxo-1β,3,8-triaza-spiro[4.5]dodec-8-yl]-1-phenyl-propyl}-amide; |
| 40 | 4,4-Difluoro-cyclohexanecarboxylic acid {(S)-3-[1-isobutyl-3-methyl-bicyclo[3.2.1]-2-oxo-1β,3,8-triaza-spiro[4.5]dodec-8-yl]-1-phenyl-propyl}-amide; |
| 41 | 4,4-Difluoro-cyclohexanecarboxylic acid {(S)-3-[1-cyclopropylmethyl-3-methyl-bicyclo[3.2.1]-2-oxo-1β,3,8-triaza-spiro[4.5]dodec-8-yl]-1-phenyl-propyl}-amide; |
| 42 | 4,4-Difluoro-cyclohexanecarboxylic acid {(S)-3-[1-(2-methoxyethyl)-3-methyl-bicyclo[3.2.1]-2,4-dioxo-1β,3,8-triaza-spiro[4.5]dodec-8-yl]-1-phenyl-propyl}-amide; |
| 43 | 4,4-Difluoro-cyclohexanecarboxylic acid {(S)-3-[1-isopropyl-3-benzyl-bicyclo[3.2.1]-2-oxo-1β,3,8-triaza-spiro[4.5]dodec-8-yl]-1-phenyl-propyl}-amide; |
| 44 | 4,4-Difluoro-cyclohexanecarboxylic acid {(S)-3-[1-isobutyl-3-benzyl-bicyclo[3.2.1]-2-oxo-1β,3,8-triaza-spiro[4.5]dodec-8-yl]-1-phenyl-propyl}-amide; |

-continued

| CPD # | Name |
|---|---|
| 45 | 4,4-Difluoro-cyclohexanecarboxylic acid {(S)-3-[1-isopropyl-3-methyl-bicyclo[3.2.1]-2-oxo-1β,3,8-triaza-spiro[4.5]dodec-8-yl]-1-phenyl-propyl}-amide; |
| 46 | 4,4-Difluoro-cyclohexanecarboxylic acid {(S)-3-[1-cyclohexyl-3-methyl-bicyclo[3.2.1]-2,4-dioxo-1β,3,8-triaza-spiro[4.5]dodec-8-yl]-1-phenyl-propyl}-amide; |
| 47 | 4,4-Difluoro-cyclohexanecarboxylic acid {(S)-3-[1-isobutyl-3-ethyl-bicyclo[3.2.1]-2-oxo-1β,3,8-triaza-spiro[4.5]dodec-8-yl]-1-phenyl-propyl}-amide; |
| 48 | 4,4-Difluoro-cyclohexanecarboxylic acid {(S)-3-[3-isobutyl-bicyclo[3.2.1]-2,4-dioxo-1α,3,8-triaza-spiro[4.5]dodec-8-yl]-1-phenyl-propyl}-amide; |
| 49 | 4,4-Difluoro-cyclohexanecarboxylic acid {(S)-3-[1-ethyl-bicyclo[3.2.1]-2,4-dioxo-1β,3,8-triaza-spiro[4.5]dodec-8-yl]-1-phenyl-propyl}-amide; |
| 50 | 4,4-Difluoro-cyclohexanecarboxylic acid {(S)-3-[1-isopropyl-bicyclo[3.2.1]-2,4-dioxo-1β,3,8-triaza-spiro[4.5]dodec-8-yl]-1-phenyl-propyl}-amide; |
| 51 | 4,4-Difluoro-cyclohexanecarboxylic acid {(S)-3-[1-isobutyl-bicyclo[3.2.1]-2,4-dioxo-1β,3,8-triaza-spiro[4.5]dodec-8-yl]-1-phenyl-propyl}-amide; |
| 52 | 4,4-Difluoro-cyclohexanecarboxylic acid {(S)-3-[3-methyl-1-((S)-2-methyl-butyl)-bicyclo[3.2.1]-2,4-dioxo-1β,3,8-triaza-spiro[4.5]dodec-8-yl]-1-phenyl-propyl}-amide; |
| 53 | 4,4-Difluoro-cyclohexanecarboxylic acid {(S)-3-[3-cyclopropyl-1-isopropyl-bicyclo[3.2.1]-2,4-dioxo-1β,3,8-triaza-spiro[4.5]dodec-8-yl]-1-phenyl-propyl}-amide; |
| 54 | 4,4-Difluoro-cyclohexanecarboxylic acid {(S)-3-[1-isopropyl-3-(2-methoxy-ethyl)-bicyclo[3.2.1]-2,4-dioxo-1β,3,8-triaza-spiro[4.5]dodec-8-yl]-1-phenyl-propyl}-amide; |
| 55 | 4,4-Difluoro-cyclohexanecarboxylic acid {(S)-3-[3-cyanomethyl-1-isopropyl-bicyclo[3.2.1]-2,4-dioxo-1β,3,8-triaza-spiro[4.5]dodec-8-yl]-1-phenyl-propyl}-amide; |
| 56 | 4,4-Difluoro-cyclohexanecarboxylic acid {(S)-3-[1,3-diisobutyl-bicyclo[3.2.1]-2,4-dioxo-1β,3,8-triaza-spiro[4.5]dodec-8-yl]-1-phenyl-propyl}-amide; |
| 57 | 4,4-Difluoro-cyclohexanecarboxylic acid {(S)-3-[3-cyclopropylmethyl-1-isopropyl-bicyclo[3.2.1]-2,4-dioxo-1β,3,8-triaza-spiro[4.5]dodec-8-yl]-1-phenyl-propyl}-amide; |
| 58 | 4,4-Difluoro-cyclohexanecarboxylic acid {(S)-3-[1-isopropyl-3-phenyl-bicyclo[3.2.1]-2,4-dioxo-1β,3,8-triaza-spiro[4.5]dodec-8-yl]-1-phenyl-propyl}-amide; |
| 59 | 4,4-Difluoro-cyclohexanecarboxylic acid {(S)-3-[1-isopropyl-3-pyridin-3-yl-bicyclo[3.2.1]-2,4-dioxo-1β,3,8-triaza-spiro[4.5]dodec-8-yl]-1-phenyl-propyl}-amide; |
| 60 | 4,4-Difluoro-cyclohexanecarboxylic acid {(S)-3-[1-isopropyl-3-pyridin-4-yl-bicyclo[3.2.1]-2,4-dioxo-1β,3,8-triaza-spiro[4.5]dodec-8-yl]-1-phenyl-propyl}-amide; |
| 61 | 4,4-Difluoro-cyclohexanecarboxylic acid {(S)-3-[1-isopropyl-3-(tetrahydro-furan-3-yl)-bicyclo[3.2.1]-2,4-dioxo-1β,3,8-triaza-spiro[4.5]dodec-8-yl]-1-phenyl-propyl}-amide; |
| 62 | 4,4-Difluoro-cyclohexanecarboxylic acid {(S)-3-[1-isopropyl-3-(tetrahydro-pyran-4-yl)-bicyclo[3.2.1]-2,4-dioxo-1β,3,8-triaza-spiro[4.5]dodec-8-yl]-1-phenyl-propyl}-amide; |
| 63 | 4,4-Difluoro-cyclohexanecarboxylic acid {(S)-3-[3-ethyl-1-isopropyl-bicyclo[3.2.1]-2-oxo-1β,3,8-triaza-spiro[4.5]dodec-8-yl]-1-phenyl-propyl}-amide; |
| 64 | 4,4-Difluoro-cyclohexanecarboxylic acid {(S)-3-[1-cyclopropylmethyl-3-methyl-bicyclo[3.2.1]-2-oxo-1β,3,8-triaza-spiro[4.5]dodec-8-yl]-1-phenyl-propyl}-amide; |
| 65 | 4,4-Difluoro-cyclohexanecarboxylic acid {(S)-3-[3-cyclopropylmethyl-1-isopropyl-bicyclo[3.2.1]-2-oxo-1β,3,8-triaza-spiro[4.5]dodec-8-yl]-1-phenyl-propyl}-amide; |
| 66 | 4,4-Difluoro-cyclohexanecarboxylic acid {(S)-3-[3-(2-hydroxy-ethyl)-1-isopropyl-bicyclo[3.2.1]-2-oxo-1β,3,8-triaza-spiro[4.5]dodec-8-yl]-1-phenyl-propyl}-amide; |
| 67 | 4,4-Difluoro-cyclohexanecarboxylic acid {(S)-3-[1-isopropyl-3-(2-methoxy-ethyl)-bicyclo[3.2.1]-2-oxo-1β,3,8-triaza-spiro[4.5]dodec-8-yl]-1-phenyl-propyl}-amide; |
| 68 | 4,4-Difluoro-cyclohexanecarboxylic acid {(S)-3-[3-(2-ethoxy-ethyl)-1-isopropyl-bicyclo[3.2.1]-2-oxo-1β,3,8-triaza-spiro[4.5]dodec-8-yl]-1-phenyl-propyl}-amide; |
| 69 | 4,4-Difluoro-cyclohexanecarboxylic acid {(S)-3-[1-isobutyl-3-(2-methoxy-ethyl)-bicyclo[3.2.1]-2-oxo-1β,3,8-triaza-spiro[4.5]dodec-8-yl]-1-phenyl-propyl}-amide; |
| 70 | 4,4-Difluoro-cyclohexanecarboxylic acid {(S)-3-[1-isopropyl-3-phenyl-bicyclo[3.2.1]-2-oxo-1β,3,8-triaza-spiro[4.5]dodec-8-yl]-1-phenyl-propyl}-amide; |
| 71 | 4,4-Difluoro-cyclohexanecarboxylic acid {(S)-3-[1-isopropyl-3-(tetrahydro-furan-3-yl)-bicyclo[3.2.1]-2-oxo-1β,3,8-triaza-spiro[4.5]dodec-8-yl]-1-phenyl-propyl}-amide; |

| CPD # | Name |
|---|---|
| 72 | 4,4-Difluoro-cyclohexanecarboxylic acid {(S)-3-[1-isopropyl-3-(tetrahydro-pyran-4-yl)-bicyclo[3.2.1]-2-oxo-1β,3,8-triaza-spiro[4.5]dodec-8-yl]-1-phenyl-propyl}-amide; |
| 73 | (S)-1-(3-Fluoro-phenyl)-{3-[1-isopropyl-3-methyl-bicyclo[3.2.1]-2,4-dioxo-1β,3,8-triaza-spiro[4.5]dodec-8-yl]-propyl}-carbamic acid tert-butyl ester; |
| 74 | 8-[(S)-3-Amino-3-(3-fluoro-phenyl)-propyl]-1-isopropyl-3-methyl-bicyclo[3.2.1]-1β,3,8-triaza-spiro[4.5]dodecane-2,4-dione; |
| 75 | {(S)-3-[1-Isopropyl-3-methyl-bicyclo[3.2.1]-2,4-dioxo-1β,3,8-triaza-spiro[4.5]dodec-8-yl]-1-phenyl-propyl}-carbamic acid tert-butyl ester; |
| 76 | 8-[(S)-3-Amino-3-phenyl-propyl]-1-isopropyl-3-methyl-bicyclo[3.2.1]-1β,3,8-triaza-spiro[4.5]dodecane-2,4-dione; |
| 77 | N-(S)-1-(3-Fluoro-phenyl)-{3-[1-isopropyl-3-methyl-bicyclo[3.2.1]-2,4-dioxo-1β,3,8-triaza-spiro[4.5]dodec-8-yl]-propyl}-isobutyramide; |
| 78 | Cyclobutanecarboxylic acid-(S)-1-(3-fluoro-phenyl)-{3-[1-isopropyl-3-methyl-bicyclo[3.2.1]-2,4-dioxo-1β,3,8-triaza-spiro[4.5]dodec-8-yl]-propyl}-amide; |
| 79 | (S)-1-(3-Fluoro-phenyl)-{3-[1-isopropyl-3-methyl-bicyclo[3.2.1]-2,4-dioxo-1β,3,8-triaza-spiro[4.5]dodec-8-yl]-propyl}-acetamide; |
| 80 | 4-Methyl-cyclohexanecarboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide; |
| 81 | Cyclopentanecarboxylic acid-(S)-1-(3-fluoro-phenyl)-{3-[1-isopropyl-3-methyl-bicyclo[3.2.1]-2,4-dioxo-1β,3,8-triaza-spiro[4.5]dodec-8-yl]-propyl}-amide; |
| 82 | Cyclohexanecarboxylic acid-(S)-1-(3-fluoro-phenyl)-{3-[1-isopropyl-3-methyl-bicyclo[3.2.1]-2,4-dioxo-1β,3,8-triaza-spiro[4.5]dodec-8-yl]-propyl}-amide; |
| 83 | 4-Methyl-cyclohexanecarboxylic acid-(S)-1-(3-fluoro-phenyl)-{3-[1-isopropyl-3-methyl-bicyclo[3.2.1]-2,4-dioxo-1β,3,8-triaza-spiro[4.5]dodec-8-yl]-propyl}-amide; |
| 84 | N-{(S)-3-[1-Isopropyl-3-methyl-bicyclo[3.2.1]-2,4-dioxo-1β,3,8-triaza-spiro[4.5]dodec-8-yl]-1-phenyl-propyl}-acetamide; |
| 85 | N-{(S)-3-[1-Isopropyl-3-methyl-bicyclo[3.2.1]-2,4-dioxo-1β,3,8-triaza-spiro[4.5]dodec-8-yl]-1-phenyl-propyl}-isobutyramide; |
| 86 | Cyclobutanecarboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide; |
| 87 | Cyclopentanecarboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide; |
| 88 | Cyclohexanecarboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide; |
| 89 | Cyclopropanecarboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide; |
| 90 | N-{(S)-3-[1-Isopropyl-3-methyl-bicyclo[3.2.1]-2,4-dioxo-1β,3,8-triaza-spiro[4.5]dodec-8-yl]-1-phenyl-propyl}-3,3-dimethyl-butyramide; |
| 91 | 2-Cyclopropyl-N-{(S)-3-[1-isopropyl-3-methyl-bicyclo[3.2.1]-2,4-dioxo-1β,3,8-triaza-spiro[4.5]dodec-8-yl]-1-phenyl-propyl}-acetamide; |
| 92 | Tetrahydro-pyran-4-carboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide; |
| 93 | N-{(S)-3-[1-Isopropyl-3-methyl-bicyclo[3.2.1]-2,4-dioxo-1β,3,8-triaza-spiro[4.5]dodec-8-yl]-1-phenyl-propyl}-2,2-dimethyl-propionamide; |
| 94 | (S)-1-Acetyl-piperidine-3-carboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide; |
| 95 | Tetrahydro-pyran-3-carboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide; |
| 96 | 4-Methoxy-cyclohexanecarboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide; |
| 97 | 4-Trifluoromethyl-cyclohexanecarboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide; |
| 98 | 4,4-Difluoro-cyclohexanecarboxylic acid {(S)-3-[1-isopropyl-3-(2-methoxy-propyl)-bicyclo[3.2.1]-2,4-dioxo-1β,3,8-triaza-spiro[4.5]dodec-8-yl]-1-phenyl-propyl}-amide; |
| 99 | 4,4-Difluoro-cyclohexanecarboxylic acid {(S)-3-[1-isopropyl-3-(2-methoxy-propyl)-bicyclo[3.2.1]-2-oxo-1β,3,8-triaza-spiro[4.5]dodec-8-yl]-1-phenyl-propyl}-amide; |
| 100 | 4,4-Difluoro-cyclohexanecarboxylic acid {(S)-3-[1-isopropyl-3-oxetan-2-ylmethyl-bicyclo[3.2.1]-2,4-dioxo-1β,3,8-triaza-spiro[4.5]dodec-8-yl]-1-phenyl-propyl}-amide; |
| 101 | 4,4-Difluoro-cyclohexanecarboxylic acid {(S)-3-[1-isopropyl-3-oxetan-2-ylmethyl-bicyclo[3.2.1]-2-oxo-1β,3,8-triaza-spiro[4.5]dodec-8-yl]-1-phenyl-propyl}-amide; |
| 102 | 4,4-Difluoro-cyclohexanecarboxylic acid {(S)-3-[1-isopropyl-3-oxetan-3-ylmethyl-bicyclo[3.2.1]-2,4-dioxo-1β,3,8-triaza-spiro[4.5]dodec-8-yl]-1-phenyl-propyl}-amide; |

| CPD # | Name |
|---|---|
| 103 | 4,4-Difluoro-cyclohexanecarboxylic acid {(S)-3-[1-isopropyl-3-oxetan-3-ylmethyl-bicyclo[3.2.1]-2-oxo-1β,3,8-triaza-spiro[4.5]dodec-8-yl]-1-phenyl-propyl}-amide; |
| 104 | 4,4-Difluoro-cyclohexanecarboxylic acid {(S)-3-[1-isopropyl-3-(tetrahydro-furan-2-ylmethyl)-bicyclo[3.2.1]-2,4-dioxo-1β,3,8-triaza-spiro[4.5]dodec-8-yl]-1-phenyl-propyl}-amide; |
| 105 | 4,4-Difluoro-cyclohexanecarboxylic acid {(S)-3-[1-isopropyl-3-(tetrahydro-furan-2-ylmethyl)-bicyclo[3.2.1]-2-oxo-1β,3,8-triaza-spiro[4.5]dodec-8-yl]-1-phenyl-propyl}-amide; |
| 106 | 4,4-Difluoro-cyclohexanecarboxylic acid {(S)-3-[1-isopropyl-3-(tetrahydro-furan-3-ylmethyl)-bicyclo[3.2.1]-2,4-dioxo-1β,3,8-triaza-spiro[4.5]dodec-8-yl]-1-phenyl-propyl}-amide; |
| 107 | 4,4-Difluoro-cyclohexanecarboxylicacid {(S)-3-[1-isopropyl-3-(tetrahydro-furan-3-ylmethyl)-bicyclo[3.2.1]-2-oxo-1β,3,8-triaza-spiro[4.5]dodec-8-yl]-1-phenyl-propyl}-amide; |
| 108 | 4,4-Difluoro-cyclohexanecarboxylic acid {(S)-3-[1-isopropyl-3-(tetrahydro-pyran-2-ylmethyl)-bicyclo[3.2.1]-2,4-dioxo-1β,3,8-triaza-spiro[4.5]dodec-8-yl]-1-phenyl-propyl}-amide; |
| 109 | 4,4-Difluoro-cyclohexanecarboxylic acid {(S)-3-[1-isopropyl-3-(tetrahydro-pyran-2-ylmethyl)-bicyclo[3.2.1]-2-oxo-1β,3,8-triaza-spiro[4.5]dodec-8-yl]-1-phenyl-propyl}-amide; |
| 110 | 4,4-Difluoro-cyclohexanecarboxylic acid {(S)-3-[1-isopropyl-3-(tetrahydro-pyran-3-ylmethyl)-bicyclo[3.2.1]-2,4-dioxo-1β,3,8-triaza-spiro[4.5]dodec-8-yl]-1-phenyl-propyl}-amide; |
| 111 | 4,4-Difluoro-cyclohexanecarboxylic acid {(S)-3-[1-isopropyl-3-(tetrahydro-pyran-3-ylmethyl)-bicyclo[3.2.1]-2-oxo-1β,3,8-triaza-spiro[4.5]dodec-8-yl]-1-phenyl-propyl}-amide; |
| 112 | 4,4-Difluoro-cyclohexanecarboxylic acid {(S)-3-[1-isopropyl-3-(tetrahydro-pyran-4-ylmethyl)-bicyclo[3.2.1]-2,4-dioxo-1β,3,8-triaza-spiro[4.5]dodec-8-yl]-1-phenyl-propyl}-amide; |
| 113 | 4,4-Difluoro-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide; | and pharmaceutically acceptable salts, hydrates or solvates thereof.

It will be appreciated that the amount of a compound of the invention required for use in treatment will vary not only with the particular compound selected but also with the route of administration, the nature of the condition for which treatment is required and the age and condition of the patient and will be ultimately at the discretion of the attendant physician or veterinarian. In general however a suitable dose will be in the range of from about 0.1 to about 750 mg/kg of body weight per day, preferably in the range of 0.5 to 60 mg/kg/day, most preferably in the range of 1 to 20 mg/kg/day.

The desired dose may conveniently be presented in a single dose or as divided dose administered at appropriate intervals, for example as two, three, four or more doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to about 75 µM, preferably about 2 to 50 µM, most preferably about 3 to about 30 µM. This may be achieved, for example, by the intravenous injection of a 0.1 to 5% solution of the active ingredient, optionally in saline, or orally administered as a bolus containing about 1 to about 500 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible that, for use in therapy, a compound of the invention may be administered as the raw chemical it is preferable to present the active ingredient as a pharmaceutical formulation. The invention thus further provides a pharmaceutical formulation comprising a compound of formula (I) or a pharmaceutically acceptable derivative thereof together with one or more pharmaceutically acceptable carriers therefore and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), transdermal, vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulation suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

For topical administration to the epidermis, the compounds according to the invention may be formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops. Drops may be formulated with an aqueous or non-aqueous base also comprising one more dispersing agents, solubilising agents or suspending agents. Liquid sprays are conveniently delivered from pressurized packs.

For administration by inhalation the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

When desired the above described formulations adapted to give sustained release of the active ingredient may be employed.

When the compound (I) or a pharmaceutically acceptable salt, hydrate or solvate thereof is used in combination with a second therapeutic active agent, the dose of each compound may be either the same as or different from that when the compound is used alone. Conventional doses and regimens are readily appreciated by those skilled in the art, including doses described in the Physicians Desk Reference, $56^{th}$ edition, 2002.

The present invention is directed to the use of the compounds as modulators of CCR5 chemokine receptor activity. In particular, the compounds of the invention have been found to have activity in binding to the CCR5 receptor in the biological assay, as described in Example 7, generally with an $IC_{50}$ value of less than 25 µM. The terms "modulator" or "modulation" are meant to include antagonism, agonism, mixed and partial antagonism and agonism.

Certain compounds of the present invention have also been tested in an assay for HIV activity, as described in Example 7, and generally having an $IC_{50}$ value of less than 1 µM.

The purity and mass of the following examples were characterized by mass spectra (LC/MS) and or NMR spectra.

In the foregoing and in the following examples, all temperatures are set forth uncorrected in degrees Celsius; and, unless otherwise indicated, all parts and percentages are by weight.

The entire disclosures of all applications, patents and publications, cited above and below, are hereby incorporated by reference.

The following general schemes and examples are provided to illustrate various embodiments of the present invention and shall not be considered as limiting in scope.

The synthetic method described in Preparation 2 was employed in an attempt to make compound 4. This attempt was not successful. However, one of ordinary skill in the art will recognize alternative reaction schemes using conventional chemical procedures for preparing compounds like compound 4 in which the nitrogen in the α position relative to the spirotropane ring is substituted.

The following abbreviations may be used as follows:

br broad

DCE 1,2-dichloroethane

DCM dichloromethane

DIPEA N,N-diisopropylethylamine

DMF N,N-dimethylformamide

LAH lithium aluminium hydride

Sept. septuplet

TFA trifluoroacetic acid

THF tetrahydrofuran

Semi-preparative HPLC purification procedures:

Column: Waters Symmetry Shield RP18, 5 microns, 19×100 mm

Buffer A: 3 mM HCl in $H_2O$ (pH 2.4-2.6)

Buffer B: acetonitrile

Method A: 20% B to 45% B in 30 min.

Method B: 10% B to 30% B in 20 min.

Scheme 1

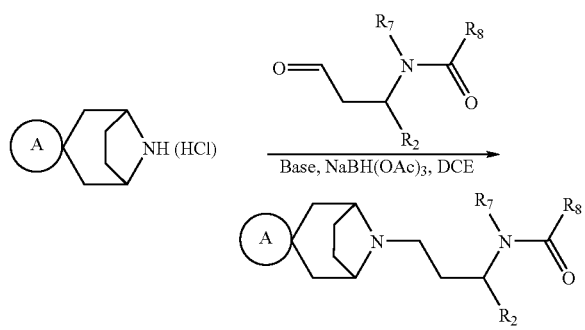

PREPARATION 1

3-(4-Methanesulfonylbenzyl)-bicyclo[3.2.1]-1α,3,8-triaza-spiro[4.5]dodecan-2,4-dione hydrochloride

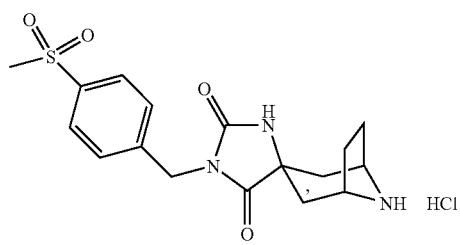

Step 1: A solution of Boc-nortropinone (2 g, 8.9 mmol), potassium cyanide (0.64 g, 9.8 mmol) and ammonium carbonate (2.6 g, 28 mmol) in ethanol (13 mL) and water (10 mL) was agitated for 2 days at room temperature. The mixture was filtered off and the precipitated solid washed with water. After overnight drying in vacuo, 1.21 g (46%) of bicyclo[3.2.1]-1α,3,8-triaza-spiro[4.5]dodecan-2,4-dione-8-carboxylic acid tert-butyl ester was isolated.

$^1$H NMR (400 MHz, DMSO-d$_6$): δ [ppm] 10.77 (s, 1H), 8.35 (s, 1H), 4.05 (s, 2H), 2.11-2.05 (m, 2H), 1.97-1.88 (m, 4H), 1.58-1.50 (m, 2H), 1.42 (s, 9H).

Step 2: To 0.15 g (0.5 mmol) of bicyclo[3.2.1]-1α,3,8-triaza-spiro[4.5]dodecan-2,4-dione-8-carboxylic acid tert-butyl ester were added successively 96 mg (0.56 mmol) of 4-methylthiobenzyl chloride, 70 mg (0.5 mmol) of potassium carbonate and 2.5 mL of anhydrous DMF. The reaction mixture was stirred overnight at room temperature. Then water was added and a white precipitated solid was collected by filtration. This crude material was back washed with water, hexanes and diethyl ether and dried under reduced pressure yielding 0.15 g (70%) of 3-(4-methylsulfanylbenzyl)-bicyclo[3.2.1]-1α,3,8-triaza-spiro[4.5]dodecan-2,4-dione-8-carboxylic acid tert-butyl ester as a white solid.

$^1$H NMR (400 MHz, DMSO-d$_6$) : δ [ppm] 8.77 (s, 1H), 7.19 (d, 2H), 7.13 (d, 2H), 4.45 (s, 2H), 4.05 (s, 2H), 2.43 (s, 3H), 2.15-2.05 (m, 2H), 2.00-1.86 (m, 4H), 1.61-1.50 (m, 2H), 1.39 (s, 9H).

Step 3: To a solution of 0.15 g (0.35 mmol) of 3-(4-methylsulfanylbenzyl)-bicyclo[3.2.1]-1α,3,8-triaza-spiro[4.5]dodecan-2,4-dione-8-carboxylic acid tert-butyl ester in 2.3 mL of THF, was added 0.32 g (0.52 mmol) of Oxone® in 2.3 mL of water. The reaction mixture was agitated overnight at room temperature. An aqueous solution of sodium hydroxide (1N, 10 mL) was added and the solution was extracted with DCM (2×20 mL). The combined organic layers were dried (Na$_2$SO$_4$), filtered and evaporated under reduced pressure to yield 0.12 g (75%) of 3-(4-methanesulfonylbenzyl)-bicyclo[3.2.1]-1α,3,8-triaza-spiro[4.5]dodecan-2,4-dione-8-carboxylic acid tert-butyl ester as an off white foam.

$^1$H NMR (400 MHz, DMSO-d$_6$): δ [ppm] 8.84 (s, 1H), 7.87 (d, 2H), 7.43 (d, 2H), 4.62 (s, 2H), 4.07 (s, 2H), 3.18 (s, 3H), 2.22-2.12 (m, 2H), 2.00-1.88 (m, 4H), 1.67-1.55 (m, 2H), 1.39 (s, 9H).

Step 4: To 0.12 g (0.26 mmol) of 3-(4-methanesulfonylbenzyl)-bicyclo[3.2.1]-1α,3,8-triaza-spiro[4.5]dodecan-2,4-dione-8-carboxylic acid tert-butyl ester was added 0.5 mL of dioxane and 0.5 mL of 4N solution of dioxane/HCl. The reaction mixture was stirred for 5 hours at room temperature and concentrated in vacuo. The crude was dissolved in diethyl ether to obtain, after filtration, the 3-(4-methanesulfonylbenzyl)-bicyclo[3.2.1]-1α,3,8-triaza-spiro[4.5]dodecan-2,4-dione hydrochloride as a white solid (90 mg, 87%).

$^1$H NMR (400 MHz, DMSO-d$_6$): δ [ppm] 9.27 (br s, 1H), 8.90 (s, 1H), 8.73 (br d, 1H), 7.87 (d, 2H), 7.46 (d, 2H), 4.65 (s, 2H), 4.02 (s, 2H), 3.19 (s, 3H), 2.35 (d×d, 2H), 2.22-2.18 (m, 2H), 2.00-1.92 (m, 4H).

PREPARATION 2

1,3-diethyl-bicyclo[3.2.1]-1β,3,8-triaza-spiro[4.5]dodecan-2,4-dione

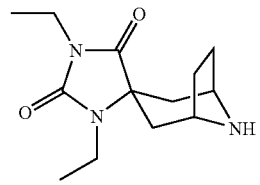

Step 1: To 15.4 g (72 mmol) of 8-benzyl-8-aza-bicyclo[3.2.1]octan-3-one previously dissolved in 60 mL of ethanol was added successively 4 g (75 mmol) of ammonium chloride, 5.4 g (83 mmol) of potassium cyanide and 45 mL of water. The reaction mixture was agitated for 8 days at room temperature and then concentrated to remove ethanol. The aqueous layer was extracted with diethyl ether and dried over sodium sulfate. Hydrogen chloride was passed into the solution causing the 3β-amino-8-benzyl-8-aza-bicyclo[3.2.1]octane-3-carbonitrile dihydrochloride to be precipitating as a brown solid (19.9 g).

Step 2: To 19.3 g (61.4 mmol) of 3β-amino-8-benzyl-8-aza-bicyclo[3.2.1]octane-3-carbonitrile dihydrochloride previously dissolved in 360 mL of acetic acid was added 29 g (357 mmol) of potassium cyanate and 180 mL of water. The reaction mixture was heated at 110° C. for 45 minutes and then. cooled to room temperature. 180 mL of concentrated aqueous hydrochloride solution was added and the reaction was refluxed for 50 minutes, cooled to room temperature and concentrated in vacuo. The residue was neutralized with a saturated solution of bicarbonate and extracted with ethyl acetate. Organic layers were washed back with water, brine and then dried over sodium sulfate. The crude mixture was purified by flash chromatography (hexanes/ethyl acetate 50 to 100% then DCM/MeOH 5 to 20%) to yield 5.5 g (26.6%, steps 1 and 2) of 8-benzyl-bicyclo[3.2.1]-2,4-dioxo-1β,3,8-triaza-spiro[4.5]dodecane as a pale brown foam.

$^1$H NMR (400 MHz, DMSO-d$_6$) : δ [ppm] 10.39 (s, 1H), 7.78 (s, 1H), 7.37-7.19 (m, 5H), 3.53 (s, 2H), 3.15-3.12 (m, 2H), 1.97-1.89 (m, 6H), 1.74 (d, 2H).

Step 3: To 1.56 g (5.48 mmol) of 8-benzyl-bicyclo[3.2.1]-2,4-dioxo-1β,3,8-triaza-spiro[4.5]dodecane previously dissolved in 17 mL of anhydrous DMF was added 1.09 g (7.94 mmol) of potassium carbonate and 1.23 g (7.94 mmol) of iodoethane. The reaction mixture was agitated overnight at room temperature and water was added. The solution was extracted with diethyl ether and dried over sodium sulfate to yield 1.67 g (97.6%) of 8-benzyl-3-ethyl-bicyclo[3.2.1]-1β,3,8-triaza-spiro[4.5]dodecan-2,4-dione as an orange oil.

$^1$H NMR (400 MHz, DMSO-d$_6$): δ [ppm] 8.05 (s, 1H), 7.40-7.18 (m, 5H), 3.53 (s, 2H), 3.38-3.24 (m, 2H), 3.06 (s, 2H), 2.05-1.85 (m, 6H), 1.77-1.70 (m, 2H), 1.00 (t, 3H).

Step 4: To 60 mg (0.19 mmol) of 8-benzyl-3-ethyl-bicyclo[3.2.1]-1β,3,8-triaza-spiro[4.5]dodecan-2,4-dione previously dissolved in 1 mL of anhydrous DMF was added 40 mg (0.3 mmol) of sodium hydride (60% dispersion in mineral oil). The reaction mixture was agitated for 15 minutes at room temperature before adding 18 μL (0.21 mmol) of iodoethane. After overnight agitation, water was added and the solution was extracted with diethyl ether. The organic layers were washed with water, brine and dried over sodium sulfate. The crude was purified by Bond Elut (hexanes/ethyl acetate 0 to 100%) to yield 56 mg (86.4%) of 8-benzyl-1,3-diethyl-bicyclo[3.2.1]-1β,3,8-triaza-spiro[4.5]dodecan-2,4-dione.

$^1$H NMR (400 MHz, DMSO-d$_6$): δ [ppm] 7.37-7.21 (m, 5H), 3.48 (s, 2H), 3.35-3.23 (m, 4H), 3.18 (s, 2H), 2.05-1.93 (m, 6H), 1.74-1.71 (m, 2H), 1.21 (t, 3H), 1.03 (t, 3H).

Step 5: To 50 mg (0.15 mmol) of 8-benzyl-1,3-diethyl-bicyclo[3.2.1]-1β,3,8-triaza-spiro[4.5]dodecan-2,4-dione previously dissolved in 1.7 mL of ethanol was added 92 mg (1.5 mmol) of ammonium formate and 20.9 mg (0.015 mmol) of palladium hydroxide. The reaction mixture was refluxed for 1 hour, cooled to room temperature and filtered over celite yielding 35 mg (93%) of 1,3-diethyl-bicyclo[3.2.1]-1β,3,8-triaza-spiro[4.5]dodecan-2,4-dione as a brownish oil. $^1$H NMR (400 MHz, DMSO-d$_6$): δ [ppm] 3.44 (s, 2H), 3.35-3.21 (m, 4H), 2.04-2.01 (m, 2H), 1.82-1.78 (m, 2H), 1.65-1.58 (m, 4H), 1.14 (t, 3H), 1.02 (t, 3H).

PREPARATION 3

1,3-Diethyl-bicyclo[3.2.1]-1β,3,8-triaza-spiro[4.5]dodecan-2-one

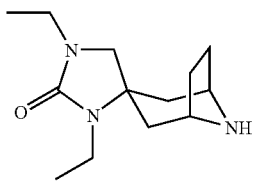

Step 1: To 230 mg (0.67 mmol) of 8-benzyl-1,3-diethyl-bicyclo[3.2.1]-1β,3,8-triaza-spiro[4.5]dodecan-2,4-dione previously dissolved in 5 mL of anhydrous THF was added at 0° C. 680 μL (0.68 mmol) of 1M lithium aluminium hydride in THF under nitrogen. The solution was then warmed to room temperature and stirred overnight. The reaction was quenched by addition of wet THF and concentrated to a small volume. 10 mL of ethyl acetate and 10 mL of aqueous solution of HCl (0.5N) were added. The organic layer was then washed with water and dried over sodium sulfate to yield 177.8 mg (77.3%) of 8-benzyl-1,3-diethyl-4-hydroxy-bicyclo[3.2.1]-1β,3,8-triaza-spiro[4.5]dodecan-2-one as a yellowish oil. $^1$H NMR (400 MHz, DMSO-d$_6$) : δ [ppm] 7.36-7.28 (m, 4H), 7.21 (m, 1H), 6.05 (d, 1H), 4.70 (d, 1H), 3.51 (br s, 2H), 3.28 (m, 2H), 3.12 (m, 2H), 2.92 (m, 1H), 2.81 (m, 1H), 2.16 (d, 1H), 1.97-1.63 (m, 6H), 1.42 (d, 1H), 1.02 (m, 6H).

Step 2: 175 mg (0.509 mmol) of 8-benzyl-1,3-diethyl-4-hydroxy-bicyclo[3.2.1]-1β,3,8-triaza-spiro[4.5]dodecan-2-one was dissolved in 3 mL of formic acid and cooled to 0° C. To this solution was added 77 mg (2 mmol) of sodium borohydride in small portions. The solution was allowed to warm slowly to room temperature and then 20 mL of DCM and 30 mL of aqueous sodium hydroxide 1N were added. The aqueous layer was extracted twice with DCM. The combined organic layers were washed with brine and dried over sodium sulfate to yield 145 mg (87%) of 8-benzyl-1,3-diethyl-bicyclo[3.2.1]-1β,3,8-triaza-spiro[4.5]dodecan-2-one as a pale yellowish solid.

$^1$H NMR (400 MHz, DMSO-d$_6$): δ [ppm] 7.66 (m, 2H), 7.46 (m, 3H), 4.17 (d, 2H), 3.84 (br s, 2H), 3.42 (s, 2H), 3.13 (m, 2H), 3.06 (q, 2H), 2.32 (m, 2H), 2.23 (d, 2H), 2.08 (d, 2H), 1.87 (d, 2H), 1.0 (m, 6H).

Step 3: To 145 mg (0.44 mmol) of 8-benzyl-1,3-diethyl-bicyclo[3.2.1]-1β,3,8-triaza-spiro[4.5]dodecan-2-one previously dissolved in 4 mL of ethanol was added 83 mg (1.32 mmol) of ammonium formate and 61.4 mg (0.044 mmol) of palladium hydroxide. The reaction mixture was heated 3 minutes at 120° C. under microwave (Emrys Optimizer, Biotage) and then filtered over celite to yield 93.6 mg (89.6%) of 1,3-diethyl-bicyclo[3.2.1]-1β,3,8-triaza-spiro[4.5]dodecan-2-one as a colorless solid.

$^1$H NMR (400 MHz, DMSO-d$_6$): δ [ppm] 4.02 (br s, 2H), 3.36 (s, 2H), 3.05 (m, 4H), 2.07 (d×d, 2H), 1.95 (m, 4H), 1.80 (d, 2H), 1.02 (m, 6H).

PREPARATION 4

1-Isopropyl-3-methyl-bicyclo[3.2.1]-1β,3,8-triaza-spiro[4.5]dodecan-2,4-dione

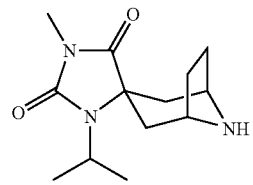

Step 1: To 9.22 g (42.8 mmol) of 8-benzyl-8-aza-bicyclo[3.2.1]octan-3-one previously dissolved in 42 mL of methanol was added successively 27.2 g (342 mmol) of ammonium acetate and 2.54 g of sodium cyanide. After stirring 24 hours at room temperature, 100 mL of DCM and 50 mL of water were added and the solution was extracted with DCM (2×100 mL). The organic layers were dried over sodium sulfate, filtered and evaporated in vacuo to yield 10.36 g (100%) of 3β-amino-8-benzyl-8-aza-bicyclo[3.2.1]octane-3-carbonitrile as a pale yellow oil.

Step 2: To 12.06 g (50 mmol) of 3β-amino-8-benzyl-8-aza-bicyclo[3.2.1]octane-3-carbonitrile previously dissolved in 50 mL of acetic acid was added dropwise 21.2 g (250 mmol) of potassium cyanate diluted in 25 mL of water. Then the reaction mixture was heated at 110° C. for one hour. After it had cooled to room temperature, 120 mL of aqueous hydrochloride acid solution (6N) was added and the reaction mixture was heated at 110° C. for one hour and concentrated. The residue was redissolved in 200 mL of ethyl acetate and quenched with a saturated solution of sodium carbonate. The organic layer was washed with brine, dried over sodium sulfate, filtered off and concentrated. The orange residue was purified by flash silica gel chromatography eluting with ethyl acetate then DCM:MeOH 2% to 10% to yield 1.93 g (13.5%) of 8-benzyl-bicyclo[3.2.1]-1β,3,8-triaza-spiro[4.5]dodecan-2,4-dione as an off white solid.

Step 3: To a mixture of 3.58 g (12.54 mmol) of 8-benzyl-bicyclo[3.2.1]-1β,3,8-triaza-spiro[4.5]dodecan-2,4-dione and 1.73 g (12.54 mmol) of potassium carbonate in 100 mL of anhydrous DMF was added 1.29 mL (20.6 mmol) of iodomethane. The reaction mixture was stirred for 18 hours at room temperature, diluted with water and extracted with diethyl ether. The combining organic layers were washed with water, brine, dried over sodium sulfate, filtered and concentrated to yield 1.93 g (52%) of 8-benzyl-3-methyl-bicyclo[3.2.1]-1β,3,8-triaza-spiro[4.5]dodecan-2,4-dione as a white solid.

Step 4: To 1.93 g (6.46 mmol) of 8-benzyl-3-methyl-bicyclo[3.2.1]-1β,3,8-triaza-spiro[4.5]dodecan-2,4-dione previously dissolved in 70 mL of anhydrous DMF was added 776 mg (19.4 mmol) of sodium hydride. The mixture was stirred at room temperature under nitrogen atmosphere for 5 minutes and 2-iodopropane (1.94 mL, 19.4 mmol) was added in one portion. The reaction was stirred for 3 days, quenched with water and extracted twice with diethyl ether. The combined organic layers were washed with water, brine and dried over sodium sulfate to yield, after flash silica gel chromatography eluting with hexanes:ethyl acetate 0% to 100%, 1.03 g (47%) of 8-benzyl-1-isopropyl-3-methyl-bicyclo[3.2.1]-1β,3,8-triaza-spiro[4.5]dodecan-2,4-dione.

$^1$H NMR (400 MHz, CDCl$_3$): δ [ppm] 7.37-7.24 (m, 5H), 3.64 (sept., 1H), 3.51 (s, 2H), 3.22 (br s, 2H), 2.91 (s, 3H), 2.21 (m, 2H), 2.09-2.01 (m, 4H), 1.78 (d×d, 2H), 1.46 (d, 6H).

Step 5: To 116 mg (1.83 mmol) of ammonium formate and 86 mg (0.12 mmol) of palladium hydroxide placed in a 5 mL microwave tube was added 209 mg (0.61 mmol) of 8-benzyl-1-isopropyl-3-methyl-bicyclo[3.2.1]-1β,3,8-triaza-spiro[4.5]dodecan-2,4-dione previously dissolved in 4 mL of ethanol. The tube was sealed and subjected to microwaves for 3 minutes at 120° C. and cooled to room temperature. The reaction mixture was filtered through celite, rinsed with ethanol and concentrated in vacuo to yield 150 mg (98%) of 1-isopropyl-3-methyl-bicyclo[3.2.1]-1β,3,8-triaza-spiro[4.5]dodecan-2,4-dione.

$^1$H NMR (400 MHz, DMSO-d$_6$): δ [ppm] 3.59 (sept., 1H), 3.46 (br s, 2H), 2.74 (s, 3H), 1.80 (d×d, 2H), 1.66 (d, 2H), 1.58 (m, 2H), 1.29 (d, 6H).

PREPARATION 5

1-Isopropyl-3-methyl-bicyclo[3.2.1]-1β,3,8-triaza-spiro[4.5]dodecan-2-one

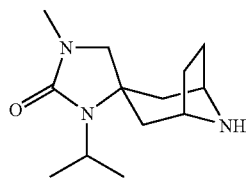

Step 1: N-Ethoxycarbonyltropinone (24.53 g, 124.3 mmol) was dissolved in 124 mL of methanol. Ammonium acetate (76.7 g, 8 eq.) was then added followed by sodium cyanide (7 g, 1.15 eq.). The reaction mixture was stirred overnight at room temperature. The solvent was then evaporated and 100 mL of water was added to the residue. The aqueous phase was extracted with DCM (3×200 mL). The resulting combined organic extracts was washed with 50 mL of water, dried over sodium sulfate and evaporated to yield 28.01 g of 3β-amino-3-cyano-8-aza-bicyclo[3.2.1]octane-8-carboxylic acid ethyl ester.

Step 2: To 7.83 g (35 mmol) of 3β-amino-3-cyano-8-aza-bicyclo[3.2.1]octane-8-carboxylic acid ethyl ester in DCM (100 mL) at 0° C. was added methyl isocyanate (2 g, 35 mmol) and the reaction stirred at room temperature overnight. The reaction mixture was diluted with DCM and washed with saturated sodium bicarbonate (2×50 mL), brine (2×20 mL) and then dried over sodium sulfate. The organic layer was concentrated and purified by flash silica gel chromatography eluting with MeOH:DCM to give 3.01 g (31%) of 3-cyano-3β-(3-methyl-ureido)-8-aza-bicyclo[3.2.1]octane-8-carboxylic acid ethyl ester as a white foam.

Step 3: 3.01 g (10.7 mmol) of 3-cyano-3β-(3-methyl-ureido)-8-aza-bicyclo[3.2.1]octane-8-carboxylic acid ethyl ester in 6M HCl (20 mL) was heated at 80° C. for one hour. The reaction mixture was neutralized with 1N NaOH (40 mL) and extracted twice with DCM. The combined organics were dried over sodium sulfate, filtered and concentrated to give 2.94 g (97%) of 3-methyl-bicyclo[3.2.1]-1β,3,8-triaza-spiro[4.5]dodecan-2,4-dione-8-carboxylic acid ethyl ester as a white foam.

Step 4: To 2.94 g (10.4 mmol) of 3-methyl-bicyclo[3.2.1]-1β,3,8-triaza-spiro[4.5]dodecan-2,4-dione-8-carboxylic acid ethyl ester in DMF (50 mL) was added sodium hydride (1.25 g, 31.4 mmol). The reaction was stirred at room temperature for 0.5 hour until hydrogen evolution ceased. 2-Iodopropane (3.1 mL, 31.4 mmol) was added to the reaction mixture and heated at 60° C. overnight. A second portion of sodium hydride (0.62 g, 15.7 mmol) was added to the crude reaction mixture and stirred at room temperature for 0.5 hour until hydrogen evolution ceased. A second portion of 2-iodopropane (1.55 mL, 15.7 mmol) was added and heated at 60° C. overnight. The reaction mixture was diluted with water (50 mL) and extracted twice with diethyl ether (2×300 mL). The organics were dried over sodium sulfate, concentrated and purified by flash silica gel chromatography eluting with ethyl acetate:hexanes (20%-100%) to give 2.02 g (60%) of 1-isopropyl-3-methyl-bicyclo[3.2.1]-1β,3,8-triaza-spiro[4.5]dodecan-2,4-dione-8-carboxylic acid ethyl ester as a white foam.

$^1$H NMR (400 MHz, CDCl$_3$): δ [ppm] 4.4-4.2 (m, 4H), 3.09 (sept., 1H), 2.92 (s, 3H), 2.3-1.9 (m, 6H), 1.78 (d, 2H), 1.39 (d, 6H), 1.27 (t, 3H).

Step 5: To 2.02 g (6.24 mmol) of 1-isopropyl-3-methyl-bicyclo[3.2.1]-1β,3,8-triaza-spiro[4.5]dodecan-2,4-dione-8-carboxylic acid ethyl ester in THF (70 mL) was added LAH (6.56 mL, 6.56 mmol, 1M in THF) dropwise at 0° C. The reaction mixture was diluted with water:THF (1:1, 50 mL) and acidified to pH 2 with 1N HCl (20 mL). The aqueous was extracted twice with ethyl acetate (3×150 mL). The organics were washed with 1M NaOH (50 mL), brine (50 mL) dried over sodium sulfate and concentrated to give 1.47 g as a white solid. The crude was taken up in formic acid (25 mL) at 0° C. and sodium borohydride (0.945 g, 24.9 mmol) was added portionwise. The reaction allowed warming to room temperature for 0.5 hour. The reaction mixture was diluted with DCM, and neutralized with 6M NaOH. The aqueous was extracted twice with DCM. The organic layer was washed with brine, dried over sodium sulfate and concentrated to give 1.33 g (69%) of 1-isopropyl-3-methyl-bicyclo[3.2.1]-1β,3,8-triaza-spiro[4.5]dodecan-2-one-8-carboxylic acid ethyl ester as a white solid.

Step 6: To 1.33 g (4.3 mmol) of 1-isopropyl-3-methyl-bicyclo[3.2.1]-1β,3,8-triaza-spiro[4.5]dodecan-2-one-8-carboxylic acid ethyl ester in toluene (50 mL) was added iodotrimethylsilane (1.75 mL, 12.9 mmol) and heated at 120° C. for 3 hours. The reaction mixture was concentrated and triturated with methanol (2×20 mL). The residue was purified by flash silica gel chromatography eluting with 2-20% MeOH: DCM to give 0.522 g (51%) of 1-isopropyl-3-methyl-bicyclo [3.2.1]-1β,3,8-triaza-spiro[4.5]dodecan-2-one as a white foam.

EXAMPLE 1

4,4-Difluoro-cyclohexanecarboxylic acid {(S)-3-[3-(4-methanesulfonyl-benzyl)-bicyclo[3.2.1]-2,4-dioxo-1α,3,8-triaza-spiro[4.5]dodec-8-yl]-1-phenyl-propyl}-amide

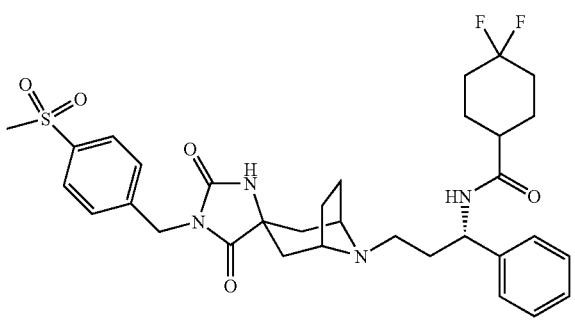

To a solution of 40 mg (0.1 mmol) of 3-(4-methanesulfonylbenzyl)-bicyclo[3.2.1]-1α,3,8-triaza-spiro[4.5]dodecan-2,4-dione hydrochloride in 1.7 mL of anhydrous DCE were added successively 24 mg (0.1 mmol) of 4,4-difluoro-cyclohexanecarboxylic acid ((S)-3-oxo-1-phenyl-propyl)-amide and 17 μL (0.12 mmol) of triethylamine. The reaction mixture was agitated at room temperature for 10 minutes before adding 26 mg (0.125 mmol) of sodium triacetoxyborohydride. After an overnight agitation, 2 mL of saturated solution of sodium bicarbonate was added. The solution was then extracted with DCM (2×2 mL), dried over sodium sulfate, filtered and concentrated in vacuo. The crude mixture was purified by Bond Elut (ethyl acetate to 5% methanol/DCM) to yield the 4,4-difluoro-cyclohexanecarboxylic acid {(S)-3-[3-(4-methanesulfonylbenzyl)-bicyclo[3.2.1]-2,4-dioxo-1α,3,8-triaza-spiro[4.5]dodec-8-yl]-1-phenyl-propyl}-amide as a white solid (40 mg, 62.3%).

$^1$H NMR (400 MHz, DMSO-d$_6$): δ [ppm] 8.61 (s, 1H), 8.49 (d, 1H), 7.87 (d, 2H), 7.43 (d, 2H), 7.30-7.24 (m, 4H), 7.19-7.16 (m, 1H), 4.88-4.82 (m, 1H), 4.62 (s, 2H), 3.18 (s, 3H), 3.22-3.16 (m, 2H), 2.40-2.26 (m, 3H), 2.20-2.13 (m, 2H), 2.05-1.97 (m, 2H), 1.88-1.70 (m, 9H), 1.60-1.50 (m, 4H).

EXAMPLE 2

4,4-Difluoro-cyclohexanecarboxylic acid {(S)-3-[1,3-diethyl-bicyclo[3.2.1]-2,4-dioxo-1β,3,8-triaza-spiro[4.5]dodec-8-yl]-1-phenyl-propyl}-amide

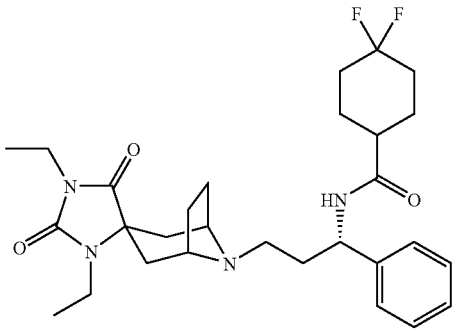

To 32 mg (0.13 mmol) of 1,3-diethyl-bicyclo[3.2.1]-1β,3, 8-triaza-spiro[4.5]dodecan-2,4-dione and 38.4 mg (0.13 mmol) of 4,4-difluoro-cyclohexanecarboxylic acid ((S)-3-oxo-1-phenyl-propyl)-amide was added 2.2 mL of anhydrous DCE and 34 mg (0.17 mmol) of sodium triacetoxyborohydride. After an overnight agitation, 2 mL of saturated solution of sodium bicarbonate was added. The solution was then extracted with DCM (2×2 mL), dried over sodium sulfate, filtered and concentrated in vacuo. The crude mixture was purified by Bond Elut (ethyl acetate to 5% methanol/DCM) to yield 42 mg (60.9%) of 4,4-difluoro-cyclohexanecarboxylic acid {(S)-3-[1,3-diethyl-bicyclo[3.2.1]-2,4-dioxo-1β,3,8-triaza-spiro[4.5]dodec-8-yl]-1-phenyl-propyl}-amide.

$^1$H NMR (400 MHz, DMSO-d$_6$): δ [ppm] 8.24 (d, 1H), 7.31-7.25 (m, 4H), 7.21-7.17 (m, 1H), 4.99-4.97 (m, 1H), 3.34-3.29 (m, 2H), 3.24-3.17 (m, 4H), 2.30-2.24 (m, 3H), 2.04-1.90 (m, 6H), 1.78-1.55 (m, 12H), 1.15 (t, 3H), 1.02 (t, 3H).

EXAMPLE 3

4,4-Difluoro-cyclohexanecarboxylic acid {(S)-3-[1, 3-diethyl-bicyclo[3.2.1]-2-oxo-1β,3,8-triaza-spiro [4.5]dodec-8-yl]-1-phenyl-propyl}-amide hydrochloride

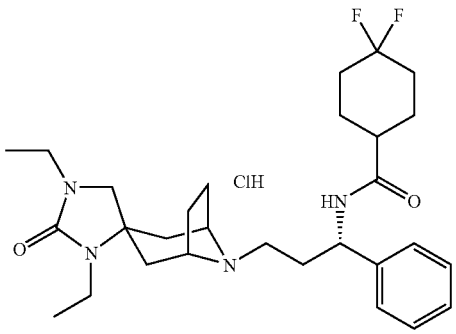

To 19 mg (0.08 mmol) of 1,3-diethyl-bicyclo[3.2.1]-1β,3,8-triaza-spiro[4.5]dodecan-2-one and 23.6 mg (0.08 mmol) of 4,4-difluoro-cyclohexanecarboxylic acid ((S)-3-oxo-1-phenyl-propyl)-amide was added 1.5 mL of anhydrous DCE and 26.7 mg (0.12 mmol) of sodium triacetoxyborohydride. After an overnight agitation, 2 mL of saturated solution of sodium bicarbonate was added. The solution was then extracted with DCM (2×2 mL), dried over sodium sulfate, filtered and concentrated in vacuo. The crude mixture was purified by semi-preparative HPLC (Method A) to yield 17.7 mg (40%) of 4,4-difluoro-cyclohexanecarboxylic acid {(S)-3-[1,3-diethyl-bicyclo[3.2.1]-2-oxo-1β,3,8-triaza-spiro[4.5]dodec-8-yl]-1-phenyl-propyl}-amide hydrochloride.

$^1$H NMR (400 MHz, DMSO-d$_6$): δ [ppm] 10.3 (br s, 1H), 8.47 (d, 1H), 7.3 (m, 4H), 7.23 (m, 1H), 4.82 (m, 1H), 4.02 (br d, 2H), 3.39 (s, 2H), 3.15 (q, 2H), 3.04 (q, 2H), 2.87 (m, 2H), 2.31 (m, 3H), 2.19-2.0 (m, 8H), 1.85-1.50 (m, 8H), 0.98 (m, 6H).

Table 1 of compounds illustrates some of the compounds of the present invention which were synthesized using the procedures described in scheme 1.

Scheme 2

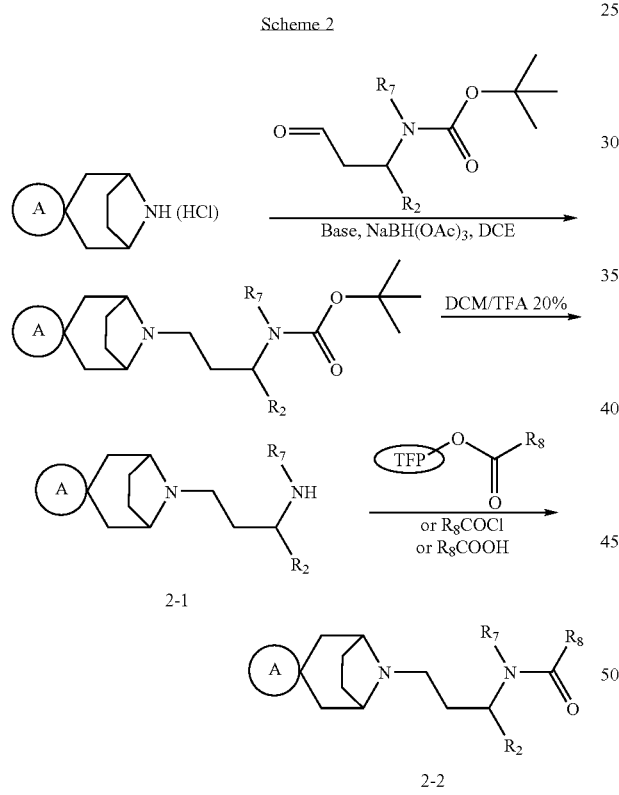

General procedure: the free amine 2-1 is condensed with preactivated carboxylic acid R$_8$COOH on polymeric 4-hydroxy-2,3,5,6-tetrafluorobenzamido (TFP) resin (see preparation in J. M. Salvino et al. *J. Comb. Chem.* 2000, 2, 691-697) in solvent such as DMF, or condensed with acid chloride R$_8$COCl in solvent such as DCM in presence of a base such as triethylamine or diisopropylethylamine, or condensed with a carboxylic acid R$_8$COOH in solvents such as DMF, DCM or DCE with coupling agents such as HOBt, DIC, HATU, BOP, PyBOP, or supported coupling agent such as PL-EDC, to provide acylated compound 2-2.

EXAMPLE 4

[(S)-3-(1-Isopropyl-3-methyl-bicyclo[3.2.1]-2,4-dioxo-1β,3,8-triaza-spiro[4.5]dodec-8-yl)-1-phenyl-propyl]-carbamic acid tert-butyl ester

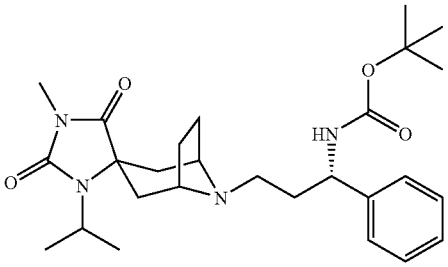

To 300 mg (1.19 mmol) of 1-isopropyl-3-methyl-bicyclo[3.2.1]-1β,3,8-triaza-spiro[4.5]dodecan-2,4-dione in anhydrous DCE (30 mL) was added 309 mg (1.24 mmol) of ((S)-3-oxo-1-phenyl-propyl)-carbamic acid tert-butyl ester. The reaction mixture was stirred for 30 minutes and 380 mg (1.79 mmol) of sodium triacetoxyborohydride was added in one portion. Then the reaction mixture was agitated overnight at room temperature, diluted with DCM, washed with saturated solution of sodium bicarbonate and dried over sodium sulfate. The residue was purified by flash silica gel chromatography eluting with ethyl acetate:hexanes (0 to 100%) then DCM:methanol (9:1) to yield 509 mg (85%) of [(S)-3-(1-isopropyl-3-methyl-bicyclo[3.2.1]-2,4-dioxo-1β,3,8-triaza-spiro[4.5]dodec-8-yl)-1-phenyl-propyl]-carbamic acid tert-butyl ester.

EXAMPLE 5

8-((S)-3-Amino-3-phenyl-propyl)-1-isopropyl-3-methyl-bicyclo[3.2.1]-1β,3,8-triaza-spiro[4.5]dodecane-2,4-dione

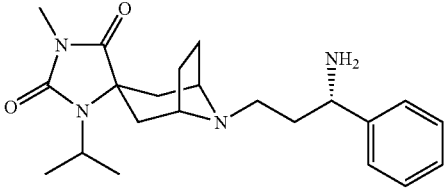

To 495 mg (1.02 mmol) of [(S)-3-(1-isopropyl-3-methyl-bicyclo[3.2.1]-2,4-dioxo-1β,3,8-triaza-spiro[4.5]dodec-8-yl)-1-phenyl-propyl]-carbamic acid tert-butyl ester in 6 mL of anhydrous DCM was added 2 mL of TFA. The reaction mixture was stirred at room temperature for 3 hours, diluted with DCM, washed twice with 1N NaOH and dried over sodium sulfate to give, after concentration in vacuo, 370 mg (94%) of 8-((S)-3-amino-3-phenyl-propyl)-1-isopropyl-3-methyl-bicyclo[3.2.1]-1β,3,8-triaza-spiro[4.5]dodecane-2,4-ione.

EXAMPLE 6

Cyclobutane carboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide hydrochloride

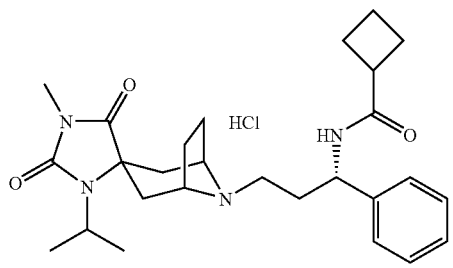

To 85 mg of preswollen PL-EDC resin (Polymer Laboratories, loading of 1.42 mmol/g) in 0.5 mL of DCE was added 23 mg (60 μmol) of 8-((S)-3-amino-3-phenyl-propyl)-1-isopropyl-3-methyl-bicyclo[3.2.1]-1β,3,8-triaza-spiro[4.5]dodecane-2,4-dione dissolved in 1 mL of DCE and 6 mg (60 μmol) of cyclobutane carboxylic acid. The reaction mixture was stirred overnight at room temperature, filtered off, washed with DCM and concentrated in vacuo. The crude was purified by semi-preparative HPLC (Method B) to give 22.8 mg (75.5%) of cyclobutane carboxylic acid {(S)-3-[1-isopropyl-3-ethyl-bicyclo[3.2.1]-2,4-dioxo-1β,3,8-triaza-spiro[4.5]dodec-8-yl]-1-phenyl-propyl}-amide hydrochloride after lyophilization.

Table 2 of compounds illustrates some of the compounds of the present invention which were synthesized using the procedures described in scheme 2.

Scheme 3

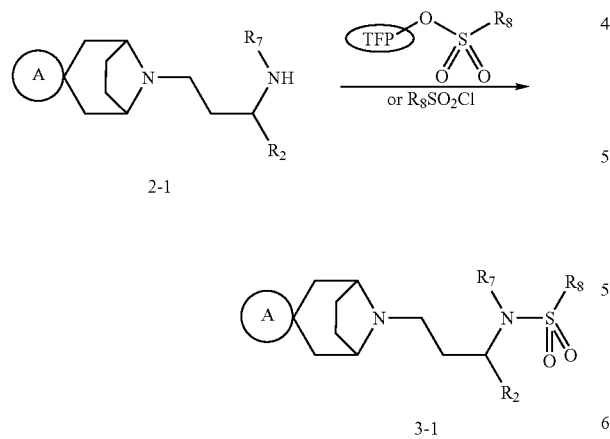

General procedure: the free amine 2-1 is condensed with preactivated sulfonyl chloride $R_8SO_2Cl$ on polymeric 4-hydroxy-2,3,5,6-tetrafluorobenzamido (TFP) resin (see preparation in J. M. Salvino et al. J. Comb. Chem. 2000, 2, 691-697) in solvent such as DMF, or with sulfonyl chloride $R_8SO_2Cl$ in solvent such as DCM in presence of a base such as triethylamine or diisopropylethylamine to provide the sulphonamide 3-1.

Scheme 4

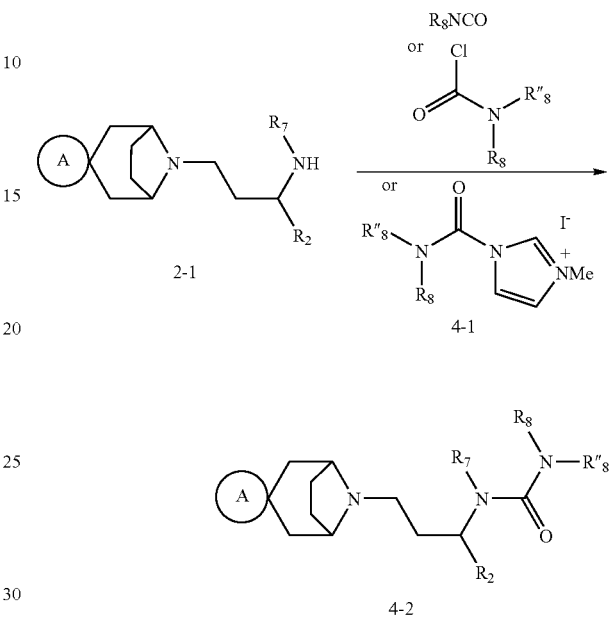

General procedure: the free amine 2-1 is submitted to reaction with isocyanate in solvent such as THF, or condensed with carbamoyl chloride derivative or with cationic carbamoyl imidazolium intermediate 4-1 (see R. A. Batey et al. Comb. Chem. High Throughput Screening 2002, 5, 219-232) in solvent such as DCM in presence of base such as triethylamine or diisopropylethylamine to provide the urea 4-2.

Scheme 5

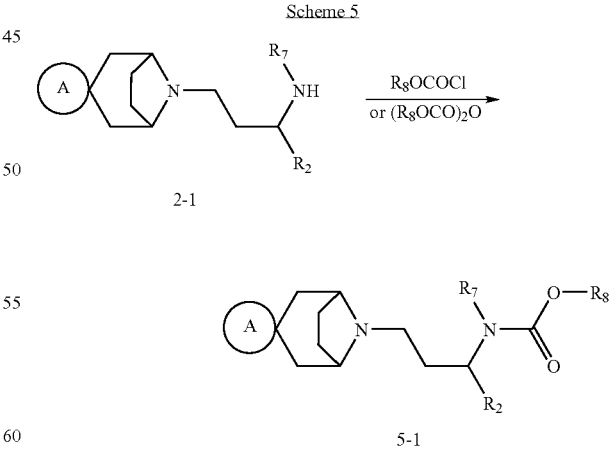

General procedure: the free amine 2-1 is condensed with chloroformate or symmetric anhydride in solvents such as DCM or 1,2-dichloroethane in the presence of a base such as triethylamine or diisopropylethylamine to provide the carbamate 5-1.

TABLE 1

| CPD # | STRUCTURE | COMPOUND NAME | MW |
|---|---|---|---|
| 1 | 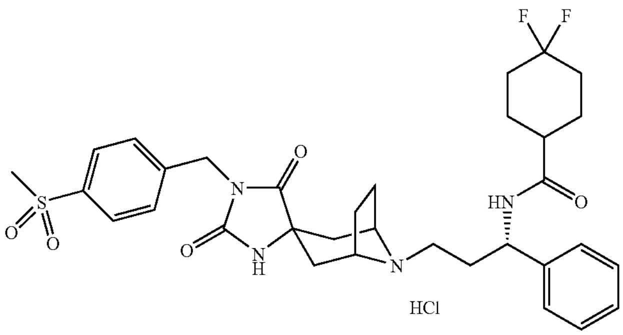 | 4,4-Difluoro-cyclohexanecarboxylic acid {(S)-3-[3-(4-methanesulfonyl-benzyl)-bicyclo[3.2.1]-2,4-dioxo-1β,3,8-triaza-spiro[4.5]dodec-8-yl]-1-phenyl-propyl}-amide hydrochloride | 679.23 |
| 2 | 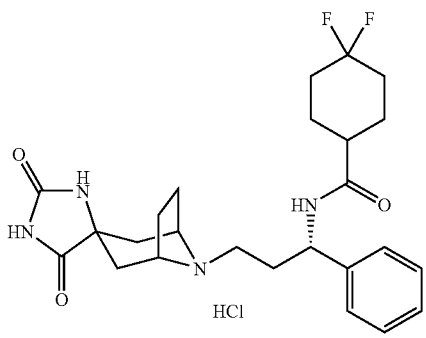 | 4,4-Difluoro-cyclohexanecarboxylic acid {(S)-3-[bicyclo[3.2.1]-2,4-dioxo-1α,3,8-triaza-spiro[4.5]dodec-8-yl]-1-phenyl-propyl}-amide hydrochloride | 511.02 |
| 3 | 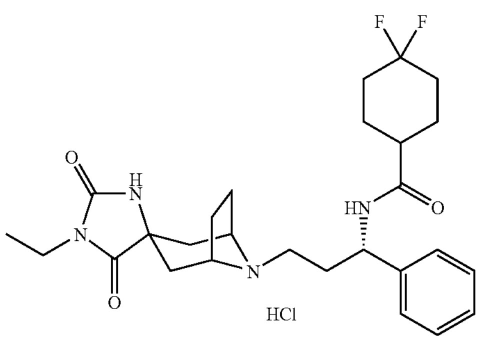 | 4,4-Difluoro-cyclohexanecarboxylic acid {(S)-3-[3-ethyl-bicyclo[3.2.1]-2,4-dioxo-1α,3,8-triaza-spiro[4.5]dodec-8-yl]-1-phenyl-propyl}-amide hydrochloride | 539.07 |
| 4 | 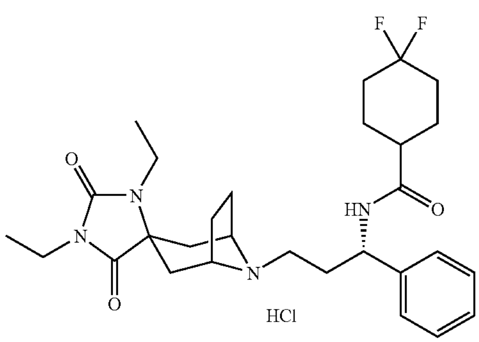 | 4,4-Difluoro-cyclohexanecarboxylic acid {(S)-3-[1,3-diethyl-bicyclo[3.2.1]-2,4-dioxo-1α,3,8-triaza-spiro[4.5]dodec-8-yl]1-phenyl-propyl}-amide hydrochloride | 567.12 |

TABLE 1-continued

| CPD # | STRUCTURE | COMPOUND NAME | MW |
|---|---|---|---|
| 5 | 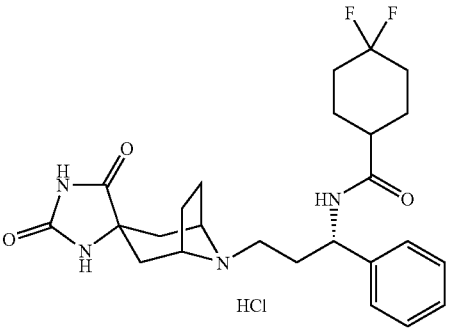 | 4,4-Difluoro-cyclohexanecarboxylic acid {(S)-3-[bicyclo[3.2.1]-2,4-dioxo-1β,3,8,-triaza-spiro[4.5]dodec-8-yl]-1-phenyl-propyl}-amide hydrochloride | 511.02 |
| 6 | 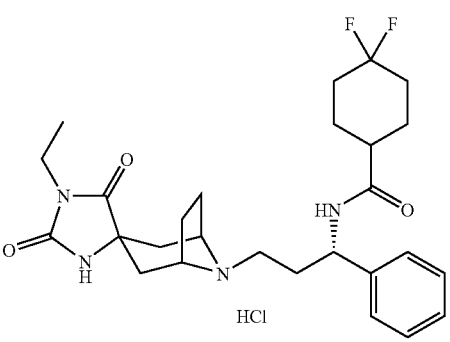 | 4,4-Difluoro-cyclohexanecarboxylic acid {(S)-3-[3-ethyl-bicyclo[3.2.1]-2,4-dioxo-1β,3,8-triaza-spiro[4.5]dodec-8-yl]-1-phenyl-propyl}-amide hydrochloride | 539.07 |
| 7 | 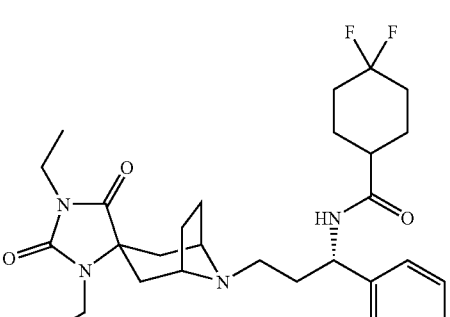 | 4,4-Difluoro-cyclohexanecarboxylic acid {(S)-3-[1,3-diethyl-bicyclo[3.2.1]-2,4-dioxo-1β,3,3,8-triaza-spiro[4.5]dodec-8-yl]-1-phenyl-propyl}-amide | 530.65 |
| 8 | 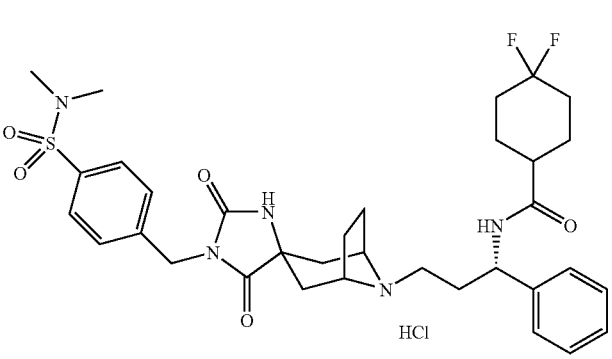 | 4,4-Difluoro-cyclohexanecarboxylic acid {(S)-3-[3-(4-dimethylsulfamoyl-benzyl)-bicyclo[3.2.1]-2,4-dioxo-1α,3,8-triaza-spiro[4.5]dodec-8-yl]-1-phenyl-propyl}-amide hydrochloride | 708.27 |

TABLE 1-continued

| CPD # | STRUCTURE | COMPOUND NAME | MW |
|---|---|---|---|
| 9 | 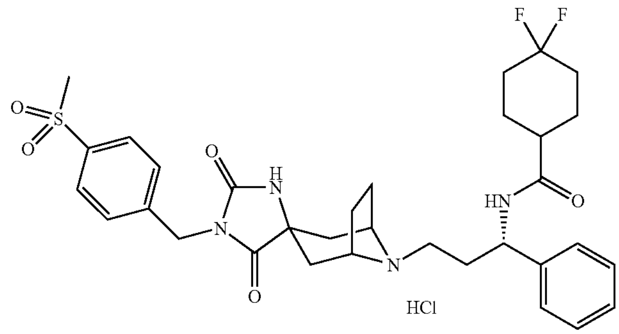 | 4,4-Difluoro-cyclohexanecarboxylic acid {(S)-3-[3-(4-methanesulfonyl-benzyl)-bicyclo[3.2.1]-2,4-dioxo-1α,3,8-triaza-spiro[4.5]dodec-8-yl]-1-phenyl-propyl}-amide hydrochloride | 679.23 |
| 10 | 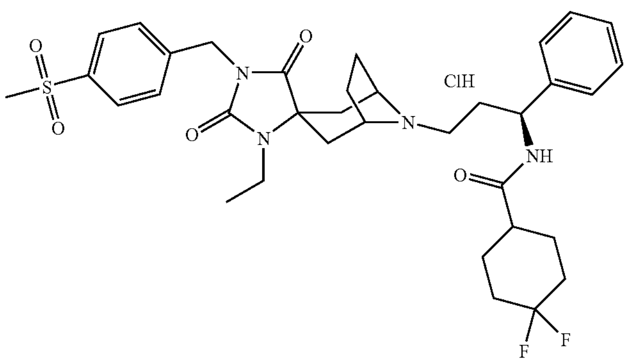 | 4,4-Difluoro-cyclohexanecarboxylic acid {(S)-3-[1-ethyl-3-(4-methanesulfonyl-benzyl)-bicyclo[3.2.1]-2,4-dioxo-1β,3,8-triaza-spiro[4.5]dodec-8-yl]-1-phenyl-propyl}-amide hydrochloride | 707.27 |
| 11 | 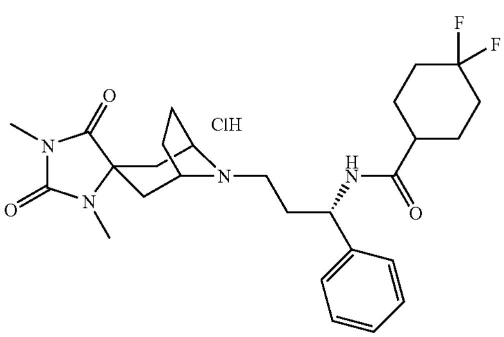 | 4,4-Difluoro-cyclohexanecarboxylic acid {(S)-3-[1,3-dimethyl-bicyclo[3.2.1]-2,4-dioxo-1β,3,8-triaza-spiro[4.5]dodec-8-yl]-1-phenyl-propyl}-amide hydrochloride | 539.06 |
| 12 | 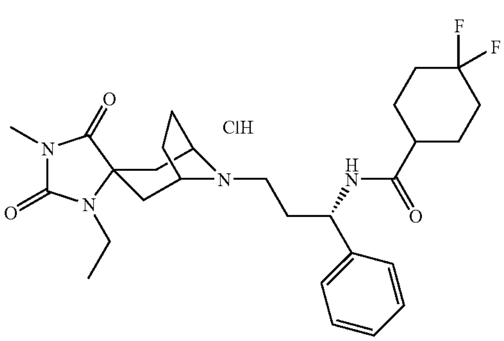 | 4,4-Difluoro-cyclohexanecarboxylic acid {(S)-3-[1-ethyl-3-methyl-bicyclo[3.2.1]-2,4-dioxo-1β,3,8-triaza-spiro[4.5]dodec-8-yl]-1-phenyl-propyl}-amide hydrochloride | 553.09 |

TABLE 1-continued

| CPD # | STRUCTURE | COMPOUND NAME | MW |
|---|---|---|---|
| 13 | 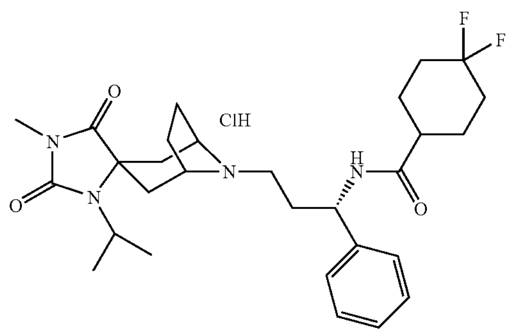 | 4,4-Difluoro-cyclohexanecarboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide hydrochloride | 567.11 |
| 14 | 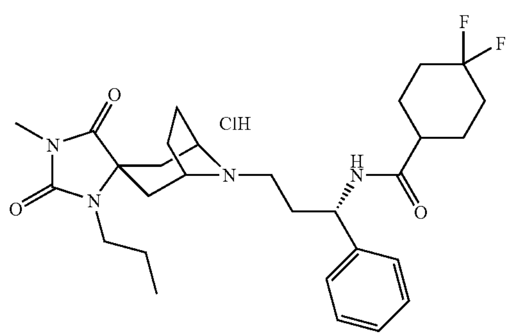 | 4,4-Difluoro-cyclohexanecarboxylic acid {(S)-3-[1-propyl-3-methyl-bicyclo[3.2.1]-2,4-dioxo-1β,3,8-triaza-spiro[4.5]dodec-8-yl]-1-phenyl-propyl}-amide hydrochloride | 567.11 |
| 15 | 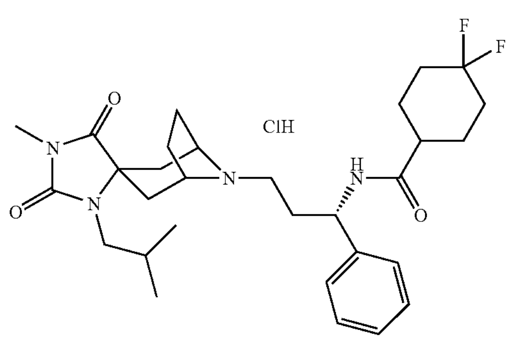 | 4,4-Difluoro-cyclohexanecarboxylic acid {(S)-3-8 1-isobutyl-3-methyl-bicyclo[3.2.1]-2,4-dioxo-1β,3,8-triaza-spiro[4.5]dodec-8-yl]-1-phenyl propyl}-amide hydrochloride | 581.14 |
| 16 | 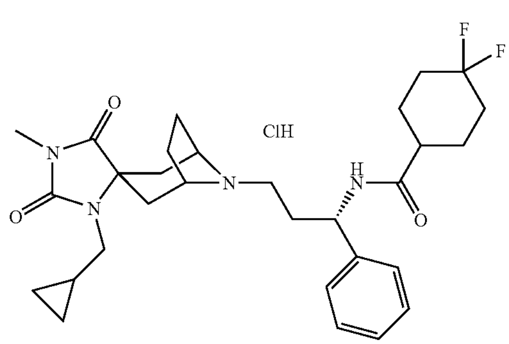 | 4,4-Difluoro-cyclohexanecarboxylic acid {(S)-3-[1-cyclopropylmethyl-3-methyl-bicyclo[3.2.1]-2,4-dioxo-1β,3,8-triaza-spiro[4.5]dodec-8-yl]-1-phenyl-propyl}-amide hydrochloride | 579.12 |

TABLE 1-continued

| CPD # | STRUCTURE | COMPOUND NAME | MW |
|---|---|---|---|
| 17 | 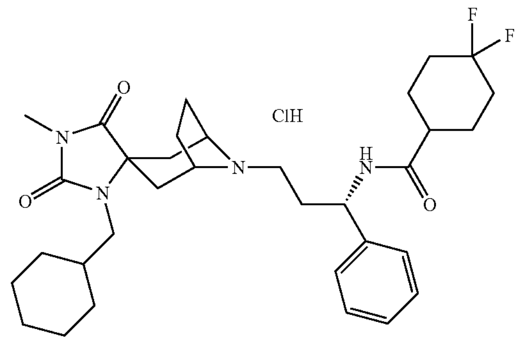 | 4,4-Difluoro-cyclohexanecarboxylic acid {(S)-3-[1-cyclohexylmethyl-3-methyl-bicyclo[3.2.1]-2,4-dioxo-1β,3,8-triaza-spiro[4.5]dodec-8-yl]-1-phenyl-propyl}-amide hydrochloride | 621.20 |
| 18 | 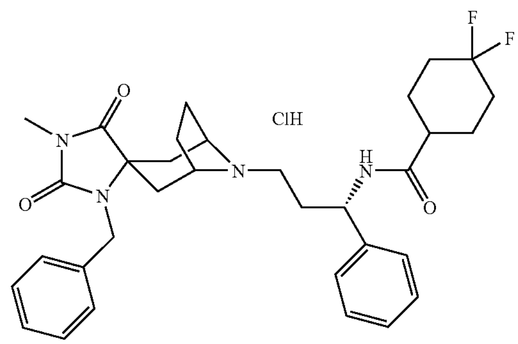 | 4,4-Difluoro-cyclohexanecarboxylic acid {(S)-3-[1-benzyl-3-methyl-bicyclo[3.2.1]-2,4-dioxo-1β,3,8-triaza-spiro[4.5]dodec-8-yl]-1-phenyl-propyl}-amide hydrochloride | 615.16 |
| 19 | 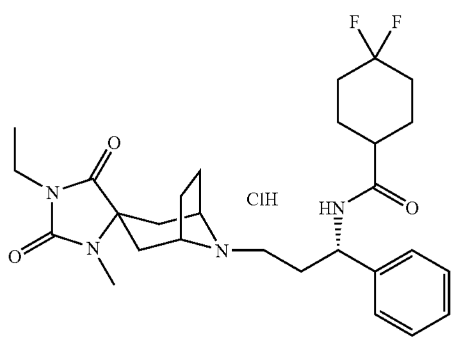 | 4,4-Difluoro-cyclohexanecarboxylic acid {(S)-3-[3-ethyl-1-methyl-bicyclo[3.2.1]-2,4-dioxo-1β,3,8-triaza-spiro[4.5]dodec-8-yl]-1-phenyl-propyl}-amide hydrochloride | 553.09 |
| 20 | 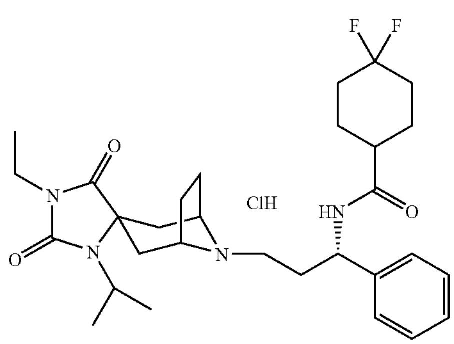 | 4,4-Difluoro-cyclohexanecarboxylic acid {(S)-3-[3-ethyl-1-isopropyl-bicyclo[3.2.1]-2,4-dioxo-1β,3,8-triaza-spiro[4.5]dodec-8-yl]-1-phenyl-propyl}-amide hydrochloride | 581.14 |

TABLE 1-continued

| CPD # | STRUCTURE | COMPOUND NAME | MW |
|---|---|---|---|
| 21 | 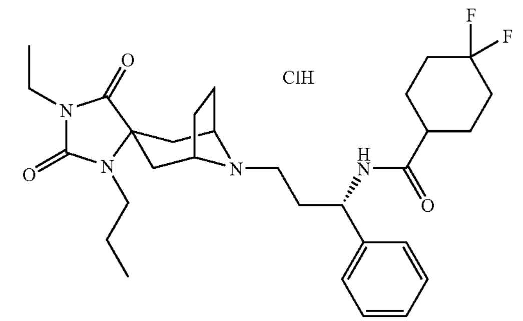 | 4,4-Difluoro-cyclohexanecarboxylic acid {(S)-3-[3-ethyl-1-propyl-bicyclo[3.2.1]-2,4-dioxo-1β,3,8-triaza-spiro[4.5]dodec-8-yl]-1-phenyl-propyl}-amide hydrochloride | 581.14 |
| 22 | 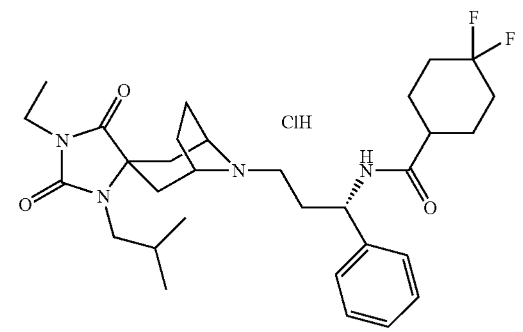 | 4,4-Difluoro-cyclohexanecarboxylic acid {(S)-3-[3-ethyl-1-isobutyl-bicyclo[3.2.1]-2,4-dioxo-1β,3,8-triaza-spiro[4.5]dodec-8-yl]-1-phenyl-propyl}-amide hydrochloride | 595.17 |
| 23 | 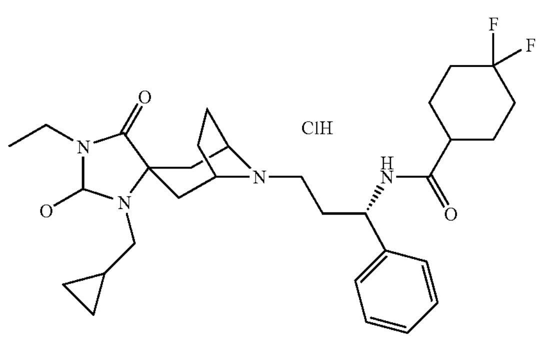 | 4,4-Difluoro-cyclohexanecarboxylic acid {(S)-3-[1-cyclopropylmethyl-3-ethyl-bicyclo[3.2.1]-2,4-dioxo-1β,3,8-triaza-spiro[4.5]dodec-8-yl]-1-phenyl-propyl}-amide hydrochloride | 593.15 |
| 24 | 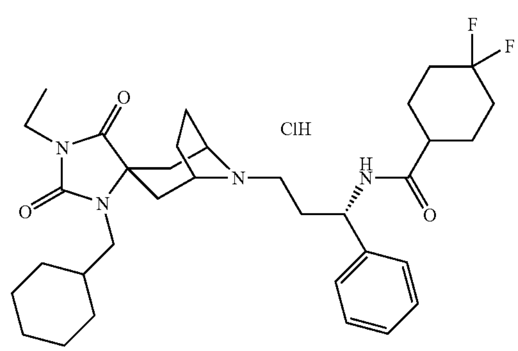 | 4,4-Difluoro-cyclohexanecarboxylic acid {(S)-3-[1-cyclohexylmethyl-3-ethyl-bicyclo[3.2.1]-2,4-dioxo-1β,3,8-triaza-spiro[4.5]dodec-8-yl]-1-phenyl-propyl}-amide hydrochloride | 635.23 |

TABLE 1-continued

| CPD # | STRUCTURE | COMPOUND NAME | MW |
|---|---|---|---|
| 25 | 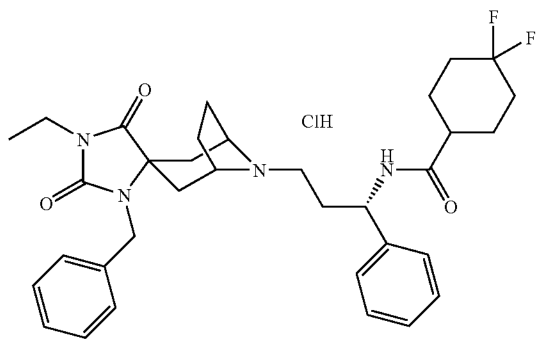 | 4,4-Difluoro-cyclohexanecarboxylic acid {(S)-3-[1-benzyl-3-ethyl-bicyclo[3.2.1]-2,4-dioxo-1β,3,8-triaza-spiro[4.5]dodec-8-yl]-1-phenyl-propyl}-amide hydrochloride | 629.18 |
| 26 | 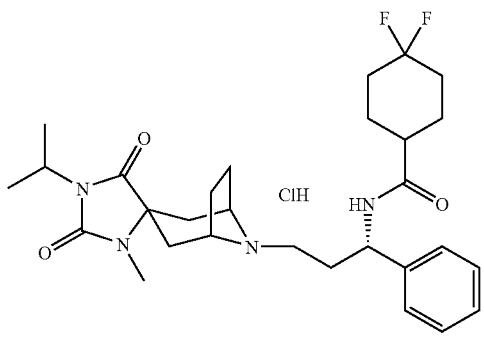 | 4,4-Difluoro-cyclohexanecarboxylic acid {(S)-3-[1-methyl-3-isopropyl-bicyclo[3.2.1]-2,4-dioxo-1β,3,8-triaza-spiro[4.5]dodec-8-yl]-1-phenyl-propyl}-amide hydrochloride | 567.11 |
| 27 | 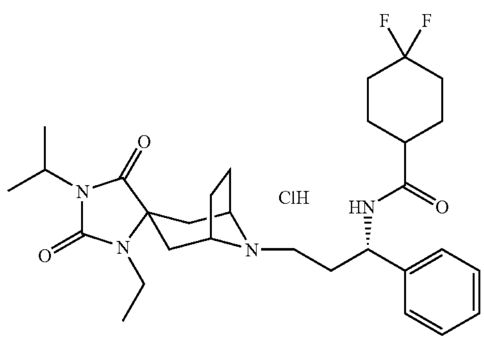 | 4,4-Difluoro-cyclohexanecarboxylic acid {(S)-3-[1-ethyl-3-isopropyl-bicyclo[3.2.1]-2,4-dioxo-1β,3,8-triaza-spiro[4.5]dodec-8-yl]-1-phenyl-propyl}-amide hydrochloride | 581.14 |
| 28 | 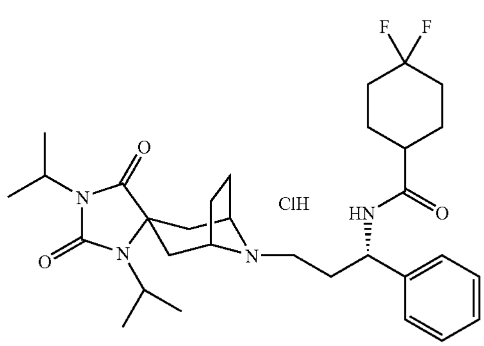 | 4,4-Difluoro-cyclohexanecarboxylic acid {(S)-3-[1,3-diisopropyl-bicyclo[3.2.1]-2,4-dioxo-1β,3,8-triaza-spiro[4.5]dodec-8-yl]-1-phenyl-propyl}-amide hydrochloride | 595.17 |

TABLE 1-continued

| CPD # | STRUCTURE | COMPOUND NAME | MW |
|---|---|---|---|
| 29 | 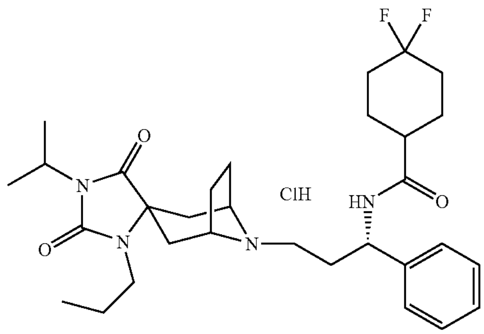 | 4,4-Difluoro-cyclohexanecarboxylic acid {(S)-3-[1-propyl-3-isopropyl-bicyclo[3.2.1]-2,4-dioxo-1β,3,8-triaza-spiro[4.5]dodec-8-yl]-1-phenyl-propyl}-amide hydrochloride | 595.17 |
| 30 | 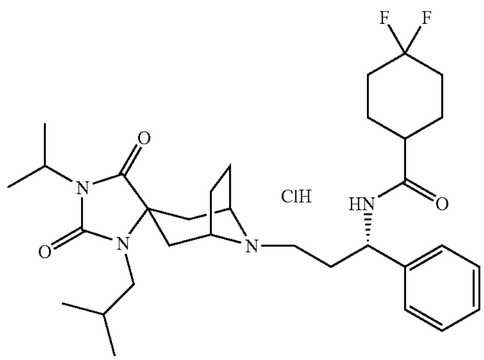 | 4,4-Difluoro-cyclohexanecarboxylic acid {(S)-3-[1-isobutyl-3-isopropyl-bicyclo[3.2.1]-2,4-dioxo-1β,3,8-triaza-spiro[4.5]dodec-8-yl]-1-phenyl-propyl}-amide hydrochloride | 609.19 |
| 31 | 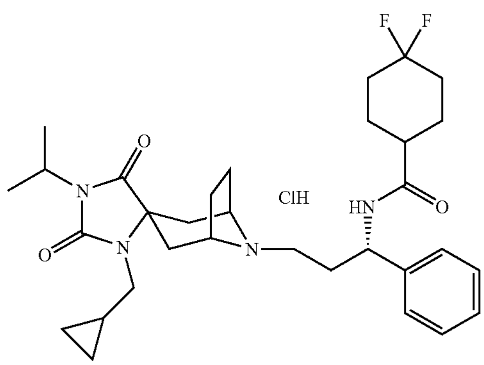 | 4,4-Difluoro-cyclohexanecarboxylic acid {(S)-3-[1-cyclopropylmethyl-3-isopropyl-bicyclo[3.2.1]-2,4-dioxo-1β,3,8-triaza-spiro[4.5]dodec-8-yl]-1-phenyl-propyl}-amide hydrochloride | 607.18 |
| 32 | 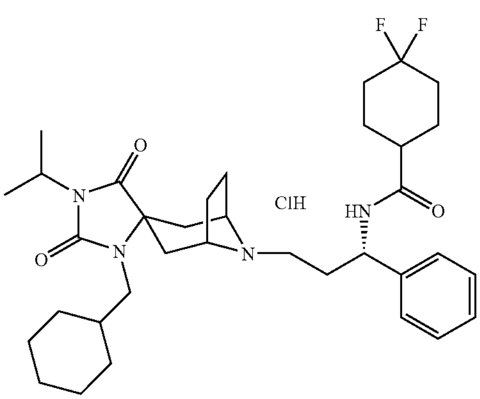 | 4,4-Difluoro-cyclohexanecarboxylic acid {(S)-3-[1-cyclohexylmethyl-3-isopropyl-bicyclo[3.2.1]-2,4-dioxo-1β,3, 8-triaza-spiro[4.5]dodec-8-yl]-1-phenyl-propyl}-amide hydrochloride | 649.26 |

TABLE 1-continued

| CPD # | STRUCTURE | COMPOUND NAME | MW |
|---|---|---|---|
| 33 | 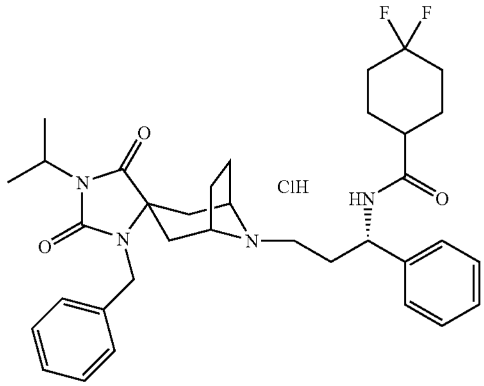 | 4,4-Difluoro-cyclohexanecarboxylic acid {(S)-3-[1-benzyl-3-isopropyl-bicyclo[3.2.1]-2,4-dioxo-1β,3,8-triaza-spiro[4.5]dodec-8-yl]-1-phenyl-propyl}-amide hydrochloride | 643.21 |
| 34 | 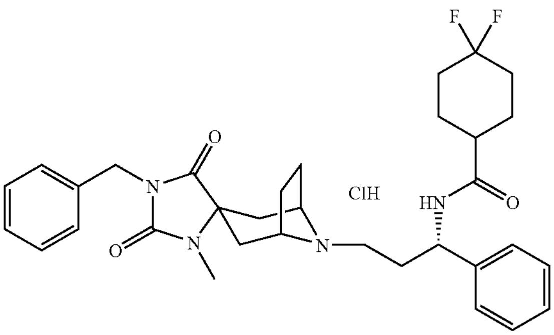 | 4,4-Difluoro-cyclohexanecarboxylic acid {(S)-3-[1-methyl-3-benzyl-bicyclo[3.2.1]-2,4-dioxo-1β,3,8-triaza-spiro[4.5]dodec-8-yl]-1-phenyl-propyl}-amide hydrochloride | 615.16 |
| 35 | 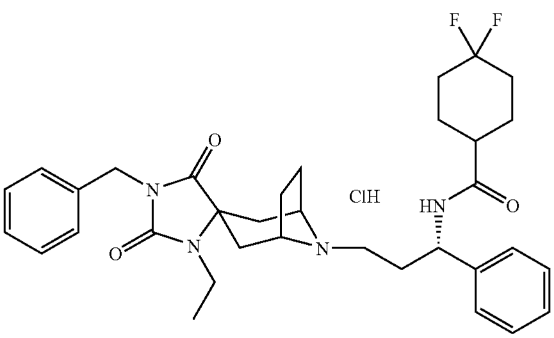 | 4,4-Difluoro-cyclohexanecarboxylic acid {(S)-3-[1-ethyl-3-benzyl-bicyclo[3.2.1]-2,4-dioxo-1β,3,8-triaza-spiro[4.5]dodec-8-yl]-1-phenyl-propyl}-amide hydrochloride | 629.18 |
| 36 | 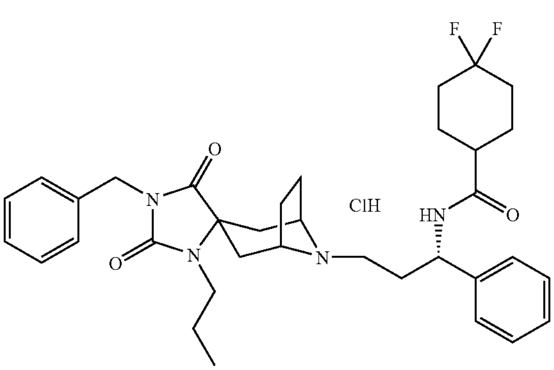 | 4,4-Difluoro-cyclohexanecarboxylic acid {(S)-3-[1-propyl-3-benzyl-bicyclo[3.2.1]-2,4-dioxo-1β,3,8-triaza-spiro[4.5]dodec-8-yl]-1-phenyl-propyl}-amide hydrochloride | 643.21 |

TABLE 1-continued

| CPD # | STRUCTURE | COMPOUND NAME | MW |
|---|---|---|---|
| 37 | 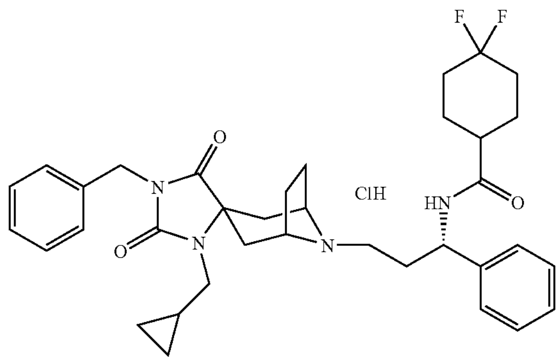 | 4,4-Difluoro-cyclohexanecarboxylic acid {(S)-3-[1-cyclopropylmethyl-3-benzyl-bicyclo[3.2.1]-2,4-dioxo-1β,3,8-triaza-spiro[4.5]dodec-8-yl]-1-phenyl-propyl}-amide hydrochloride | 655.22 |
| 38 | 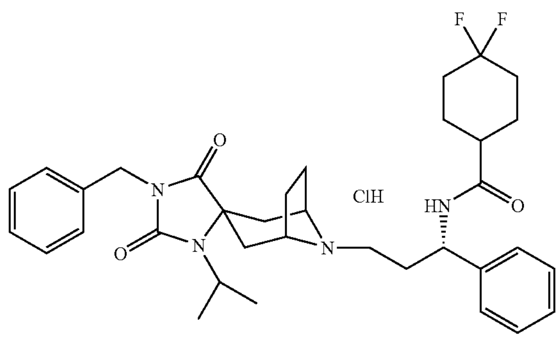 | 4,4-Difluoro-cyclohexanecarboxylic acid {(S)-3-[1-isopropyl-3-benzyl-bicyclo[3.2.1]-2,4-dioxo-1β,3,8-triaza-spiro[4.5]dodec-8-yl]-1-phenyl-propyl}-amide hydrochloride | 643.21 |
| 39 | 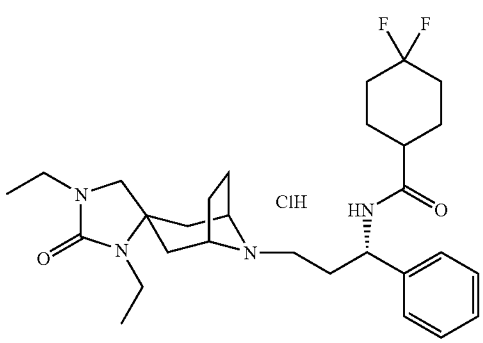 | 4,4-Difluoro-cyclohexanecarboxylic acid {(S)-3-[1,3-diethyl-bicyclo[3.2.1]-2-oxo-1β,3,8-triaza-spiro[4.5]dodec-8-yl]-1-phenyl-propyl}-amide hydrochloride | 553.13 |
| 40 | 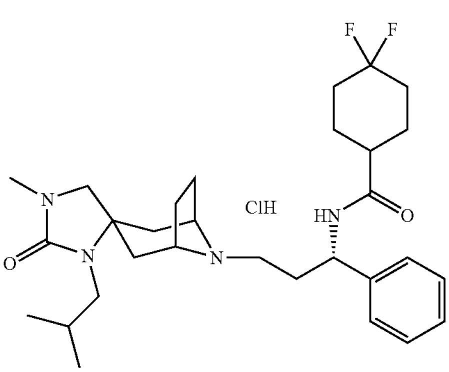 | 4,4-Difluoro-cyclohexanecarboxylic acid {(S)-3-[1-isobutyl-3-methyl-bicyclo[3.2.1]-2-oxo-1β,3,8-triaza-spiro[4.5]dodec-8-yl]-1-phenyl-propyl}-amide hydrochloride | 567.16 |

TABLE 1-continued

| CPD # | STRUCTURE | COMPOUND NAME | MW |
|---|---|---|---|
| 41 | 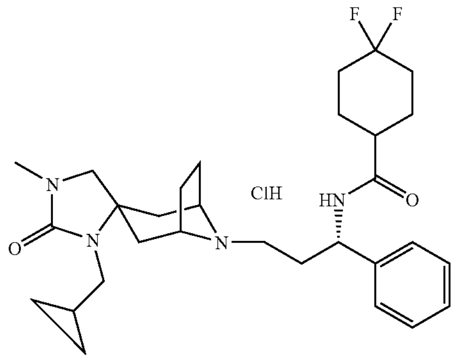 | 4,4-Difluoro-cyclohexanecarboxylic acid {(S)-3-[1-cyclopropylmethyl-3-methyl-bicyclo[3.2.1]-2-oxo-1β,3,8-triaza-spiro[4.5]dodec-8-yl]-1-phenyl-propyl}-amide hydrochloride | 565.14 |
| 42 | 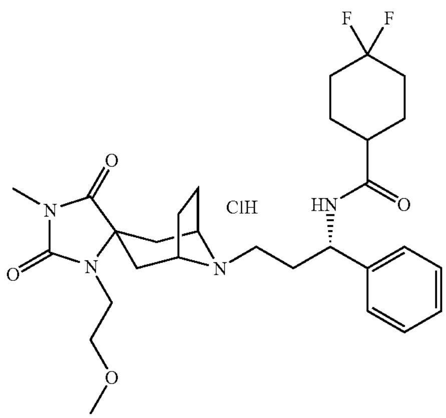 | 4,4-Difluoro-cyclohexanecarboxylic acid {(S)-3-[1-(2-methoxyethyl)-3-methyl-bicyclo[3.2.1]-2,4-dioxo-1β,3,8-triaza-spiro[4.5]dodec-8-yl]-1-phenyl-propyl}-amide hydrochloride | 583.11 |
| 43 | 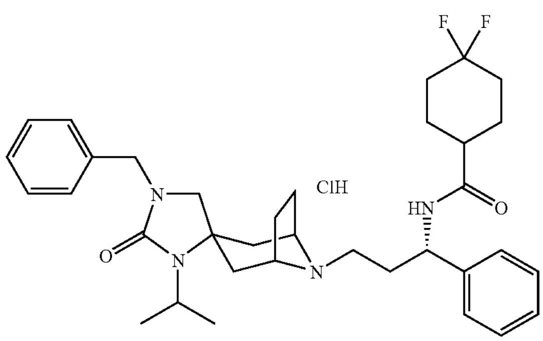 | 4,4-Difluoro-cyclohexanecarboxylic acid {(S)-3-[1-isopropyl-3-benzyl-bicyclo[3.2.1]-2-oxo-1β,3,8-triaza-spiro[4.5]dodec-8-yl]-1-phenyl-propyl}-amide hydrochloride | 629.23 |
| 44 | 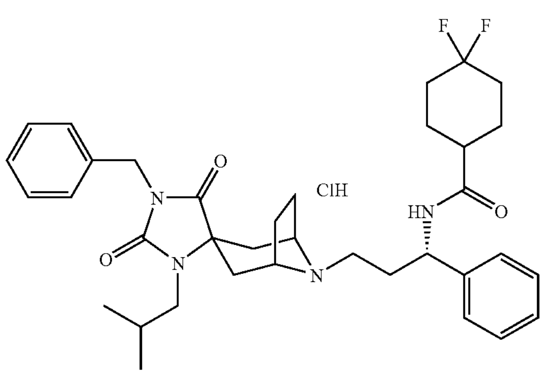 | 4,4-Difluoro-cyclohexanecarboxylic acid {(S)-3-[1-isobutyl-3-benzyl-bicyclo[3.2.1]-2-oxo-1β,3,8-triaza-spiro[4.5]dodec-8-yl]-1-phenyl-propyl}-amide hydrochloride | 657.24 |

TABLE 1-continued

| CPD # | STRUCTURE | COMPOUND NAME | MW |
|---|---|---|---|
| 45 | 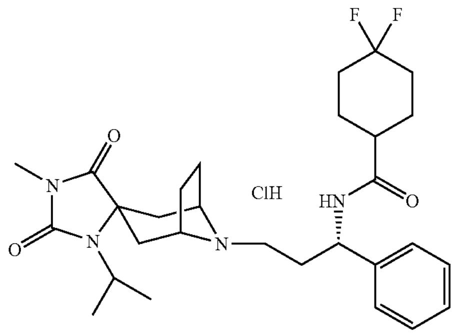 | 4,4-Difluoro-cyclohexanecarboxylic acid {(S)-3-[1-isopropyl-3-methyl-bicyclo[3.2.1]-2-oxo-1β,3,8-triaza-spiro[4.5]dodec-8-yl]-1-phenyl-propyl}-amide hydrochloride | 553.13 |
| 46 | 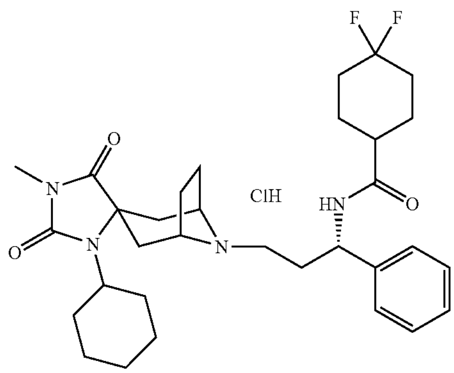 | 4,4-Difluoro-cyclohexanecarboxylic acid {(S)-3-[1-cyclohexyl-3-methyl-bicyclo[3.2.1]-2,4-dioxo-1β,3,8-triaza-spiro[4.5]dodec-8-yl]-1-phenyl-propyl}-amide hydrochloride | 607.18 |
| 47 | 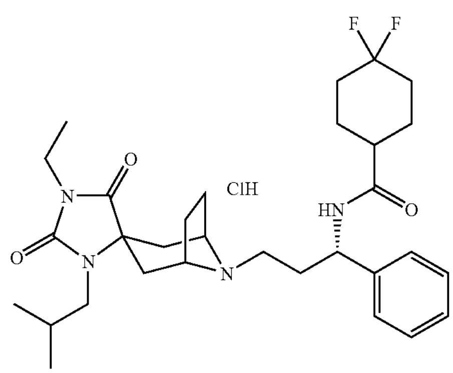 | 4,4-Difluoro-cyclohexanecarboxylic acid {(S)-3-[1-isobutyl-3-ethyl-bicyclo[3.2.1]-2-oxo-1β,3,8-triaza-spiro[4.5]dodec-8-yl]-1-phenyl-propyl}-amide hydrochloride | 581.18 |
| 48 | 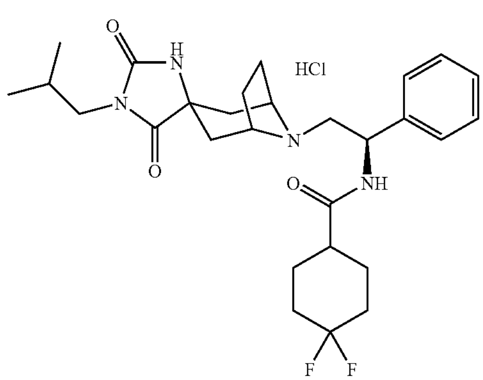 | 4,4-Difluoro-cyclohexanecarboxylic acid {(S)-3-[3-isobutyl-bicyclo[3.2.1]-2,4-dioxo-1α,3,8-triaza-spiro[4.5]dodec-8-yl]-1-phenyl-propyl}-amide hydrochloride | 567.11 |

TABLE 1-continued

| CPD # | STRUCTURE | COMPOUND NAME | MW |
|---|---|---|---|
| 49 | 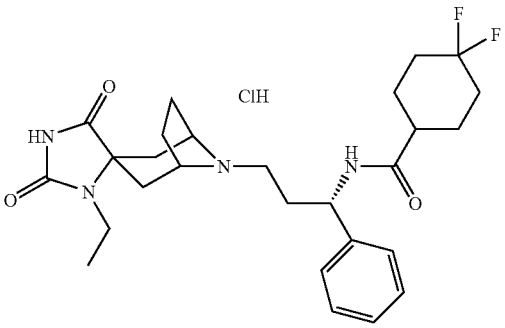 | 4,4-Difluoro-cyclohexanecarboxylic acid {(S)-3-[1-ethyl-bicyclo[3.2.1]-2,4-dioxo-1β,3,8-triaza-spiro[4.5]dodec-8-yl]-1-phenyl-propyl}-amide hydrochloride | 539.06 |
| 50 | 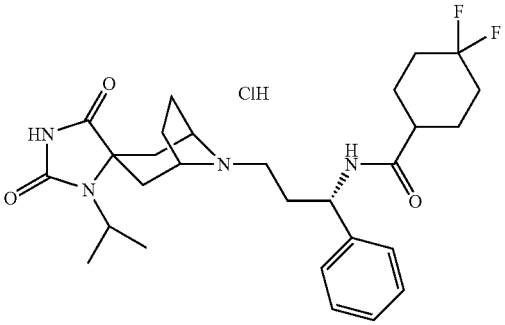 | 4,4-Difluoro-cyclohexanecarboxylic acid {(S)-3-[1-isopropyl-bicyclo[3.2.1]-2,4-dioxo-1β,3,8-triaza-spiro[4.5]dodec-8-yl]-1-phenyl-propyl}-amide hydrochloride | 553.09 |
| 51 | 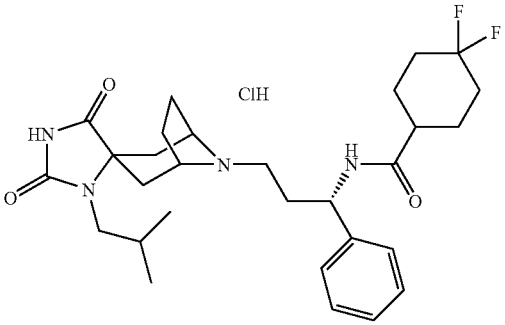 | 4,4-Difluoro-cyclohexanecarboxylic acid {(S)-3-[1-isobutyl-bicyclo[3.2.1]-2,4-dioxo-1β,3,8-triaza-spiro[4.5]dodec-8-yl]-1-phenyl-propyl}-amide hydrochloride | 567.11 |
| 52 | 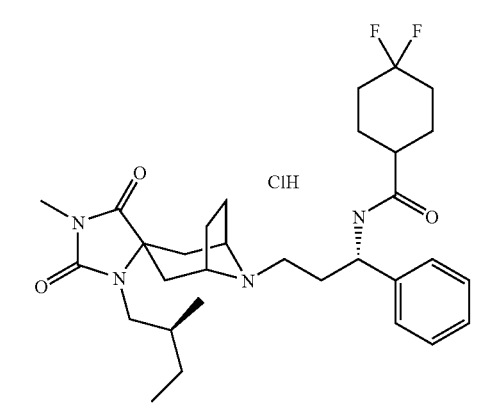 | 4,4-Difluoro-cyclohexanecarboxylic acid {(S)-3-[3-methyl-1-((S)-2-methyl-butyl)-bicyclo[3.2.1]-2,4-dioxo-1β,3,8-triaza-spiro[4.5]dodec-8-yl]-1-phenyl-propyl}-amide hydrochloride | 595.17 |

TABLE 1-continued

| CPD # | STRUCTURE | COMPOUND NAME | MW |
|---|---|---|---|
| 53 | 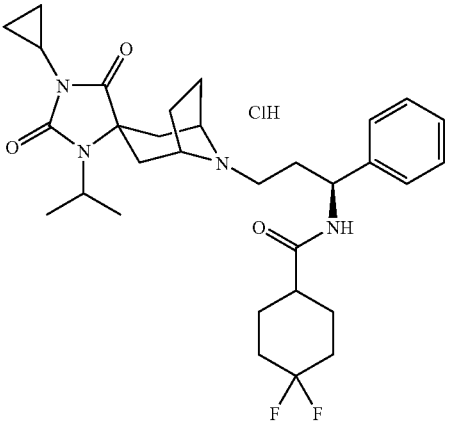 | 4,4-Difluoro-cyclohexanecarboxylic acid {(S)-3-[3-cyclopropyl-1-isopropyl-bicyclo[3.2.1]-2,4-dioxo-1β,3,8-triaza-spiro[4.5]dodec-8-yl]-1-phenyl-propyl}-amide hydrochloride | 593.15 |
| 54 | 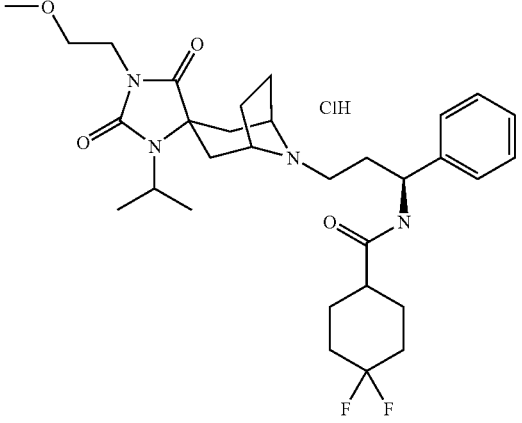 | 4,4-Difluoro-cyclohexanecarboxylic acid {(S)-3-[1-isopropyl-3-(2-methoxy-ethyl)-bicyclo[3.2.1]-2,4-dioxo-1β,3,8-triaza-spiro[4.5]dodec-8-yl]-1-phenyl-propyl}-amide hydrochloride | 611.16 |
| 55 | 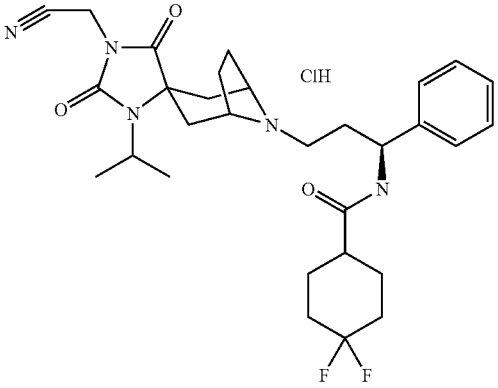 | 4,4-Difluoro-cyclohexanecarboxylic acid {(S)-3-[3-cyanomethyl-1-isopropyl-bicyclo[3.2.1]-2,4-dioxo-1β,3, 8-triaza-spiro[4.5]dodec-8-yl]-1-phenyl-propyl}-amide hydrochloride | 592.12 |

TABLE 1-continued

| CPD # | STRUCTURE | COMPOUND NAME | MW |
|---|---|---|---|
| 56 | 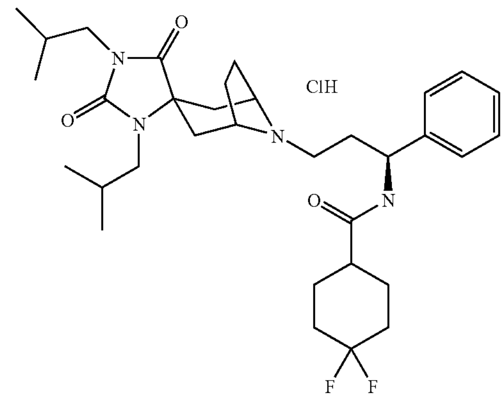 | 4,4-Difluoro-cyclohexanecarboxylic acid {(S)-3-[1,3-diisobutyl-bicyclo[3.2.1]-2,4-dioxo-1β,3,8-triaza-spiro[4.5]dodec-8-yl]-1-phenyl-propyl}-amide hydrochloride | 623.22 |
| 57 | 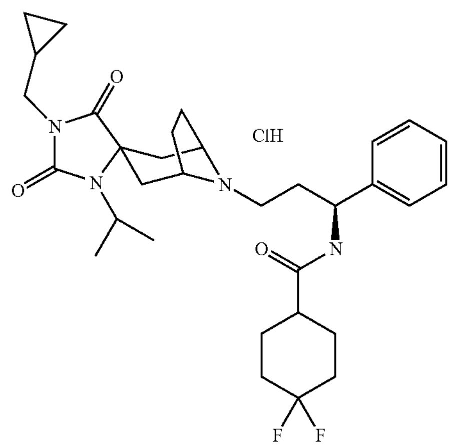 | 4,4-Difluoro-cyclohexanecarboxylic acid {(S)-3-[3-cyclopropylmethyl-1-isopropyl-bicyclo[3.2.1]-2,4-dioxo-1β,3, 8-triaza-spiro[4.5]dodec-8-yl]-1-phenyl-propyl}-amide hydrochloride | 607.18 |
| 58 | 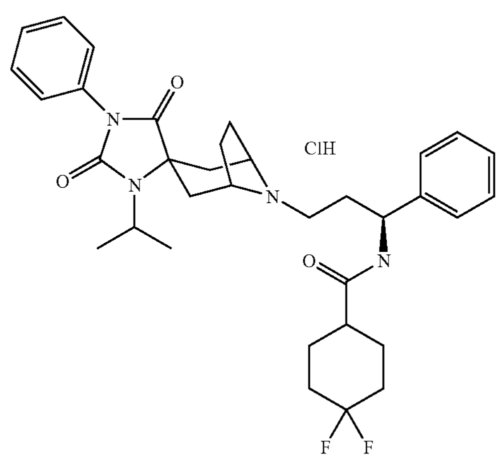 | 4,4-Difluoro-cyclohexanecarboxylic acid {(S)-3-[1-isopropyl-3-phenyl-bicyclo[3.2.1]-2,4-dioxo-1β,3,8-triaza-spiro[4.5]dodec-8-yl]-1-phenyl-propyl}-amide hydrochloride | 629.18 |

TABLE 1-continued

| CPD # | STRUCTURE | COMPOUND NAME | MW |
|---|---|---|---|
| 59 | 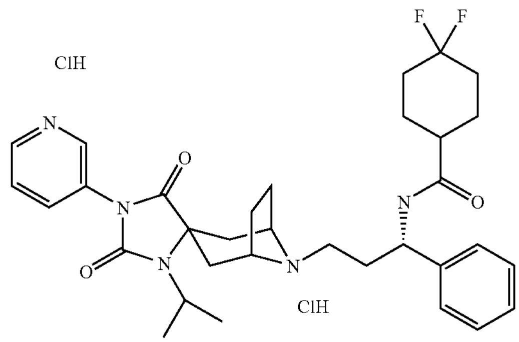 | 4,4-Difluoro-cyclohexanecarboxylic acid {(S)-3-[1-isopropyl-3-pyridin-3-yl-bicyclo[3.2.1]-2,4-dioxo-1β,3,8-triaza-spiro[4.5]dodec-8-yl]-1-phenyl-propyl}-amide dihydrochloride | 666.63 |
| 60 | 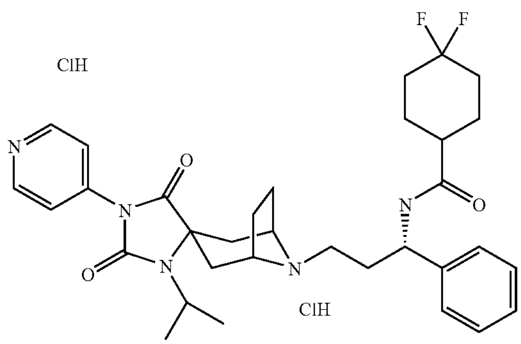 | 4,4-Difluoro-cyclohexanecarboxylic acid {(S)-3-[1-isopropyl-3-pyridin-4-yl-bicyclo[3.2.1]-2,4-dioxo-1β,3,8-triaza-spiro[4.5]dodec-8-yl]-1-phenyl-propyl}-amide dihydrochloride | 666.63 |
| 61 | 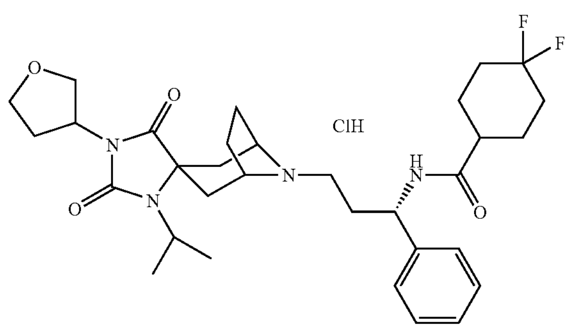 | 4,4-Difluoro-cyclohexanecarboxylic acid {(S)-3-[1-isopropyl-3-(tetrahydro-furan-3-yl)-bicyclo[3.2.1]-2,4-dioxo-1β,3,8-triaza-spiro[4.5]dodec-8-yl]-1-phenyl-propyl}-amide hydrochloride | 623.18 |
| 62 | 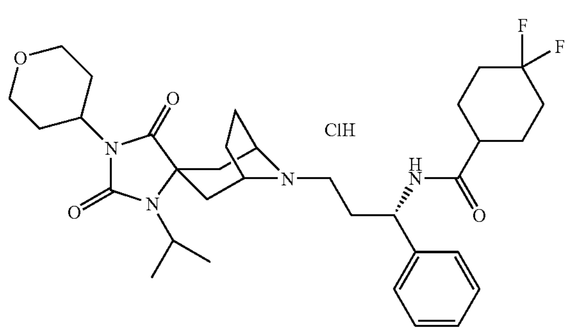 | 4,4-Difluoro-cyclohexanecarboxylic acid {(S)-3-[1-isopropyl-3-(tetrahydro-pyran-4-yl)-bicyclo[3.2.1]-2,4-dioxo-1β,3,8-triaza-spiro[4.5]dodec-8-yl]-1-phenyl-propyl}-amide hydrochloride | 637.2 |

TABLE 1-continued

| CPD # | STRUCTURE | COMPOUND NAME | MW |
|---|---|---|---|
| 63 | 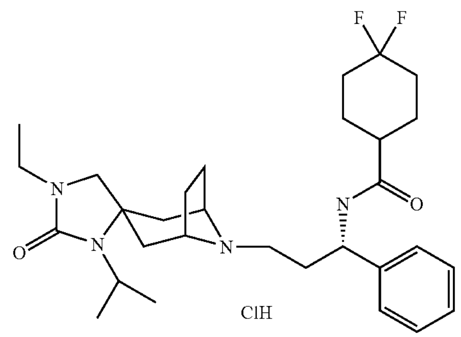 | 4,4-Difluoro-cyclohexanecarboxylic acid {(S)-3-[3-ethyl-1-isopropyl-bicyclo[3.2.1]-2-oxo-1β,3,8-triaza-spiro[4.5]dodec-8-yl]-1-phenyl-propyl}-amide hydrochloride | 567.16 |
| 64 | 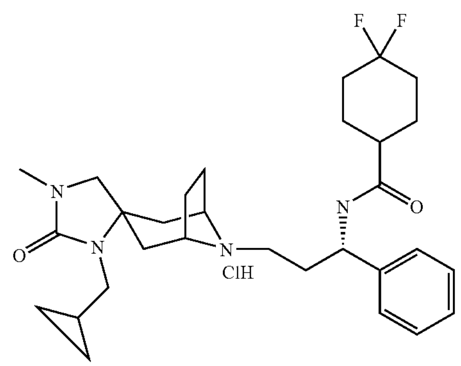 | 4,4-Difluoro-cyclohexanecarboxylic acid {(S)-3-[1-cyclopropylmethyl-3-methyl-bicyclo[3.2.1]-2-oxo-1β,3,8-triaza-spiro[4.5]dodec-8-yl]-1-phenyl-propyl}-amide hydrochloride | 565.14 |
| 65 | 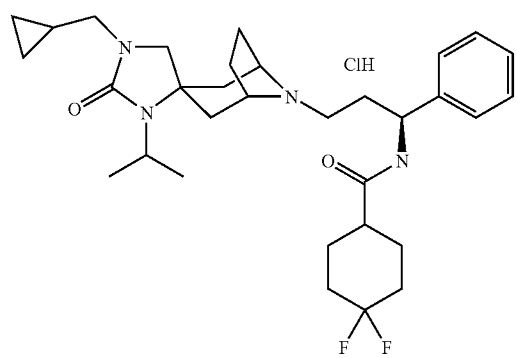 | 4,4-Difluoro-cyclohexanecarboxylic acid {(S)-3-[3-cyclopropylmethyl-1-isopropyl-bicyclo[3.2.1]-2-oxo-1β,3,8-triaza-spiro[4.5]dodec-8-yl]-1-phenyl-propyl}-amide hydrochloride | 593.19 |
| 66 | 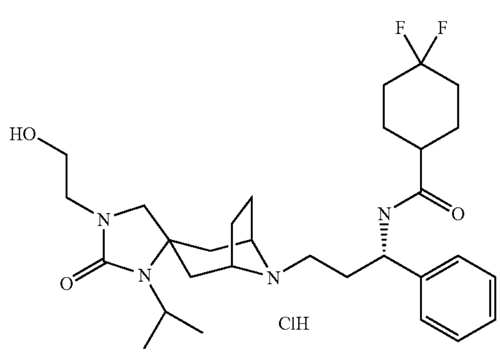 | 4,4-Difluoro-cyclohexanecarboxylic acid {(S)-3-[3-(2-hydroxy-ethyl)-1-isopropyl-bicyclo[3.2.1]-2-oxo-1β,3,8-triaza-spiro[4.5]dodec-8-yl]-1-phenyl-propyl}-amide hydrochloride | 583.15 |

TABLE 1-continued

| CPD # | STRUCTURE | COMPOUND NAME | MW |
|---|---|---|---|
| 67 | 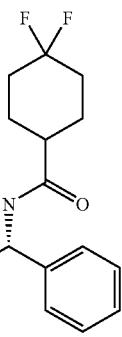 | 4,4-Difluoro-cyclohexanecarboxylic acid {(S)-3-[1-isopropyl-3-(2-methoxy-ethyl)-bicyclo[3.2.1]-2-oxo-1β,3,8-triaza-spiro[4.5]dodec-8-yl]-1-phenyl-propyl}-amide hydrochloride | 597.18 |
| 68 | 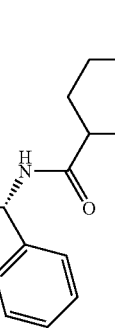 | 4,4-Difluoro-cyclohexanecarboxylic acid {(S)-3-[3-(2-ethoxy-ethyl)-1-isopropyl-bicyclo[3.2.1]-2-oxo-1β,3,8-triaza-spiro[4.5]dodec-8-yl]-1-phenyl-propyl}-amide hydrochloride | 611.22 |
| 69 | 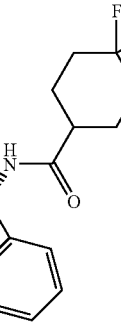 | 4,4-Difluoro-cyclohexanecarboxylic acid {(S)-3-[1-isobutyl-3-(2-methoxy-ethyl)-bicyclo[3.2.1]-2-oxo-1β,3,8-triaza-spiro[4.5]dodec-8-yl]-1-phenyl-propyl}-amide hydrochloride | 611.22 |
| 70 | 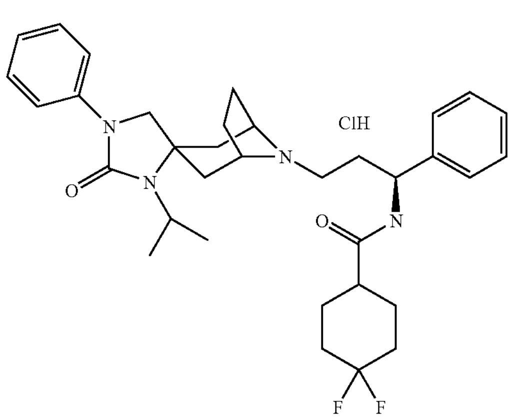 | 4,4-Difluoro-cyclohexanecarboxylic acid {(S)-3-[1-isopropyl-3-phenyl-bicyclo[3.2.1]-2-oxo-1β,3,8-triaza-spiro[4.5]dodec-8-yl]-1-phenyl-propyl}-amide hydrochloride | 615.20 |

TABLE 1-continued

| CPD # | STRUCTURE | COMPOUND NAME | MW |
|---|---|---|---|
| 71 | 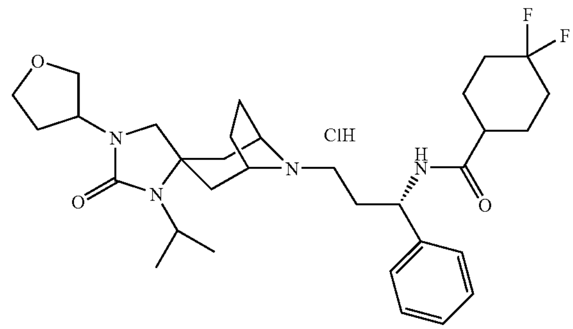 | 4,4-Difluoro-cyclohexanecarboxylic acid {(S)-3-[1-isopropyl-3-(tetrahydro-furan-3-yl)-bicyclo[3.2.1]-2-oxo-1β,3,8-triaza-spiro[4.5]dodec-8-yl]-1-phenyl-propyl}-amide hydrochloride | 609.21 |
| 72 | 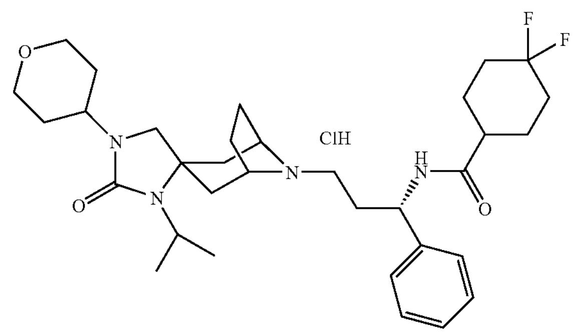 | 4,4-Difluoro-cyclohexanecarboxylic acid {(S)-3-[1-isopropyl-3-(tetrahydro-pyran-4-yl)-bicyclo[3.2.1]-2-oxo-1β,3,8-triaza-spiro[4.5]dodec-8-yl]-1-phenyl-propyl}-amide hydrochloride | 623.22 |

TABLE 2

| CPD # | STRUCTURE | COMPOUND NAME | MW |
|---|---|---|---|
| 73 | 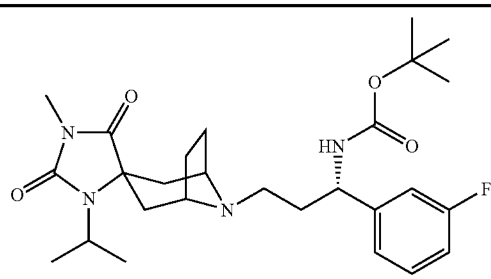 | (S)-1-(3-Fluoro-phenyl)-{3-[1-isopropyl-3-methyl-bicyclo[3.2.1]-2,4-dioxo-1β,3,8-triaza-spiro[4.5]dodec-8-yl]-propyl}-carbamic acid tert-butyl ester | 518.68 |
| 74 | 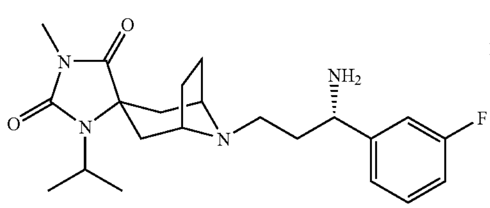 | 8-[(S)-3-Amino-3-(3-fluoro-phenyl)-propyl]-1-isopropyl-3-methyl-bicyclo[3.2.1]-1β,3,8-triaza-spiro[4.5]dodecane-2,4-dione | 418.56 |
| 75 | 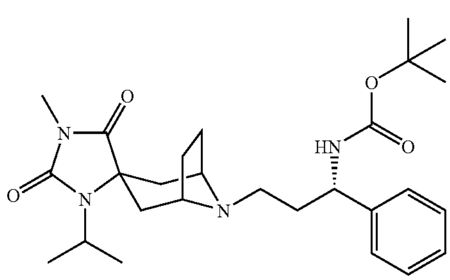 | {(S)-3-[1-Isopropyl-3-methyl-bicyclo[3.2.1]-2,4-dioxo-1β,3,8-triaza-spiro[4.5]dodec-8-yl]-1-phenyl-propyl}-carbamic acid tert-butyl ester | 484.64 |

TABLE 2-continued

| CPD # | STRUCTURE | COMPOUND NAME | MW |
|---|---|---|---|
| 76 | 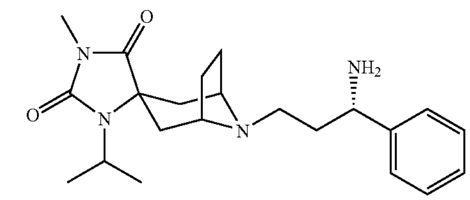 | 8-[(S)-3-Amino-3-phenyl-propyl]-1-isopropyl-3-methyl-bicyclo[3.2.1]-1β,3,8-triaza-spiro[4.5]dodecane-2,4-dione | 384.53 |
| 77 | 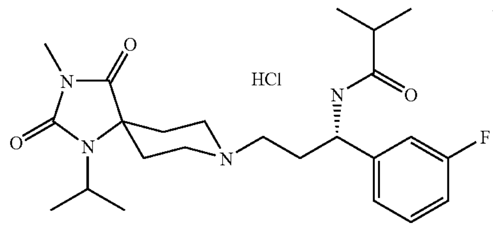 | N-(S)-1-(3-Fluoro-phenyl)-{3-[1-isopropyl-3-methyl-bicyclo[3.2.1]-2,4-dioxo-1β,3,8-triaza-spiro[4.5]dodec-8-yl]-propyl}-isobutyramide hydrochloride | 509.06 |
| 78 | 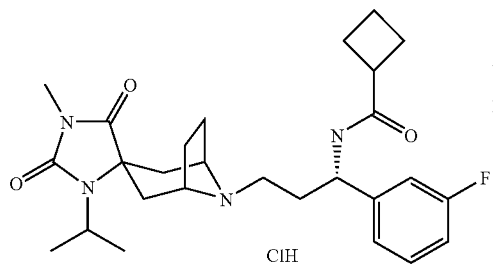 | Cyclobutanecarboxylic acid-(S)-1-(3-fluoro-phenyl)-{3-[1-isopropyl-3-methyl-bicyclo[3.2.1]-2,4-dioxo-1β,3,8-triaza-spiro[4.5]dodec-8-yl]-propyl}-amide hydrochloride | 521.07 |
| 79 | 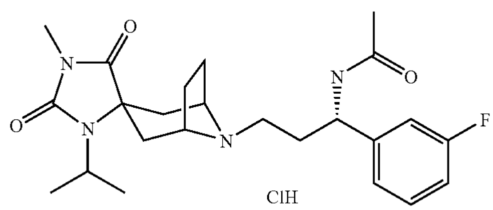 | (S)-1-(3-Fluoro-phenyl)-{3-[1-isopropyl-3-methyl-bicyclo[3.2.1]-2,4-dioxo-1β,3,8-triaza-spiro[4.5]dodec-8-yl]-propyl}-acetamide hydrochloride | 481.01 |
| 80 | 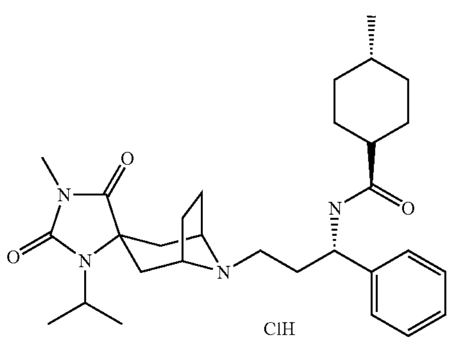 | 4-Methyl-cyclohexanecarboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide hydrochloride | 545.16 |
| 81 | 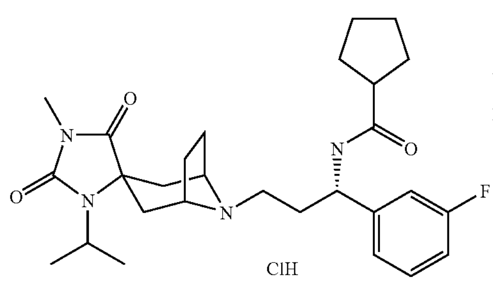 | Cyclopentanecarboxylic acid-(S)-1-(3-fluoro-phenyl)-{3-[1-isopropyl-3-methyl-bicyclo[3.2.1]-2,4-dioxo-1β,3,8-triaza-spiro[4.5]dodec-8-yl]-propyl}-amide hydrochloride | 535.1 |

| CPD # | STRUCTURE | COMPOUND NAME | MW |
|---|---|---|---|
| 82 | 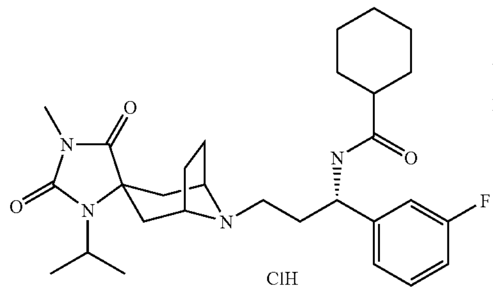 | Cyclohexanecarboxylic acid-(S)-1-(3-fluoro-phenyl)-{3-[1-isopropyl-3-methyl-bicyclo[3.2.1]-2,4-dioxo-1β,3,8-triaza-spiro[4.5]dodec-8-yl]-propyl}-amide hydrochloride | 549.12 |
| 83 | 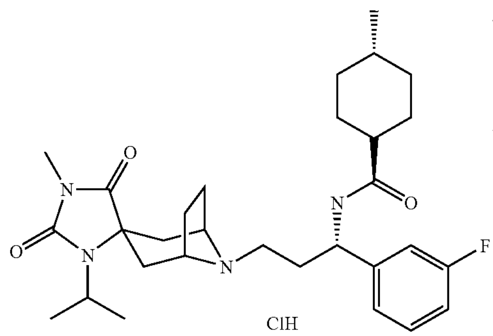 | 4-Methyl-cyclohexanecarboxylic acid-(S)-1-(3-fluoro-phenyl)-{3-[1-isopropyl-3-methyl-bicyclo[3.2.1]-2,4-dioxo-1β,3,8-triaza-spiro[4.5]dodec-8-yl]-propyl}-amide hydrochloride | 563.15 |
| 84 | 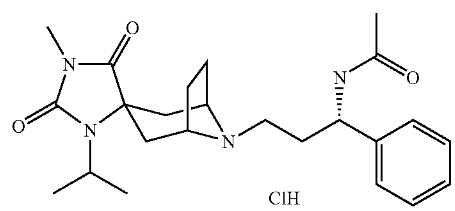 | N-{(S)-3-[1-Isopropyl-3-methyl-bicyclo[3.2.1]-2,4-dioxo-1β,3,8-triaza-spiro[4.5]dodec-8-yl]-1-phenyl-propyl}-acetamide hydrochloride | 463.01 |
| 85 | 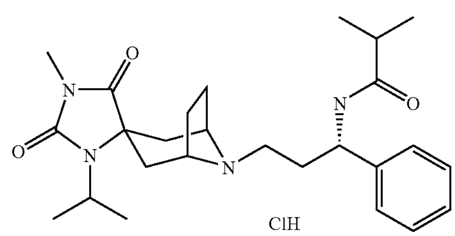 | N-{(S)-3-[1-Isopropyl-3-methyl-bicyclo[3.2.1]-2,4-dioxo-1β,3,8-triaza-spiro[4.5]dodec-8-yl]-1-phenyl-propyl}-isobutyramide hydrochloride | 491.07 |
| 86 | 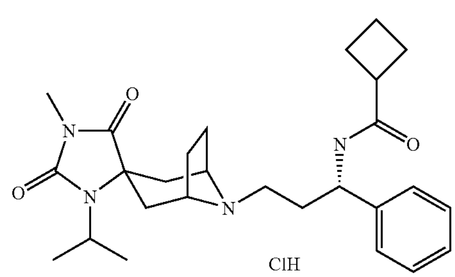 | Cyclobutanecarboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide hydrochloride | 503.08 |

TABLE 2-continued

| CPD # | STRUCTURE | COMPOUND NAME | MW |
|---|---|---|---|
| 87 | 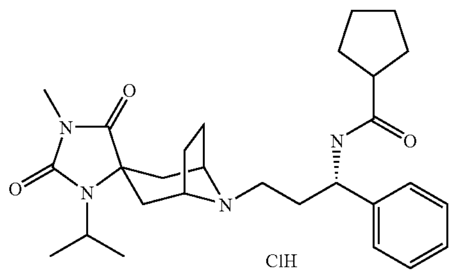 | Cyclopentanecarboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide hydrochloride | 517.11 |
| 88 | 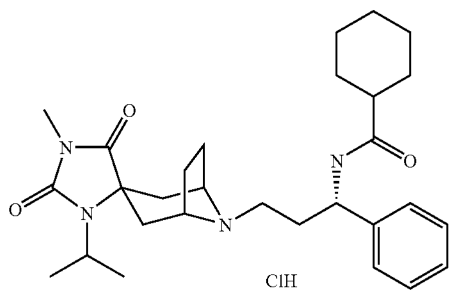 | Cyclohexanecarboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide hydrochloride | 531.13 |
| 89 | 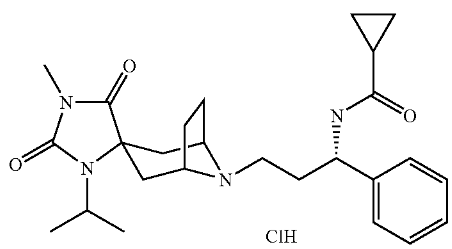 | Cyclopropanecarboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide hydrochloride | 489.05 |
| 90 | 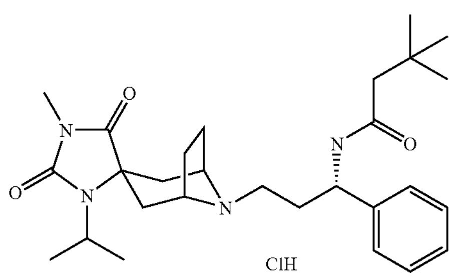 | N-{(S)-3-[1-Isopropyl-3-methyl-bicyclo[3.2.1]-2,4-dioxo-1β,3,8-triaza-spiro[4.5]dodec-8-yl]-1-phenyl-propyl}-3,3-dimethyl-butyramide hydrochloride | 519.12 |
| 91 | 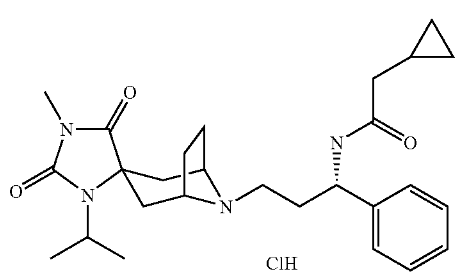 | 2-Cyclopropyl-N-{(S)-3-[1-isopropyl-3-methyl-bicyclo[3.2.1]-2,4-dioxo-1β,3,8-triaza-spiro[4.5]dodec-8-yl]-1-phenyl-propyl}-acetamide hydrochloride | 503.08 |

TABLE 2-continued

| CPD # | STRUCTURE | COMPOUND NAME | MW |
|---|---|---|---|
| 92 | 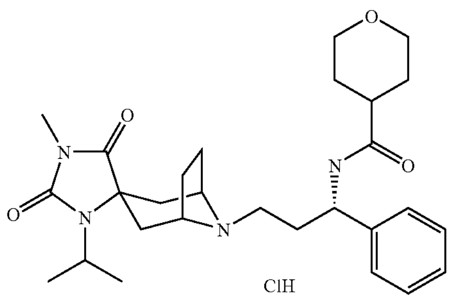 | Tetrahydro-pyran-4-carboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide hydrochloride | 533.1 |
| 93 | 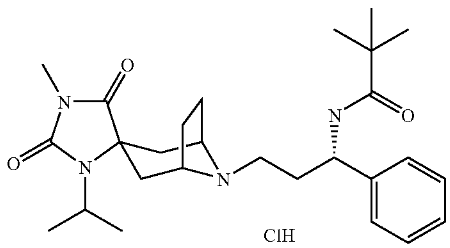 | N-{(S)-3-[1-Isopropyl-3-methyl-bicyclo[3.2.1]-2,4-dioxo-1β,3,8-triaza-spiro[4.5]dodec-8-yl]-1-phenyl-propyl}-2,2-dimethyl-propionamide hydrochloride | 505.09 |
| 94 | 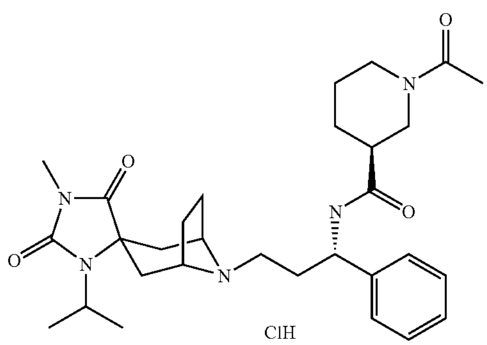 | (S)-1-Acetyl-piperidine-3-carboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide hydrochloride | 574.16 |
| 95 | 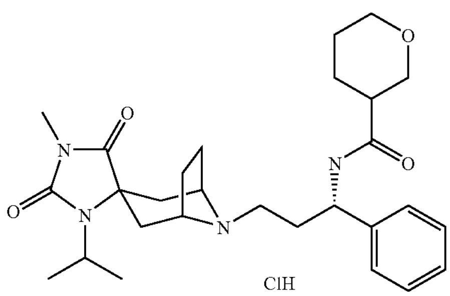 | Tetrahydro-pyran-3-carboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide hydrochloride | 533.11 |
| 96 | 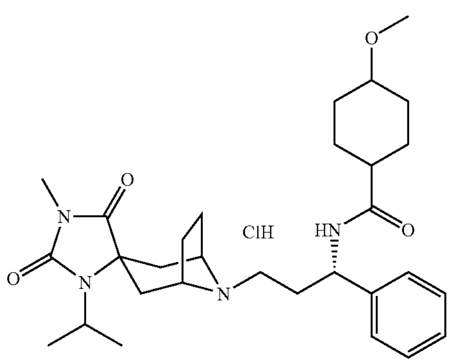 | 4-Methoxy-cyclohexanecarboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide hydrochloride | 561.17 |

TABLE 2-continued

| CPD # | STRUCTURE | COMPOUND NAME | MW |
|---|---|---|---|
| 97 | 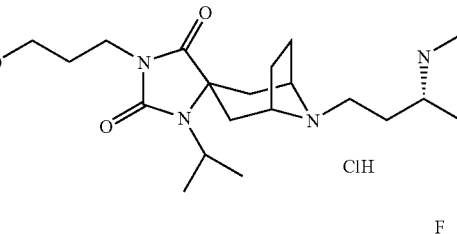 | 4-Trifluoromethyl-cyclohexanecarboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide hydrochloride | 599.14 |

TABLE 3

| CPD # | STRUCTURE | COMPOUND NAME | MW |
|---|---|---|---|
| 98 | 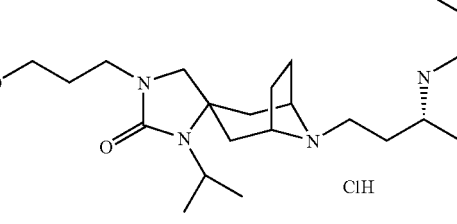 | 4,4-Difluoro-cyclohexanecarboxylic acid {(S)-3-[1-isopropyl-3-(2-methoxy-propyl)-bicyclo[3.2.1]-2,4-dioxo-1β,3,8-triaza-spiro[4.5]dodec-8-yl]-1-phenyl-propyl}-amide hydrochloride | 625.2 |
| 99 | 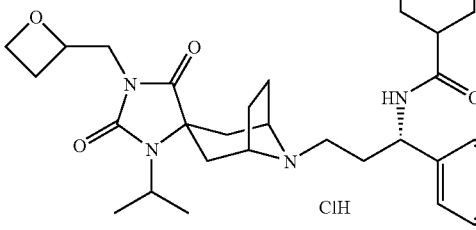 | 4,4-Difluoro-cyclohexanecarboxylic acid {(S)-3-[1-isopropyl-3-(2-methoxy-propyl)-bicyclo[3.2.1]-2-oxo-1β,3,8-triaza-spiro[4.5]dodec-8-yl]-1-phenyl-propyl}-amide hydrochloride | 611.22 |
| 100 | 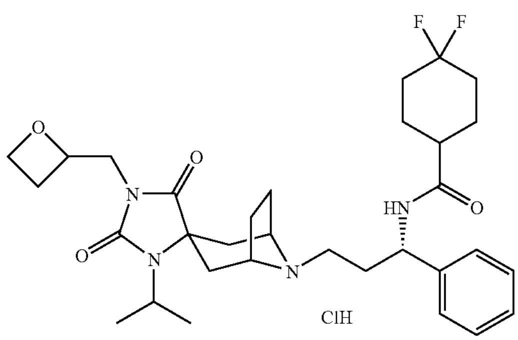 | 4,4-Difluoro-cyclohexanecarboxylic acid {(S)-3-[1-isopropyl-3-oxetan-2-ylmethyl-bicyclo[3.2.1]-2,4-dioxo-1β,3,8-triaza-spiro[4.5]dodec-8-yl]-1-phenyl-propyl}-amide hydrochloride | 623.19 |

TABLE 3-continued

| CPD # | STRUCTURE | COMPOUND NAME | MW |
|---|---|---|---|
| 101 | 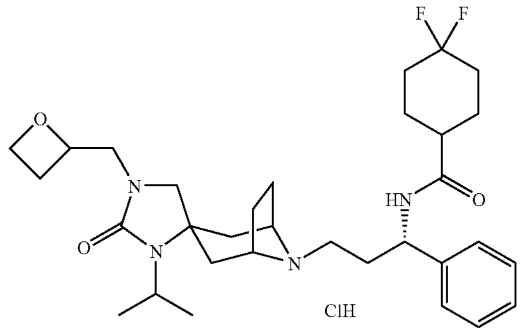 | 4,4-Difluoro-cyclohexanecarboxylic acid {(S)-3-[1-isopropyl-3-oxetan-2-ylmethyl-bicyclo[3.2.1]-2-oxo-1β,3,8-triaza-spiro[4.5]dodec-8-yl]-1-phenyl-propyl}-amide hydrochloride | 609.21 |
| 102 | 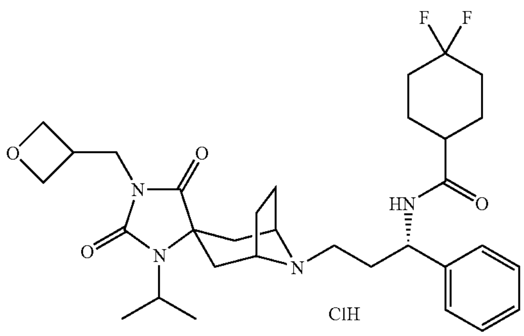 | 4,4-Difluoro-cyclohexanecarboxylic acid {(S)-3-[1-isopropyl-3-oxetan-3-ylmethyl-bicyclo[3.2.1]-2,4-dioxo-1β,3,8-triaza-spiro[4.5]dodec-8-yl]-1-phenyl-propyl}-amide hydrochloride | 623.19 |
| 103 | 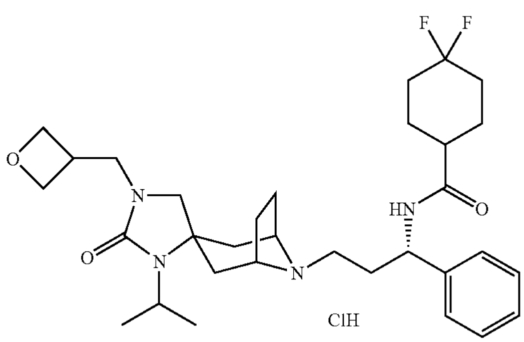 | 4,4-Difluoro-cyclohexanecarboxylic acid {(S)-3-[1-isopropyl-3-oxetan-3-ylmethyl-bicyclo[3.2.1]-2-oxo-1β,3,8-triaza-spiro[4.5]dodec-8-yl]-1-phenyl-propyl}-amide hydrochloride | 609.21 |
| 104 | 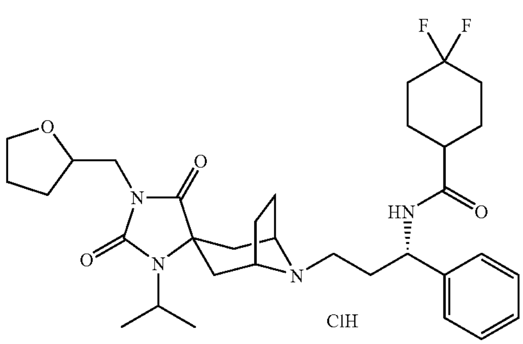 | 4,4-Difluoro-cyclohexanecarboxylic acid {(S)-3-[1-isopropyl-3-(tetrahydro-furan-2-ylmethyl)-bicyclo[3.2.1]-2,4-dioxo-1β,3,8-triaza-spiro[4.5]dodec-8-yl]-1-phenyl-propyl}-amide hydrochloride | 637.22 |

TABLE 3-continued

| CPD # | STRUCTURE | COMPOUND NAME | MW |
|---|---|---|---|
| 105 | 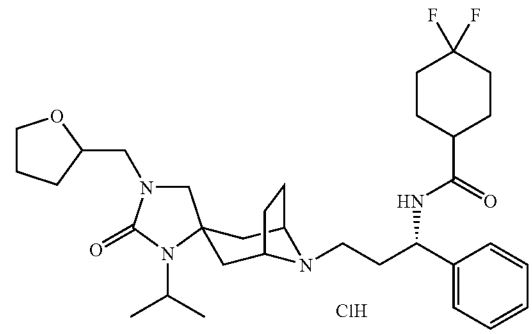 | 4,4-Difluoro-cyclohexanecarboxylic acid {(S)-3-[1-isopropyl-3-(tetrahydro-furan-2-ylmethyl)-bicyclo[3.2.1]-2-oxo-1β,3,8-triaza-spiro[4.5]dodec-8-yl]-1-phenyl-propyl}-amide hydrochloride | 623.23 |
| 106 | 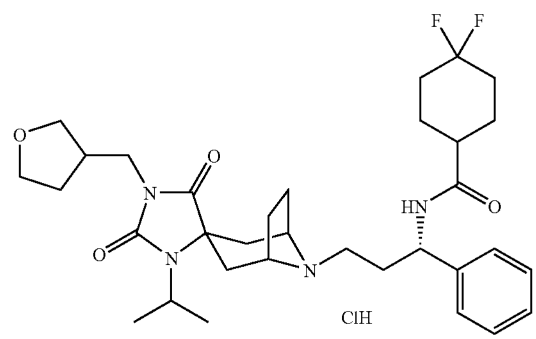 | 4,4-Difluoro-cyclohexanecarboxylic acid {(S)-3-[1-isopropyl-3-(tetrahydro-furan-3-ylmethyl)-bicyclo[3.2.1]-2,4-dioxo-1β,3,8-triaza-spiro[4.5]dodec-8-yl]-1-phenyl-propyl}-amide hydrochloride | 637.22 |
| 107 | 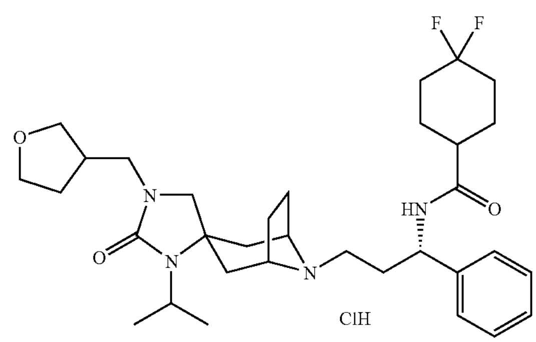 | 4,4-Difluoro-cyclohexanecarboxylic acid {(S)-3-[1-isopropyl-3-(tetrahydro-furan-3-ylmethyl)-bicyclo[3.2.1]-2-oxo-1β,3,8-triaza-spiro[4.5]dodec-8-yl]1-phenyl-propyl}-amide hydrochloride | 623.23 |
| 108 | 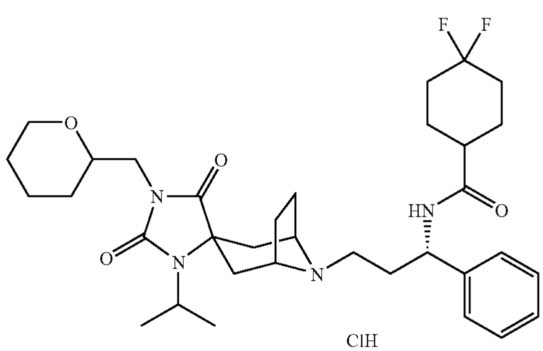 | 4,4-Difluoro-cyclohexanecarboxylic acid {(S)-3-[1-isopropyl-3-(tetrahydro-pyran-2-ylmethyl)-bicyclo[3.2.1]-2,4-dioxo-1β,3,8-triaza-spiro[4.5]dodec-8-yl]-1-phenyl-propyl}-amide hydrochloride | 651.24 |

TABLE 3-continued

| CPD # | STRUCTURE | COMPOUND NAME | MW |
|---|---|---|---|
| 109 | 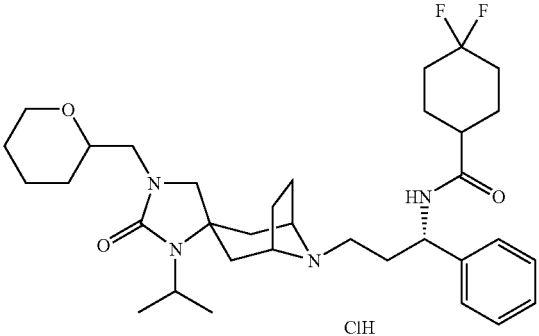 | 4,4-Difluoro-cyclohexanecarboxylic acid {(S)-3-[1-isopropyl-3-(tetrahydro-pyran-2-ylmethyl)-bicyclo[3.2.1]-2-oxo-1β,3,8-triaza-spiro[4.5]dodec-8-yl]-1-phenyl-propyl}-amide hydrochloride | 637.26 |
| 110 | 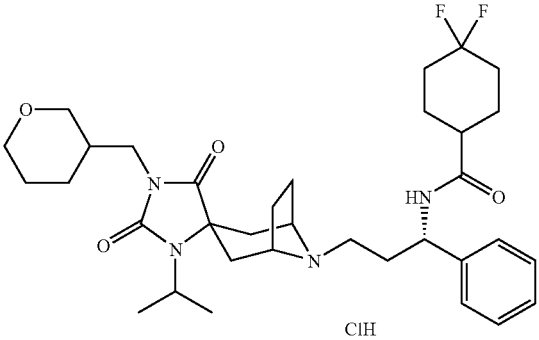 | 4,4-Difluoro-cyclohexanecarboxylic acid {(S)-3-[1-isopropyl-3-(tetrahydro-pyran-3-ylmethyl)-bicyclo[3.2.1]-2,4-dioxo-1β,3,8-triaza-spiro[4.5]dodec-8-yl]-1-phenyl-propyl}-amide hydrochloride | 651.24 |
| 111 | 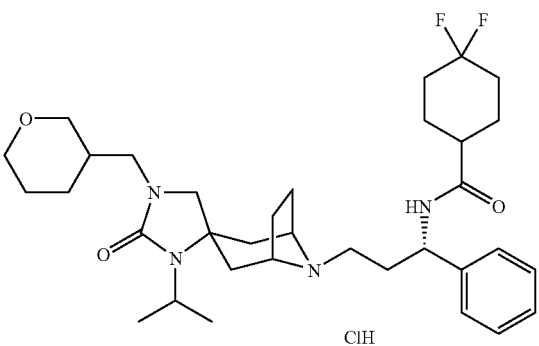 | 4,4-Difluoro-cyclohexanecarboxylic acid {(S)-3-[1-isopropyl-3-(tetrahydro-pyran-3-ylmethyl)-bicyclo[3.2.1]-2-oxo-1β,3,8-triaza-spiro[4.5]dodec-8-yl]-1-phenyl-propyl}-amide hydrochloride | 637.26 |
| 112 | 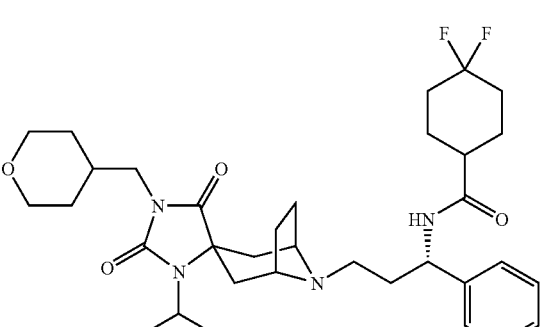 | 4,4-Difluoro-cyclohexanecarboxylic acid {(S)-3-[1-isopropyl-3-(tetrahydro-pyran-4-ylmethyl)-bicyclo[3.2.1]-2,4-dioxo-1β,3,8-triaza-spiro[4.5]dodec-8-yl]-1-phenyl-propyl}-amide hydrochloride | 651.24 |

TABLE 3-continued

| CPD # | STRUCTURE | COMPOUND NAME | MW |
|---|---|---|---|
| 113 | 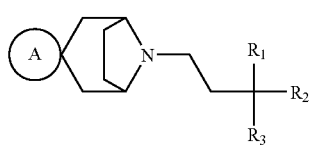 ClH | 4,4-Difluoro-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide hydrochloride | 637.26 |

EXAMPLE 7

Chemokine Binding assay: Membranes (1 µg/well) from human embryonic kidney (HEK-293) cells expressing human CCR5 were incubated with 0.1 nM $^{125}$I-labeled MIP-1α (Amersham) in the presence of varying concentrations of a test compound (10000-0.01 nM) in buffer (50 mM Hepes, pH 7.3/5 mM $MgCl_2$/1 mM $CaCl_2$/0.5% BSA) for 90 min at room temperature. Reaction mixtures (100 µL) were filtered through Multiscreen GFB filters (Millipore) and washed six times with cold wash buffer (50 mM Hepes, pH 7.3/0.5 M NaCl, 0.1% BSA). Bound $^{125}$I-MIP-1α was quantitated by liquid scintillation counting. The nonspecific binding of $^{125}$I-labeled MIP-1α to the membrane was determined based on the radioactivity from the wells added with 100 nM non-radiolabeled MIP-1α. $IC_{50}$ and $K_D$ values were calculated by using GRAPHPAD PRISM software (Intuitive Software for Science, San Diego).

HIV-1 Replication in PBMC Cultures. Isolated PBMC were stimulated in vitro with 5 µg/ml phytohemagglutinin and 50 units/ml IL-2 for 3 days. The cells were resuspended at $4\times10^6$/ml in complete medium (RPMI, 10% FBS/50 units/ml IL-2), seeded into 96-well plates ($2\times10^5$/well), incubated with inhibitor for 1 h at 37° C., and infected in triplicate with 25-100 tissue culture 50% infective dose ($TCID_{50}$) per well of the $R_5$ HIV-1$_{JR-FL}$ strain for 3-4 h. The cells were washed twice in PBS to remove residual virus and cultured in the presence of inhibitor for 4-6 days. HIV-1 replication was determined by the presence of viral RT activity in harvested supernatant fluid. The $IC_{50}$ values for the virus were determined by using GRAPHPAD PRISM software.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound represented by formula (I):

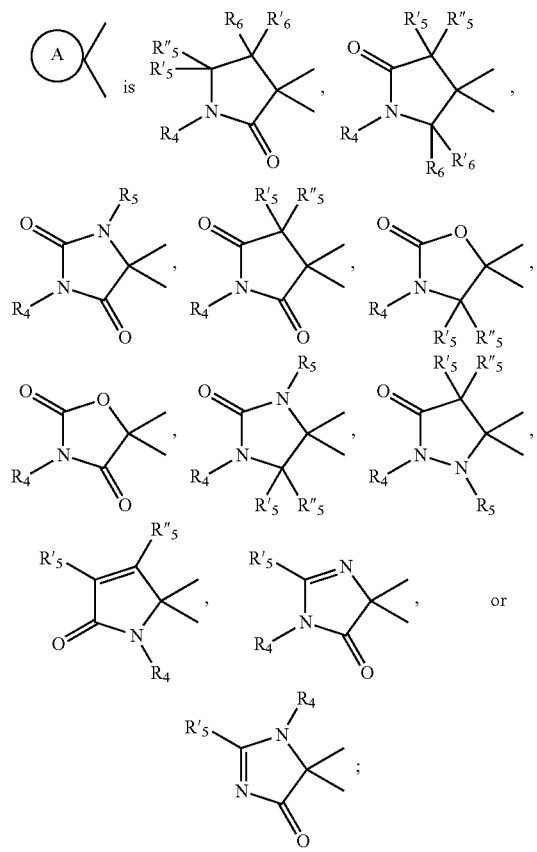

or a pharmaceutically acceptable salt thereof,

Wherein:

A is

[structures shown]

$R_1$ is $NR_7R_9$,

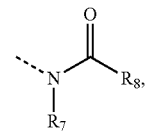
(II)

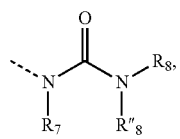
(III)

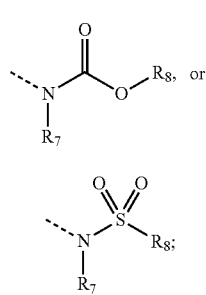

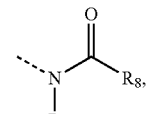

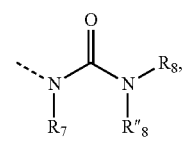

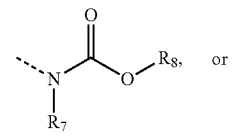

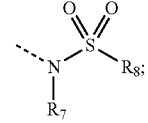

$R_2$ is optionally substituted $C_{1-10}$ alkyl, optionally substituted $C_{2-10}$ alkenyl, optionally substituted $C_{2-10}$ alkynyl, optionally substituted $C_{6-12}$ aryl or optionally substituted 3 to 10 membered heterocycle;

$R_3$ is H, optionally substituted $C_{1-10}$ alkyl or optionally substituted $C_{6-12}$ aryl;

$R_4$, $R_5$, $R'_5$, $R''_5$, $R_6$ and $R'_6$ are each, independently, H, optionally substituted $C_{1-10}$ alkyl, optionally substituted $C_{2-10}$ alkenyl, optionally substituted $C_{2-10}$ alkynyl, optionally substituted $C_{6-12}$ aryl, optionally substituted 3 to 10 membered heterocycle, optionally substituted $C_{7-12}$ aralkyl or optionally substituted 4-16 member heteroaralkyl;

$R_7$ and $R''_8$ are each independently H, optionally substituted $C_{1-10}$ alkyl optionally substituted $C_{2-10}$ alkenyl or optionally substituted $C_{2-10}$ alkynyl;

$R_8$ is H, optionally substituted $C_{1-10}$ alkyl, optionally substituted $C_{2-10}$ alkenyl, optionally substituted $C_{2-10}$ alkynyl, optionally substituted $C_{6-12}$ aryl, optionally substituted 3 to 10 membered heterocycle, optionally substituted or optionally substituted 4-16 member heteroaralkyl; or $R''_8$ and $R_8$ can be taken together to form an optionally substituted 3 to 10 membered heterocycle; and $R_9$ is H or optionally substituted $C_{1-10}$ alkyl.

2. The compound as defined in claim 1, wherein said compound is in the form of the R isomer.

3. The compound as defined in claim 1, wherein said compound is in the form of the S isomer.

4. The compound as defined in claim 1, wherein $R_2$ is unsubstituted phenyl or phenyl substituted with at least one substituent chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, $NR_{63}R_{64}$, $C(O)OR_{62}$, cyano, azido, amidino and guanido; and $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, $C_{7-18}$ aralkyl, or $R_{65}$ and $R_{66}$ are taken together with the oxygen atoms to form a 5 to 10 member heterocycle, or $R_{63}$ and $R_{64}$ are taken together with the nitrogen atom to form a 3 to 10 member heterocycle.

5. The compound of claim 4, wherein $R_2$ is unsubstituted phenyl or phenyl substituted with at least one substituent chosen from a halogen, $C_{1-6}$ alkyl, $C_{1-6}$ alkyloxy, $CF_3$, COOH, $COOC_{1-6}$ alkyl, cyano, $NH_2$, nitro, $NH(C_{1-6}$ alkyl), $N(C_{1-6}$ alkyl)$_2$ and a 3-8 member heterocycle.

6. The compound as defined in claim 1, wherein $R_1$ is chosen from:

$R_7$ is H;

$R_8$ is 3 to 10 membered heterocycle or 4-16 member heteroaralkyl any of which can be unsubstituted or substituted by one or more substituents chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, $NR_{63}R_{64}$, $C(O)OR_{62}$, cyano, azido, amidino and guanido; and $R_{62}$, $R_{65}$, $R_{66}$, $R_{63}$ and $R_{64}$ are each independently chosen from H, $C_{1-12}$alkyl, $C_{2-12}$alkenyl, $C_{2-12}$alkynyl, $C_{6-12}$aryl, 3-10 member heterocycle, 4-16 member heteroaralkyl, and $C_{7-18}$aralkyl, or $R_{65}$ and $R_{66}$ are taken together with the oxygen atoms to form a 5 to 10 member heterocycle, or $R_{63}$ and $R_{64}$ are taken together with the nitrogen atom to form a 3 to 10 member heterocycle.

7. The compound of claim 6, wherein $R_8$ is 3 to 10 membered heterocycle or 4-16 member heteroaralkyl any of which can be unsubstituted or substituted by one or more substituents chosen from halogen, $C_{1-6}$alkyl, $NH_2$, nitro, $C(O)OC_{1-6}$alkyl, COOH, $C_{1-6}$alkyloxy, cyano, and azido.

8. The compound of claim 6, wherein $R_8$ is azetidinyl, pyrrolidinyl, piperazinyl, piperidyl, piperidino, oxetanyl, tetrahydropyranyl, tetrahydrofuranyl, morpholinyl, $CH_2$-azetidinyl,$CH_2$-pyrrolidinyl, $CH_2$-piperazinyl, $CH_2$-piperidyl, $CH_2$-oxetanyl, $CH_2$-tetrahydropyranyl, $CH_2$-tetrahydrofuranyl, $CH_2$-morpholinyl any of which can be unsubstituted or substituted by one or more substituents chosen from halogen, $C_{1-6}$alkyl, $NH_2$, nitro, $C(O)OC_{1-6}$ alkyl, COOH, $C_{1-6}$alkyloxy, cyano, and azido.

9. The compound of claim 1, wherein $R_8$ is $C_{5-7}$ cycloalkyl optionally substituted.

10. The compound of claim 1, wherein $R_8$ is chosen from methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl, any of which can be unsubstituted or substituted by one or more substituents chosen from halogen, nitro, nitroso, $SO_3R_{62}$, $PO_3R_{65}R_{66}$, $CONR_{63}R_{64}$, $C_{1-6}$alkyl, $C_{2-6}$alkenyl, $C_{2-6}$alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, oxo, oxime, $NR_{63}R_{64}$, $C(O)OR_{62}$, cyano, azido, amidino, and guanido; and $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl, or $R_{65}$ and $R_{66}$ are taken together with the oxygen atoms to form a 5 to 10 member heterocycle, or $R_{63}$ and $R_{64}$ are taken together with the nitrogen atom to form a 3 to 10 member heterocycle.

11. The compound according to claim 1, wherein $R_8$ is cyclohexyl, cyclopentyl or cyclobutyl, which in each case is unsubstituted or substituted by one or more substituents independently chosen from halogen, nitro, nitroso, $SO_3Rf$, $SO_2Rf$, $PO_3R_{65}R_{66}$, CONRgRh, $C_{1-6}$ alkyl, $C_{7-18}$ aralkyl, $C_{6-12}$ aryl, $C_{1-6}$ alkyloxy, $C_{6-12}$ aryloxy, $C(O)C_{1-6}$ alkyl, $C(O)C_{6-12}$ aryl, $C(O)C_{7-12}$ aralkyl, C(O)NHRf, 3-10 member heterocycle, 4-16 member heteroaralkyl, hydroxyl, oxo, oxime, NRgRh, C(O)ORf, cyano, azido, amidino and guanido; and Rf, $R_{65}$, $R_{66}$, Rg and Rh in each case are independently H, $C_{1-6}$ alkyl, $C_{2-6}$ alkenyl, $C_{2-6}$ alkynyl, $C_{6-12}$ aryl, 3-10 member heterocycle, 4-16 member heteroaralkyl, or $C_{7-18}$ aralkyl.

12. A compound according to claim 1, wherein Said compound is represented by formula (Ia):

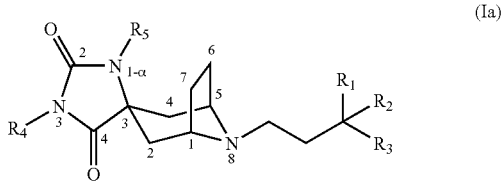

(Ia)

or is a pharmaceutically acceptable salt thereof.

13. A compound according to claim 1, wherein Said compound is represented by formula (Ib):

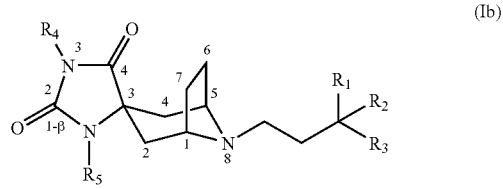

(Ib)

or is a pharmaceutically acceptable salt thereof.

14. A compound according to claim 1, wherein said compound is represented by formula (Ic) and (Ic'):

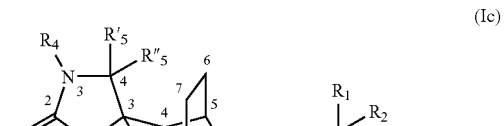

(Ic)

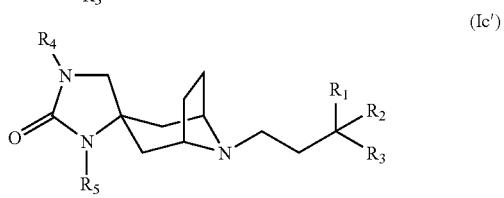

(Ic')

or pharmaceutically acceptable salts thereof.

15. A compound according to claim 1, wherein said compound is represented by formula (Id) and (Id'):

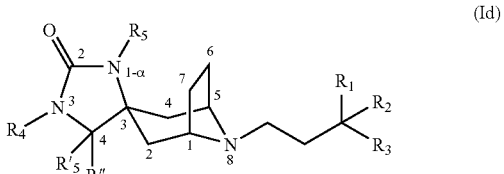

(Id)

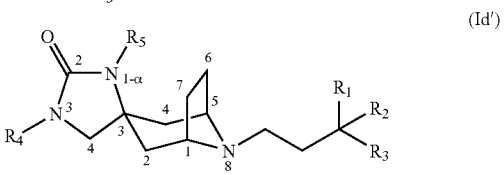

(Id')

or is a pharmaceutically acceptable salt thereof.

16. The compound according to claim 1, wherein $R_4$ or $R_5$ is optionally substituted $C_{1-10}$ alkyl, optionally substituted $C_{7-12}$ aralkyl, optionally substituted $C_{6-12}$ aryl, optionally substituted 3 to 10 membered heterocycle or optionally substituted 4-16 member heteroaralkyl.

17. The compound according to claim 16, wherein $R_4$ or $R_5$ is $C_{6-12}$ aryl, $C_{7-12}$ aralkyl, 3 to 10 membered heterocycle or 4-16 member heteroaralkyl, which in each case are unsubstituted or substituted by one or more substituents chosen from a halogen, $C_{1-6}$ alkyl, $C_{1-6}$ alkyloxy, $CF_3$, COOH, $COOC_{1-6}$ alkyl, cyano, $NH_2$, nitro, $NH(C_{1-6}$ alkyl), $N(C_{1-6}$ alkyl$)_2$ and a 3-8 member heterocycle.

18. The compound according to claim 16, wherein $R_4$ or $R_5$ is phenyl or benzyl which are unsubstituted or substituted by one or more substituents chosen from halogen, nitro, $CONR_{63}R_{64}$, $C_{1-6}$ alkyl, $C_{2-6}$ alkenyl, $C_{1-6}$ alkyloxy, $C_{2-6}$ alkenyloxy, $C_{2-6}$ alkynyloxy, $C_{6-12}$ aryl, 3-10 member heterocycle, 4-16 member heteroaralkyl, hydroxyl, $NR_{63}R_{64}$, $C(O)OR_{62}$, cyano, and azido; and $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen to form a 3 to 10 member heterocycle.

19. The compound according to claim 16, wherein
$R_4$ or $R_5$ are independently phenyl or benzyl which are unsubstituted or substituted by one or more substituents chosen from halogen, $C_{1-6}$ alkyl, $NR_{63}R_{64}$, nitro, $CONR_{63}R_{64}$, $C_{1-6}$ alkyloxy, $C(O)OR_{62}$, cyano, and azido; and $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen to form a 3 to 10 member heterocycle.

20. The compound according to claim 16, wherein $R_4$ or $R_5$ are independently chosen from phenyl, benzyl, pyridinyl, thiophenyl, benzofuran, thiazole, and pyrazole, which are unsubstituted or substituted by one or more substituents chosen from a halogen, $C_{1-6}$ alkyl, $C_{1-6}$ alkyloxy, $CF_3$, COOH, $COOC_{1-6}$ alkyl, cyano, $NH_2$, nitro, $NH(C_{1-6}$ alkyl), $N(C_{1-6}$ alkyl)$_2$ and a 3-8 member heterocycle.

21. The compound according to claim 16, wherein $R_4$ or $R_5$ are independently benzyl unsubstituted or substituted by one or more substituents chosen from halogen, $C_{1-3}$ alkoxy, $SO_2C_{1-3}$alkyl, difluoromethoxy, trifluoromethoxy, trifluoromethyl, CN and pyrazoyl.

22. The compound according to claim 16, wherein
$R_4$ or $R_5$ are independently azetidinyl, pyrrolidinyl, piperazinyl, piperidyl, piperidino, oxetanyl, tetrahydropyranyl, tetrahydrofuranyl, morpholinyl, $CH_2$-azetidinyl, $CH_2$-pyrrolidinyl, $CH_2$-piperazinyl, $CH_2$-piperidyl, $CH_2$-oxetanyl, $CH_2$-tetrahydropyranyl, $CH_2$-tetrahydrofuranyl, or $CH_2$-morpholinyl any of which can be unsubstituted or substituted by one or more substituents chosen fromc halogen, $C_{1-6}$ alkyl, $NR_{63}R_{64}$, nitro, $CONR_{63}R_{64}$, $C_{1-6}$ alkyloxy, $C(O)OR_{62}$, cyano, and azido; and $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen to form a 3 to 10 member heterocycle.

23. The compound according to claim 16, wherein $R_4$ or $R_5$ are independently azetidinyl, pyrrolidinyl, piperazinyl, piperidyl, piperidino, oxetanyl, tetrahydropyranyl, tetrahydrofuranyl, morpholinyl, $CH_2$-azetidinyl, $CH_2$-pyrrolidinyl, $CH_2$-piperazinyl, $CH_2$-piperidyl, $CH_2$-oxetanyl, $CH_2$-tetrahydropyranyl, $CH_2$-tetrahydrofuranyl, or $CH_2$-morpholinyl, which in each case is unsubstituted or substituted by one or more substituents chosen from a halogen, $C_{1-6}$ alkyl, $C_{1-6}$ alkyloxy, $CF_3$, COOH, $COOC_{1-6}$alkyl, cyano, $NH_2$, nitro, $NH(C_{1-6}$ alkyl), $N(C_{1-6}$ alkyl)$_2$ and a 3-8 member heterocycle.

24. The compound according to claim 16, wherein $R_4$ or $R_5$ are independently oxetanyl, tetrahydropyranyl, tetrahydrofuranyl, morpholinyl, $CH_2$-oxetanyl, $CH_2$-tetrahydropyranyl, or $CH_2$-tetrahydrofuranyl, any of which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido.

25. The compound according to claim 16, wherein $R_4$ or $R_5$ is $CH_2$-oxetanyl, $CH_2$-tetrahydropyranyl, $CH_2$-tetrahydrofuranyl which in each case is unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido.

26. The compound according to claim 16, wherein
$R_4$ or $R_5$ is chosen from methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl, which in each case is unsubstituted or substituted by one or more substituents chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)$ $C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, oxo, oxime, $NR_{63}R_{64}$, $C(O)OR_{62}$, cyano, azido, amidino and guanido; and $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl, or $R_{65}$ and $R_{66}$ are taken together with the oxygen atoms to form a 5 to 10 member heterocycle, or $R_{63}$ and $R_{64}$ are taken together with the nitrogen atom to form a 3 to 10 member.

27. The compound according to claim 16, wherein $R_4$ or $R_5$ is unsubstituted methyl or methyl substituted by one or more halogens.

28. The compound according to claim 16, wherein $R_4$ or $R_5$ is unsubstituted methyl or methyl substituted by one or more fluoro.

29. The compound according to claim 16, wherein $R_4$ or $R_5$ is chosen from methyl, ethyl, vinyl, propyl, propenyl, isopropyl, butyl, isobutyl, pentyl, neopentyl, or tert-butyl.

30. The compound according to claim 16, wherein $R_4$ or $R_5$ are independently isopropyl or isobutyl.

31. The compound according to claim 1, wherein
$R'_5$, $R''_5$, $R_6$, $R'_6$, $R_7$ and $R''_8$ are independently H, unsubstituted $C_{1-12}$ alkyl, or $C_{1-12}$ alkyl substituted by one or more substituents chosen from halogen, nitro, nitroso, $SO_3R_{62}$, $PO_3R_{65}R_{66}$, $CONR_{63}R_{64}$, $C_{1-6}$alkyl, $C_{2-6}$alkenyl, $C_{2-6}$alkynyl, $C_{7-12}$aralkyl, $C_{6-12}$aryl, $C_{1-6}$ alkyloxy, $C_{2-6}$ alkenyloxy, $C_{2-6}$ alkynyloxy, $C_{6-12}$ aryloxy, $C(O)$ $C_{1-6}$ alkyl, $C(O)C_{2-6}$ alkenyl, $C(O)C_{2-6}$ alkynyl, $C(O)$ $C_{6-12}$ aryl, $C(O)C_{7-12}$ aralkyl, 3-10 member heterocycle, 4-16 member heteroaralkyl, hydroxyl, oxo, oxime, $NR_{63}R_{64}$, $C(O)OR_{62}$, cyano, azido, amidino and guanido; and $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 4-10 member heterocycle, 4-16 member heteroaralkyl, and $C_{7-18}$ aralkyl, or $R_{65}$ and $R_{66}$ are taken together with the oxygen atoms to form a 5 to 10 member heterocycle, or $R_{63}$ and $R_{64}$ are taken together with the nitrogen atom to form a 3 to 10 member heterocycle.

32. A method for the treatment of HIV infection in a subject comprising administering to the subject a therapeutically effective amount of a compound according to claim 1.

33. A method for blocking cellular entry of HIV in a subject comprising administering to the subject in need thereof an effective amount of a compound according to claim 1 to block HIV from cellular entry in said subject.

34. A pharmaceutical formulation comprising a compound according to claim 1 in combination with a pharmaceutically acceptable carrier or excipient.

35. A compound selected from:

| | |
|---|---|
| 1 | 4,4-Difluoro-cyclohexanecarboxylic acid {(S)-3-[3-(4-methanesulfonyl-benzyl)-bicyclo[3.2.1]-2,4-dioxo-1β,3,8-triaza-spiro[4.5]dodec-8-yl]-1-phenyl-propyl}-amide; |
| 2 | 4,4-Difluoro-cyclohexanecarboxylic acid {(S)-3-[bicyclo[3.2.1]-2,4-dioxo-1α,3,8-triaza-spiro[4.5]dodec-8-yl]-1-phenyl-propyl}-amide; |

| # | Compound |
|---|---|
| 3 | 4,4-Difluoro-cyclohexanecarboxylic acid {(S)-3-[3-ethyl-bicyclo[3.2.1]-2,4-dioxo-1α,3,8-triaza-spiro[4.5]dodec-8-yl]-1-phenyl-propyl}-amide; |
| 4 | 4,4-Difluoro-cyclohexanecarboxylic acid {(S)-3-[1,3-diethyl-bicyclo[3.2.1]-2,4-dioxo-1α,3,8-triaza-spiro[4.5]dodec-8-yl]-1-phenyl-propyl}-amide; |
| 5 | 4,4-Difluoro-cyclohexanecarboxylic acid {(S)-3-[bicyclo[3.2.1]-2,4-dioxo-1β,3,8-triaza-spiro[4.5]dodec-8-yl]-1-phenyl-propyl}-amide; |
| 6 | 4,4-Difluoro-cyclohexanecarboxylic acid {(S)-3-[3-ethyl-bicyclo[3.2.1]-2,4-dioxo-1β,3,8-triaza-spiro[4.5]dodec-8-yl]-1-phenyl-propyl}-amide; |
| 7 | 4,4-Difluoro-cyclohexanecarboxylic acid {(S)-3-[1,3-diethyl-bicyclo[3.2.1]-2,4-dioxo-1β,3,8-triaza-spiro[4.5]dodec-8-yl]-1-phenyl-propyl}-amide; |
| 8 | 4,4-Difluoro-cyclohexanecarboxylic acid {(S)-3-[3-(4-dimethylsulfamoyl-benzyl)-bicyclo[3.2.1]-2,4-dioxo-1α,3,8-triaza-spiro[4.5]dodec-8-yl]-1-phenyl-propyl}-amide; |
| 9 | 4,4-Difluoro-cyclohexanecarboxylic acid {(S)-3-[3-(4-methanesulfonyl-benzyl)-bicyclo[3.2.1]-2,4-dioxo-1α,3,8-triaza-spiro[4.5]dodec-8-yl]-1-phenyl-propyl}-amide; |
| 10 | 4,4-Difluoro-cyclohexanecarboxylic acid {(S)-3-[1-ethyl-3-(4-methanesulfonyl-benzyl)-bicyclo[3.2.1]-2,4-dioxo-1β,3,8-triaza-spiro[4.5]dodec-8-yl]-1-phenyl-propyl}-amide; |
| 11 | 4,4-Difluoro-cyclohexanecarboxylic acid {(S)-3-[1,3-dimethyl-bicyclo[3.2.1]-2,4-dioxo-1β,3,8-triaza-spiro[4.5]dodec-8-yl]-1-phenyl-propyl}-amide; |
| 12 | 4,4-Difluoro-cyclohexanecarboxylic acid {(S)-3-[1-ethyl-3-methyl-bicyclo[3.2.1]-2,4-dioxo-1β,3,8-triaza-spiro[4.5]dodec-8-yl]-1-phenyl-propyl}-amide; |
| 13 | 4,4-Difluoro-cyclohexanecarboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide; |
| 14 | 4,4-Difluoro-cyclohexanecarboxylic acid {(S)-3-[1-propyl-3-methyl-bicyclo[3.2.1]-2,4-dioxo-1β,3,8-triaza-spiro[4.5]dodec-8-yl]-1-phenyl-propyl}-amide; |
| 15 | 4,4-Difluoro-cyclohexanecarboxylic acid {(S)-3-[1-isobutyl-3-methyl-bicyclo[3.2.1]-2,4-dioxo-1β,3,8-triaza-spiro[4.5]dodec-8-yl]-1-phenyl-propyl}-amide; |
| 16 | 4,4-Difluoro-cyclohexanecarboxylic acid {(S)-3-[1-cyclopropylmethyl-3-methyl-bicyclo[3.2.1]-2,4-dioxo-1β,3,8-triaza-spiro[4.5]dodec-8-yl]-1-phenyl-propyl}-amide; |
| 17 | 4,4-Difluoro-cyclohexanecarboxylic acid {(S)-3-[1-cyclohexylmethyl-3-methyl-bicyclo[3.2.1]-2,4-dioxo-1β,3,8-triaza-spiro[4.5]dodec-8-yl]-1-phenyl-propyl}-amide; |
| 18 | 4,4-Difluoro-cyclohexanecarboxylic acid {(S)-3-[1-benzyl-3-methyl-bicyclo[3.2.1]-2,4-dioxo-1β,3,8-triaza-spiro[4.5]dodec-8-yl]-1-phenyl-propyl}-amide; |
| 19 | 4,4-Difluoro-cyclohexanecarboxylic acid {(S)-3-[3-ethyl-1-methyl-bicyclo[3.2.1]-2,4-dioxo-1β,3,8-triaza-spiro[4.5]dodec-8-yl]-1-phenyl-propyl}-amide; |
| 20 | 4,4-Difluoro-cyclohexanecarboxylic acid {(S)-3-[3-ethyl-1-isopropyl-bicyclo[3.2.1]-2,4-dioxo-1β,3,8-triaza-spiro[4.5]dodec-8-yl]-1-phenyl-propyl}-amide; |
| 21 | 4,4-Difluoro-cyclohexanecarboxylic acid {(S)-3-[3-ethyl-1-propyl-bicyclo[3.2.1]-2,4-dioxo-1β,3,8-triaza-spiro[4.5]dodec-8-yl]-1-phenyl-propyl}-amide; |
| 22 | 4,4-Difluoro-cyclohexanecarboxylic acid {(S)-3-[3-ethyl-1-isobutyl-bicyclo[3.2.1]-2,4-dioxo-1β,3,8-triaza-spiro[4.5]dodec-8-yl]-1-phenyl-propyl}-amide; |
| 23 | 4,4-Difluoro-cyclohexanecarboxylic acid {(S)-3-[1-cyclopropylmethyl-3-ethyl-bicyclo[3.2.1]-2,4-dioxo-1β,3,8-triaza-spiro[4.5]dodec-8-yl]-1-phenyl-propyl}-amide; |
| 24 | 4,4-Difluoro-cyclohexanecarboxylic acid {(S)-3-[1-cyclohexylmethyl-3-ethyl-bicyclo[3.2.1]-2,4-dioxo-1β,3,8-triaza-spiro[4.5]dodec-8-yl]-1-phenyl-propyl}-amide; |
| 25 | 4,4-Difluoro-cyclohexanecarboxylic acid {(S)-3-[1-benzyl-3-ethyl-bicyclo[3.2.1]-2,4-dioxo-1β,3,8-triaza-spiro[4.5]dodec-8-yl]-1-phenyl-propyl}-amide; |
| 26 | 4,4-Difluoro-cyclohexanecarboxylic acid {(S)-3-[1-methyl-3-isopropyl-bicyclo[3.2.1]-2,4-dioxo-1β,3,8-triaza-spiro[4.5]dodec-8-yl]-1-phenyl-propyl}-amide; |
| 27 | 4,4-Difluoro-cyclohexanecarboxylic acid {(S)-3-[1-ethyl-3-isopropyl-bicyclo[3.2.1]-2,4-dioxo-1β,3,8-triaza-spiro[4.5]dodec-8-yl]-1-phenyl-propyl}-amide; |
| 28 | 4,4-Difluoro-cyclohexanecarboxylic acid {(S)-3-[1,3-diisopropyl-bicyclo[3.2.1]-2,4-dioxo-1β,3,8-triaza-spiro[4.5]dodec-8-yl]-1-phenyl-propyl}-amide; |
| 29 | 4,4-Difluoro-cyclohexanecarboxylic acid {(S)-3-[1-propyl-3-isopropyl-bicyclo[3.2.1]-2,4-dioxo-1β,3,8-triaza-spiro[4.5]dodec-8-yl]-1-phenyl-propyl}-amide; |
| 30 | 4,4-Difluoro-cyclohexanecarboxylic acid {(S)-3-[1-isobutyl-3-isopropyl-bicyclo[3.2.1]-2,4-dioxo-1β,3,8-triaza-spiro[4.5]dodec-8-yl]-1-phenyl-propyl}-amide; |
| 31 | 4,4-Difluoro-cyclohexanecarboxylic acid {(S)-3-[1-cyclopropylmethyl-3-isopropyl-bicyclo[3.2.1]-2,4-dioxo-1β,3,8-triaza-spiro[4.5]dodec-8-yl]-1-phenyl-propyl}-amide; |
| 32 | 4,4-Difluoro-cyclohexanecarboxylic acid {(S)-3-[1-cyclohexylmethyl-3-isopropyl-bicyclo[3.2.1]-2,4-dioxo-1β,3,8-triaza-spiro[4.5]dodec-8-yl]-1-phenyl-propyl}-amide; |
| 33 | 4,4-Difluoro-cyclohexanecarboxylic acid {(S)-3-[1-benzyl-3-isopropyl-bicyclo[3.2.1]-2,4-dioxo-1β,3,8-triaza-spiro[4.5]dodec-8-yl]-1-phenyl-propyl}-amide; |
| 34 | 4,4-Difluoro-cyclohexanecarboxylic acid {(S)-3-[1-methyl-3-benzyl-bicyclo[3.2.1]-2,4-dioxo-1β,3,8-triaza-spiro[4.5]dodec-8-yl]-1-phenyl-propyl}-amide; |
| 35 | 4,4-Difluoro-cyclohexanecarboxylic acid {(S)-3-[1-ethyl-3-benzyl-bicyclo[3.2.1]-2,4-dioxo-1β,3,8-triaza-spiro[4.5]dodec-8-yl]-1-phenyl-propyl}-amide; |
| 36 | 4,4-Difluoro-cyclohexanecarboxylic acid {(S)-3-[1-propyl-3-benzyl-bicyclo[3.2.1]-2,4-dioxo-1β,3,8-triaza-spiro[4.5]dodec-8-yl]-1-phenyl-propyl}-amide; |
| 37 | 4,4-Difluoro-cyclohexanecarboxylic acid {(S)-3-[1-cyclopropylmethyl-3-benzyl-bicyclo[3.2.1]-2,4-dioxo-1β,3,8-triaza-spiro[4.5]dodec-8-yl]-1-phenyl-propyl}-amide; |
| 38 | 4,4-Difluoro-cyclohexanecarboxylic acid {(S)-3-[1-isopropyl-3-benzyl-bicyclo[3.2.1]-2,4-dioxo-1β,3,8-triaza-spiro[4.5]dodec-8-yl]-1-phenyl-propyl}-amide; |
| 39 | 4,4-Difluoro-cyclohexanecarboxylic acid {(S)-3-[1,3-diethyl-bicyclo[3.2.1]-2-oxo-1β,3,8-triaza-spiro[4.5]dodec-8-yl]-1-phenyl-propyl}-amide; |
| 40 | 4,4-Difluoro-cyclohexanecarboxylic acid {(S)-3-[1-isobutyl-3-methyl-bicyclo[3.2.1]-2-oxo-1β,3,8-triaza-spiro[4.5]dodec-8-yl]-1-phenyl-propyl}-amide; |
| 41 | 4,4-Difluoro-cyclohexanecarboxylic acid {(S)-3-[1-cyclopropylmethyl-3-methyl-bicyclo[3.2.1]-2-oxo-1β,3,8-triaza-spiro[4.5]dodec-8-yl]-1-phenyl-propyl}-amide; |
| 42 | 4,4-Difluoro-cyclohexanecarboxylic acid {(S)-3-[1-(2-methoxyethyl)-3-methyl-bicyclo[3.2.1]-2,4-dioxo-1β,3,8-triaza-spiro[4.5]dodec-8-yl]-1-phenyl-propyl}-amide; |
| 43 | 4,4-Difluoro-cyclohexanecarboxylic acid {(S)-3-[1-isopropyl-3-benzyl-bicyclo[3.2.1]-2-oxo-1β,3,8-triaza-spiro[4.5]dodec-8-yl]-1-phenyl-propyl}-amide; |
| 44 | 4,4-Difluoro-cyclohexanecarboxylic acid {(S)-3-[1-isobutyl-3-benzyl-bicyclo[3.2.1]-2-oxo-1β,3,8-triaza-spiro[4.5]dodec-8-yl]-1-phenyl-propyl}-amide; |
| 45 | 4,4-Difluoro-cyclohexanecarboxylic acid {(S)-3-[1-isopropyl-3-methyl-bicyclo[3.2.1]-2-oxo-1β,3,8-triaza-spiro[4.5]dodec-8-yl]-1-phenyl-propyl}-amide; |
| 46 | 4,4-Difluoro-cyclohexanecarboxylic acid {(S)-3-[1-cyclohexyl-3-methyl-bicyclo[3.2.1]-2,4-dioxo-1β,3,8-triaza-spiro[4.5]dodec-8-yl]-1-phenyl-propyl}-amide; |
| 47 | 4,4-Difluoro-cyclohexanecarboxylic acid {(S)-3-[1-isobutyl-3-ethyl-bicyclo[3.2.1]-2-oxo-1β,3,8-triaza-spiro[4.5]dodec-8-yl]-1-phenyl-propyl}-amide; |
| 48 | 4,4-Difluoro-cyclohexanecarboxylic acid {(S)-3-[3-isobutyl-bicyclo[3.2.1]-2,4-dioxo-1α,3,8-triaza-spiro[4.5]dodec-8-yl]-1-phenyl-propyl}-amide; |
| 49 | 4,4-Difluoro-cyclohexanecarboxylic acid {(S)-3-[1-ethyl-bicyclo[3.2.1]-2,4-dioxo-1β,3,8-triaza-spiro[4.5]dodec-8-yl]-1-phenyl-propyl}-amide; |
| 50 | 4,4-Difluoro-cyclohexanecarboxylic acid {(S)-3-[1-isopropyl-bicyclo[3.2.1]-2,4-dioxo-1β,3,8-triaza-spiro[4.5]dodec-8-yl]-1-phenyl-propyl}-amide; |
| 51 | 4,4-Difluoro-cyclohexanecarboxylic acid {(S)-3-[1-isobutyl-bicyclo[3.2.1]-2,4-dioxo-1β,3,8-triaza-spiro[4.5]dodec-8-yl]-1-phenyl-propyl}-amide; |
| 52 | 4,4-Difluoro-cyclohexanecarboxylic acid {(S)-3-[3-methyl-((S)-2-methyl-butyl)-bicyclo[3.2.1]-2,4-dioxo-1β,3,8-triaza-spiro[4.5]dodec-8-yl]-1-phenyl-propyl}-amide; |
| 53 | 4,4-Difluoro-cyclohexanecarboxylic acid {(S)-3-[3-cyclopropyl-1-isopropyl-bicyclo[3.2.1]-2,4-dioxo-1β,3,8-triaza-spiro[4.5]dodec-8-yl]-1-phenyl-propyl}-amide; |
| 54 | 4,4-Difluoro-cyclohexanecarboxylic acid {(S)-3-[1-isopropyl-3-(2-methoxy-ethyl)-bicyclo[3.2.1]-2,4-dioxo-1β,3,8-triaza-spiro[4.5]dodec-8-yl]-1-phenyl-propyl}-amide; |

| | |
|---|---|
| 55 | 4,4-Difluoro-cyclohexanecarboxylic acid {(S)-3-[3-cyanomethyl-1-isopropyl-bicyclo[3.2.1]-2,4-dioxo-1β,3,8-triaza-spiro[4.5]dodec-8-yl]-1-phenyl-propyl}-amide; |
| 56 | 4,4-Difluoro-cyclohexanecarboxylic acid {(S)-3-[1,3-diisobutyl-bicyclo[3.2.1]-2,4-dioxo-1β,3,8-triaza-spiro[4.5]dodec-8-yl]-1-phenyl-propyl}-amide; |
| 57 | 4,4-Difluoro-cyclohexanecarboxylic acid {(S)-3-[3-cyclopropylmethyl-1-isopropyl-bicyclo[3.2.1]-2,4-dioxo-1β,3,8-triaza-spiro[4.5]dodec-8-yl]-1-phenyl-propyl}-amide; |
| 58 | 4,4-Difluoro-cyclohexanecarboxylic acid {(S)-3-[1-isopropyl-3-phenyl-bicyclo[3.2.1]-2,4-dioxo-1β,3,8-triaza-spiro[4.5]dodec-8-yl]-1-phenyl-propyl}-amide; |
| 59 | 4,4-Difluoro-cyclohexanecarboxylic acid {(S)-3-[1-isopropyl-3-pyridin-3-yl-bicyclo[3.2.1]-2,4-dioxo-1β,3,8-triaza-spiro[4.5]dodec-8-yl]-1-phenyl-propyl}-amide; |
| 60 | 4,4-Difluoro-cyclohexanecarboxylic acid {(S)-3-[1-isopropyl-3-pyridin-4-yl-bicyclo[3.2.1]-2,4-dioxo-1β,3,8-triaza-spiro[4.5]dodec-8-yl]-1-phenyl-propyl}-amide; |
| 61 | 4,4-Difluoro-cyclohexanecarboxylic acid {(S)-3-[1-isopropyl-3-(tetrahydro-furan-3-yl)-bicyclo[3.2.1]-2,4-dioxo-1β,3,8-triaza-spiro[4.5]dodec-8-yl]-1-phenyl-propyl}-amide; |
| 62 | 4,4-Difluoro-cyclohexanecarboxylic acid {(S)-3-[1-isopropyl-3-(tetrahydro-pyran-4-yl)-bicyclo[3.2.1]-2,4-dioxo-1β,3,8-triaza-spiro[4.5]dodec-8-yl]-1-phenyl-propyl}-amide; |
| 63 | 4,4-Difluoro-cyclohexanecarboxylic acid {(S)-3-[3-ethyl-1-isopropyl-bicyclo[3.2.1]-2-oxo-1β,3,8-triaza-spiro[4.5]dodec-8-yl]-1-phenyl-propyl}-amide; |
| 64 | 4,4-Difluoro-cyclohexanecarboxylic acid {(S)-3-[1-cyclopropylmethyl-3-methyl-bicyclo[3.2.1]-2-oxo-1β,3,8-triaza-spiro[4.5]dodec-8-yl]-1-phenyl-propyl}-amide; |
| 65 | 4,4-Difluoro-cyclohexanecarboxylic acid {(S)-3-[3-cyclopropylmethyl-1-isopropyl-bicyclo[3.2.1]-2-oxo-1β,3,8-triaza-spiro[4.5]dodec-8-yl]-1-phenyl-propyl}-amide; |
| 66 | 4,4-Difluoro-cyclohexanecarboxylic acid {(S)-3-[3-(2-hydroxy-ethyl)-1-isopropyl-bicyclo[3.2.1]-2-oxo-1β,3,8-triaza-spiro[4.5]dodec-8-yl]-1-phenyl-propyl}-amide; |
| 67 | 4,4-Difluoro-cyclohexanecarboxylic acid {(S)-3-[1-isopropyl-3-(2-methoxy-ethyl)-bicyclo[3.2.1]-2-oxo-1β,3,8-triaza-spiro[4.5]dodec-8-yl]-1-phenyl-propyl}-amide; |
| 68 | 4,4-Difluoro-cyclohexanecarboxylic acid {(S)-3-[3-(2-ethoxy-ethyl)-1-isopropyl-bicyclo[3.2.1]-2-oxo-1β,3,8-triaza-spiro[4.5]dodec-8-yl]-1-phenyl-propyl}-amide; |
| 69 | 4,4-Difluoro-cyclohexanecarboxylic acid {(S)-3-[1-isobutyl-3-(2-methoxy-ethyl)-bicyclo[3.2.1]-2-oxo-1β,3,8-triaza-spiro[4.5]dodec-8-yl]-1-phenyl-propyl}-amide; |
| 70 | 4,4-Difluoro-cyclohexanecarboxylic acid {(S)-3-[1-isopropyl-3-phenyl-bicyclo[3.2.1]-2-oxo-1β,3,8-triaza-spiro[4.5]dodec-8-yl]-1-phenyl-propyl}-amide; |
| 71 | 4,4-Difluoro-cyclohexanecarboxylic acid {(S)-3-[1-isopropyl-3-(tetrahydro-furan-3-yl)-bicyclo[3.2.1]-2-oxo-1β,3,8-triaza-spiro[4.5]dodec-8-yl]-1-phenyl-propyl}-amide; |
| 72 | 4,4-Difluoro-cyclohexanecarboxylic acid {(S)-3-[1-isopropyl-3-(tetrahydro-pyran-4-yl)-bicyclo[3.2.1]-2-oxo-1β,3,8-triaza-spiro[4.5]dodec-8-yl]-1-phenyl-propyl}-amide; |
| 73 | (S)-1-(3-Fluoro-phenyl)-{3-[1-isopropyl-3-methyl-bicyclo[3.2.1]-2,4-dioxo-1β,3,8-triaza-spiro[4.5]dodec-8-yl]-propyl}-carbamic acid tert-butyl ester; |
| 74 | 8-[(S)-3-Amino-3-(3-fluoro-phenyl)-propyl]-1-isopropyl-3-methyl-bicyclo[3.2.1]-1β,3,8-triaza-spiro[4.5]dodecane-2,4-dione; |
| 75 | {(S)-3-[1-Isopropyl-3-methyl-bicyclo[3.2.1]-2,4-dioxo-1β,3,8-triaza-spiro[4.5]dodec-8-yl]-1-phenyl-propyl}-carbamic acid tert-butyl ester; |
| 76 | 8-[(S)-3-Amino-3-phenyl-propyl]-1-isopropyl-3-methyl-bicyclo[3.2.1]-1β,3,8-triaza-spiro[4.5]dodecane-2,4-dione; |
| 77 | N-(S)-1-(3-Fluoro-phenyl)-{3-[1-isopropyl-3-methyl-bicyclo[3.2.1]-2,4-dioxo-1β,3,8-triaza-spiro[4.5]dodec-8-yl]-propyl}-isobutyramide; |
| 78 | Cyclobutanecarboxylic acid-(S)-1-(3-fluoro-phenyl)-{3-[1-isopropyl-3-methyl-bicyclo[3.2.1]-2,4-dioxo-1β,3,8-triaza-spiro[4.5]dodec-8-yl]-propyl}-amide; |
| 79 | (S)-1-(3-Fluoro-phenyl)-{3-[1-isopropyl-3-methyl-bicyclo[3.2.1]-2,4-dioxo-1β,3,8-triaza-spiro[4.5]dodec-8-yl]-propyl}-acetamide; |
| 80 | 4-Methyl-cyclohexanecarboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide; |
| 81 | Cyclopentanecarboxylic acid-(S)-1-(3-fluoro-phenyl)-{3-[1-isopropyl-3-methyl-bicyclo[3.2.1]-2,4-dioxo-1β,3,8-triaza-spiro[4.5]dodec-8-yl]-propyl}-amide; |
| 82 | Cyclohexanecarboxylic acid-(S)-1-(3-fluoro-phenyl)-{3-[1-isopropyl-3-methyl-bicyclo[3.2.1]-2,4-dioxo-1β,3,8-triaza-spiro[4.5]dodec-8-yl]-propyl}-amide; |
| 83 | 4-Methyl-cyclohexanecarboxylic acid-(S)-1-(3-fluoro-phenyl)-{3-[1-isopropyl-3-methyl-bicyclo[3.2.1]-2,4-dioxo-1β,3,8-triaza-spiro[4.5]dodec-8-yl]-propyl}-amide; |
| 84 | N-{(S)-3-[1-Isopropyl-3-methyl-bicyclo[3.2.1]-2,4-dioxo-1β,3,8-triaza-spiro[4.5]dodec-8-yl]-1-phenyl-propyl}-acetamide; |
| 85 | N-{(S)-3-[1-Isopropyl-3-methyl-bicyclo[3.2.1]-2,4-dioxo-1β,3,8-triaza-spiro[4.5]dodec-8-yl]-1-phenyl-propyl}-isobutyramide; |
| 86 | Cyclobutanecarboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide; |
| 87 | Cyclopentanecarboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide; |
| 88 | Cyclohexanecarboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide; |
| 89 | Cyclopropanecarboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide; |
| 90 | N-{(S)-3-[1-Isopropyl-3-methyl-bicyclo[3.2.1]-2,4-dioxo-1β,3,8-triaza-spiro[4.5]dodec-8-yl]-1-phenyl-propyl}-3,3-dimethyl-butyramide; |
| 91 | 2-Cyclopropyl-N-{(S)-3-[1-isopropyl-3-methyl-bicyclo[3.2.1]-2,4-dioxo-1β,3,8-triaza-spiro[4.5]dodec-8-yl]-1-phenyl-propyl}-acetamide; |
| 92 | Tetrahydro-pyran-4-carboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide; |
| 93 | N-{(S)-3-[1-Isopropyl-3-methyl-bicyclo[3.2.1]-2,4-dioxo-1β,3,8-triaza-spiro[4.5]dodec-8-yl]-1-phenyl-propyl}-2,2-dimethyl-propionamide; |
| 94 | (S)-1-Acetyl-piperidine-3-carboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide; |
| 95 | Tetrahydro-pyran-3-carboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide; |
| 96 | 4-Methoxy-cyclohexanecarboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide; |
| 97 | 4-Trifluoromethyl-cyclohexanecarboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide; |
| 98 | 4,4-Difluoro-cyclohexanecarboxylic acid {(S)-3-[1-isopropyl-3-(2-methoxy-propyl)-bicyclo[3.2.1]-2,4-dioxo-1β,3,8-triaza-spiro[4.5]dodec-8-yl]-1-phenyl-propyl}-amide; |
| 99 | 4,4-Difluoro-cyclohexanecarboxylic acid {(S)-3-[1-isopropyl-3-(2-methoxy-propyl)-bicyclo[3.2.1]-2-oxo-1β,3,8-triaza-spiro[4.5]dodec-8-yl]-1-phenyl-propyl}-amide; |
| 100 | 4,4-Difluoro-cyclohexanecarboxylic acid {(S)-3-[1-isopropyl-3-oxetan-2-ylmethyl-bicyclo[3.2.1]-2,4-dioxo-1β,3,8-triaza-spiro[4.5]dodec-8-yl]-1-phenyl-propyl}-amide; |
| 101 | 4,4-Difluoro-cyclohexanecarboxylic acid {(S)-3-[1-isopropyl-3-oxetan-2-ylmethyl-bicyclo[3.2.1]-2-oxo-1β,3,8-triaza-spiro[4.5]dodec-8-yl]-1-phenyl-propyl}-amide; |
| 102 | 4,4-Difluoro-cyclohexanecarboxylic acid {(S)-3-[1-isopropyl-3-oxetan-3-ylmethyl-bicyclo[3.2.1]-2,4-dioxo-1β,3,8-triaza-spiro[4.5]dodec-8-yl]-1-phenyl-propyl}-amide; |
| 103 | 4,4-Difluoro-cyclohexanecarboxylic acid {(S)-3-[1-isopropyl-3-oxetan-3-ylmethyl-bicyclo[3.2.1]-2-oxo-1β,3,8-triaza-spiro[4.5]dodec-8-yl]-1-phenyl-propyl}-amide; |
| 104 | 4,4-Difluoro-cyclohexanecarboxylic acid {(S)-3-[1-isopropyl-3-(tetrahydro-furan-2-ylmethyl)-bicyclo[3.2.1]-2,4-dioxo-1β,3,8-triaza-spiro[4.5]dodec-8-yl]-1-phenyl-propyl}-amide; |
| 105 | 4,4-Difluoro-cyclohexanecarboxylic acid {(S)-3-[1-isopropyl-3-(tetrahydro-furan-2-ylmethyl)-bicyclo[3.2.1]-2-oxo-1β,3,8-triaza-spiro[4.5]dodec-8-yl]-1-phenyl-propyl}-amide; |

-continued

| 106 | 4,4-Difluoro-cyclohexanecarboxylic acid {(S)-3-[1-isopropyl-3-(tetrahydro-furan-3-ylmethyl)-bicyclo[3.2.1]-2,4-dioxo-1β,3,8-triaza-spiro[4.5]dodec-8-yl]-1-phenyl-propyl}-amide; |
| --- | --- |
| 107 | 4,4-Difluoro-cyclohexanecarboxylic acid {(S)-3-[1-isopropyl-3-(tetrahydro-furan-3-ylmethyl)-bicyclo[3.2.1]-2-oxo-1β,3,8-triaza-spiro[4.5]dodec-8-yl]-1-phenyl-propyl}-amide; |
| 108 | 4,4-Difluoro-cyclohexanecarboxylic acid {(S)-3-[1-isopropyl-3-(tetrahydro-pyran-2-ylmethyl)-bicyclo[3.2.1]-2,4-dioxo-1β,3,8-triaza-spiro[4.5]dodec-8-yl]-1-phenyl-propyl}-amide; |
| 109 | 4,4-Difluoro-cyclohexanecarboxylic acid {(S)-3-[1-isopropyl-3-(tetrahydro-pyran-2-ylmethyl)-bicyclo[3.2.1]-2-oxo-1β,3,8-triaza-spiro[4.5]dodec-8-yl]-1-phenyl-propyl}-amide; |
| 110 | 4,4-Difluoro-cyclohexanecarboxylic acid {(S)-3-[1-isopropyl-3-(tetrahydro-pyran-3-ylmethyl)-bicyclo[3.2.1]-2,4-dioxo-1β,3,8-triaza-spiro[4.5]dodec-8-yl]-1-phenyl-propyl}-amide; |
| 111 | 4,4-Difluoro-cyclohexanecarboxylic acid {(S)-3-[1-isopropyl-3-(tetrahydro-pyran-3-ylmethyl)-bicyclo[3.2.1]-2-oxo-1β,3,8-triaza-spiro[4.5]dodec-8-yl]-1-phenyl-propyl}-amide; |
| 112 | 4,4-Difluoro-cyclohexanecarboxylic acid {(S)-3-[1-isopropyl-3-(tetrahydro-pyran-4-ylmethyl)-bicyclo[3.2.1]-2,4-dioxo-1β,3,8-triaza-spiro[4.5]dodec-8-yl]-1-phenyl-propyl}-amide; |
| 113 | 4,4-Difluoro-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide; | and pharmaceutically acceptable salts thereof.

36. A compound according to claim 35, wherein said compound is selected from:
- 4,4-Difluoro-cyclohexanecarboxylic acid {(S)-3-[3-cyclopropylmethyl-1-isopropyl-bicyclo[3.2.1]-2-oxo-1β,3,8-triaza-spiro[4.5]dodec-8-yl]-1-phenyl-propyl}-amide;
- 4,4-Difluoro-cyclohexanecarboxylic acid {(S)-3-[1-isopropyl-3-(2-methoxy-propyl)-bicyclo[3.2.1]-2-oxo-1β,3,8-triaza-spiro[4.5]dodec-8-yl]-1-phenyl-propyl}-amide;
- 4,4-Difluoro-cyclohexanecarboxylic acid {(S)-3-[1-isopropyl-3-(tetrahydro-furan-3-ylmethyl)-bicyclo[3.2.1]-2-oxo-1β,3,8-triaza-spiro[4.5]dodec-8-yl]-1-phenyl-propyl}-amide;
- 4,4-Difluoro-cyclohexanecarboxylic acid {(S)-3-[1-isopropyl-3-(tetrahydro-pyran-2-ylmethyl)-bicyclo[3.2.1]-2-oxo-1β,3,8-triaza-spiro[4.5]dodec-8-yl]-1-phenyl-propyl}-amide;
- 4,4-Difluoro-cyclohexanecarboxylic acid {(S)-3-[1-isopropyl-3-(tetrahydro-pyran-3-ylmethyl)-bicyclo[3.2.1]-2-oxo-1β,3,8-triaza-spiro[4.5]dodec-8-yl]-1-phenyl-propyl}-amide;

and pharmaceutically acceptable salts thereof.

37. A compound according to claim 35, wherein said compound is selected from:
- 4,4-Difluoro-cyclohexanecarboxylic acid {(S)-3-[1-ethyl-3-(4-methanesulfonyl-benzyl)-bicyclo[3.2.1]-2,4-dioxo-1β,3,8-triaza-spiro[4.5]dodec-8-yl]-1-phenyl-propyl}-amide;
- 4,4-Difluoro-cyclohexanecarboxylic acid {(S)-3-[1-isobutyl-3-methyl-bicyclo[3.2.1]-2,4-dioxo-1β,3,8-triaza-spiro[4.5]dodec-8-yl]-1-phenyl-propyl}-amide;
- 4,4-Difluoro-cyclohexanecarboxylic acid {(S)-3-[1-ethyl-3-benzyl-bicyclo[3.2.1]-2,4-dioxo-1β,3,8-triaza-spiro[4.5]dodec-8-yl]-1-phenyl-propyl}-amide;
- 4,4-Difluoro-cyclohexanecarboxylic acid {(S)-3-[1-isopropyl-3-benzyl-bicyclo[3.2.1]-2,4-dioxo-1β,3,8-triaza-spiro[4.5]dodec-8-yl]-1-phenyl-propyl}-amide;
- 4,4-Difluoro-cyclohexanecarboxylic acid {(S)-3-[1-isobutyl-3-methyl-bicyclo[3.2.1]-2-oxo-1β,3,8-triaza-spiro[4.5]dodec-8-yl]-1-phenyl-propyl}-amide;
- 4,4-Difluoro-cyclohexanecarboxylic acid {(S)-3-[1-isopropyl-3-benzyl-bicyclo[3.2.1]-2-oxo-1β,3,8-triaza-spiro[4.5]dodec-8-yl]-1-phenyl-propyl}-amide;
- 4,4-Difluoro-cyclohexanecarboxylic acid {(S)-3-[1-isobutyl-3-benzyl-bicyclo[3.2.1]-2-oxo-1β,3,8-triaza-spiro[4.5]dodec-8-yl]-1-phenyl-propyl}-amide;
- 4,4-Difluoro-cyclohexanecarboxylic acid {(S)-3-[1-isobutyl-3-ethyl-bicyclo[3.2.1]-2-oxo-1β,3,8-triaza-spiro[4.5]dodec-8-yl]-1-phenyl-propyl}-amide;
- 4,4-Difluoro-cyclohexanecarboxylic acid {(S)-3-[3-methyl-1((S)-2-methyl-butyl)-bicyclo[3.2.1]-2,4-dioxo-1β,3,8-triaza-spiro[4.5]dodec-8-yl]-1-phenyl-propyl}-amide;
- 4,4-Difluoro-cyclohexanecarboxylic acid {(S)-3-[3-cyclopropyl-1-isopropyl-bicyclo[3.2.1]-2,4-dioxo-1β,3,8-triaza-spiro[4.5]dodec-8-yl]-1-phenyl-propyl}-amide;
- 4,4-Difluoro-cyclohexanecarboxylic acid {(S)-3-[1-isopropyl-3-(2-methoxy-ethyl)-bicyclo[3.2.1]-2,4-dioxo-1β,3,8-triaza-spiro[4.5]dodec-8-yl]-1-phenyl-propyl}-amide;
- 4,4-Difluoro-cyclohexanecarboxylic acid {(S)-3-[1,3-diisobutyl-bicyclo[3.2.1]-2,4-dioxo-1β,3,8-triaza-spiro[4.5]dodec-8-yl]-1-phenyl-propyl}-amide;
- 4,4-Difluoro-cyclohexanecarboxylic acid {(S)-3-[1-isopropyl-3-phenyl-bicyclo[3.2.1]-2-oxo-1β,3,8-triaza-spiro[4.5]dodec-8-yll-1-phenyl-propyl}-amide;
- Cyclopentanecarboxylic acid-(S)-1-(3-fluoro-phenyl)-{3-[1-isopropyl-3-methyl-bicyclo[3.2.1]-2,4-dioxo-1β,3,8-triaza-spiro[4.5]dodec-8-yl]-propyl}-amide;
- Cyclohexanecarboxylic acid-(S)-1-(3-fluoro-phenyl)-{3-[1-isopropyl-3-methyl-bicyclo[3.2.1]-2,4-dioxo-1β,3,8-triaza-spiro[4.5]dodec-8-yl]-propyl}-amide;
- 4,4-Difluoro-cyclohexanecarboxylic acid {(S)-3-[1-isopropyl-3-(2-methoxy-propyl)-bicyclo[3.2.1]-2,4-dioxo-1β,3,8-triaza-spiro[4.5]dodec-8-yll-1-phenyl-propyl}-amide;
- 4,4-Difluoro-cyclohexanecarboxylic acid {(S)-3-[1-isopropyl-3-(tetrahydro-furan-2-ylmethyl)-bicyclo[3.2.1]-2,4-dioxo-1β,3,8-triaza-spiro[4.5]dodec-8-yl]-1-phenyl-propyl}-amide;
- 4,4-Difluoro-cyclohexanecarboxylic acid {(S)-3-[1-isopropyl-3-(tetrahydro-furan-2-ylmethyl)-bicyclo[3.2.1]-2-oxo-1β,3,8-triaza-spiro[4.5]dodec-8-yl]-1-phenyl-propyl}-amide;
- 4,4-Difluoro-cyclohexanecarboxylic acid {(S)-3-[1-isopropyl-3-(tetrahydro-furan-3-ylmethyl)-bicyclo[3.2.1]-2,4-dioxo-1β,3,8-triaza-spiro[4.5]dodec-8-yl]-1-phenyl-propyl}-amide;
- 4,4-Difluoro-cyclohexanecarboxylic acid {(S)-3-[1-isopropyl-3-(tetrahydro-pyran-2-ylmethyl)-bicyclo[3.2.1]-2,4-dioxo-1β,3,8-triaza-spiro[4.5]dodec-8-yl]-1-phenyl-propyl}-amide;
- 4,4-Difluoro-cyclohexanecarboxylic acid {(S)-3-[1-isopropyl-3-(tetrahydro-pyran-4-ylmethyl)-bicyclo[3.2.1]-2,4-dioxo-1β,3,8-triaza-spiro[4.5]dodec-8-yl]-1-phenyl-propyl}-amide;
- 4,4-Difluoro-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

and pharmaceutically acceptable salts thereof.

38. A compound according to claim 35, wherein said compound is selected from:

4,4-Difluoro-cyclohexanecarboxylic acid {(S)-3-[3-(4-methanesulfonyl-benzyl)-bicyclo[3.2.1]-2,4-dioxo-1β,3,8-triaza-spiro[4.5]dodec-8-yl]-1-phenyl-propyl}-amide;

4,4-Difluoro-cyclohexanecarboxylic acid {(S)-3-[1,3-diethyl-bicyclo[3.2.1]-2,4-dioxo-1α,3,8-triaza-spiro[4.5]dodec-8-yl]-1-phenyl-propyl}-amide;

4,4-Difluoro-cyclohexanecarboxylic acid {(S)-3-[1,3-diethyl-bicyclo[3.2.1]-2,4-dioxo-1β,3,8-triaza-spiro[4.5]dodec-8-yl]-1-phenyl-propyl}-amide;

4,4-Difluoro-cyclohexanecarboxylic acid {(S)-3-[3-(4-dimethylsulfamoyl-benzyl)-bicyclo[3.2.1]-2,4-dioxo-1α,3,8-triaza-spiro[4.5]dodec-8-yl]-1-phenyl-propyl}-amide;

4,4-Difluoro-cyclohexanecarboxylic acid {(S)-3-[1-ethyl-3-methyl-bicyclo[3.2.1]-2,4-dioxo-1β,3,8-triaza-spiro[4.5]dodec-8-yl]-1-phenyl-propyl}-amide;

4,4-Difluoro-cyclohexanecarboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide;

4,4-Difluoro-cyclohexanecarboxylic acid {(S)-3-[1-propyl-3-methyl-bicyclo[3.2.1]-2,4-dioxo-1β,3,8-triaza-spiro[4.5]dodec-8-yl]-1-phenyl-propyl}-amide;

4,4-Difluoro-cyclohexanecarboxylic acid {(S)-3-[1-cyclopropylmethyl-3-methyl-bicyclo[3.2.1]-2,4-dioxo-1β,3,8-triaza-spiro[4.5]dodec-8-yl]-1-phenyl-propyl}-amide;

4,4-Difluoro-cyclohexanecarboxylic acid {(S)-3-[3-ethyl-1-isopropyl-bicyclo[3.2.1]-2,4-dioxo-1β,3,8-triaza-spiro[4.5]dodec-8-yl]-1-phenyl-propyl}-amide;

4,4-Difluoro-cyclohexanecarboxylic acid {(S)-3-[3-ethyl-1-isobutyl-bicyclo[3.2.1]-2,4-dioxo-1β,3,8-triaza-spiro[4.5]dodec-8-yl]-1-phenyl-propyl}-amide;

4,4-Difluoro-cyclohexanecarboxylic acid {(S)-3-[1-cyclopropylmethyl-3-ethyl-bicyclo[3.2.1]-2,4-dioxo-1β,3,8-triaza-spiro[4.5]dodec-8-yl]-1-phenyl-propyl}-amide;

4,4-Difluoro-cyclohexanecarboxylic acid {(S)-3-[1,3-diisopropyl-bicyclo[3.2.1]-2,4-dioxo-1β,3,8-triaza-spiro[4.5]dodec-8-yl]-1-phenyl-propyl}-amide;

4,4-Difluoro-cyclohexanecarboxylic acid {(S)-3-[1-isobutyl-3-isopropyl-bicyclo[3.2.1]-2,4-dioxo-1β,3,8-triaza-spiro[4.5]dodec-8-yl]-1-phenyl-propyl}-amide;

4,4-Difluoro-cyclohexanecarboxylic acid {(S)-3-[1-methyl-3-benzyl-bicyclo[3.2.1]-2,4-dioxo-1β,3,8-triaza-spiro[4.5]dodec-8-yl]-1-phenyl-propyl}-amide;

4,4-Difluoro-cyclohexanecarboxylic acid {(S)-3-[1-propyl-3-benzyl-bicyclo[3.2.1]-2,4-dioxo-1β,3,8-triaza-spiro[4.5]dodec-8-yl]-1-phenyl-propyl}-amide;

4,4-Difluoro-cyclohexanecarboxylic acid {(S)-3-[1-cyclopropylmethyl-3-benzyl-bicyclo[3.2.1]-2,4-dioxo-1β,3,8-triaza-spiro[4.5]dodec-8-yl]-1-phenyl-propyl}-amide;

4,4-Difluoro-cyclohexanecarboxylic acid {(S)-3-[1,3-diethyl-bicyclo[3.2.1]-2-oxo-1β,3,8-triaza-spiro[4.5]dodec-8-yl]-1-phenyl-propyl}-amide;

4,4-Difluoro-cyclohexanecarboxylic acid {(S)-3-[1-cyclopropylmethyl-3-methyl-bicyclo[3.2.1]-2-oxo-1β,3,8-triaza-spiro[4.5]dodec-8-yl]-1-phenyl-propyl}-amide;

4,4-Difluoro-cyclohexanecarboxylic acid {(S)-3-[1-isopropyl-3-methyl-bicyclo[3.2.1]-2-oxo-1β,3,8-triaza-spiro[4.5]dodec-8-yl]-1-phenyl-propyl}-amide;

4,4-Difluoro-cyclohexanecarboxylic acid {(S)-3-[1-cyclohexyl-3-methyl-bicyclo[3.2.1]-2,4-dioxo-1β,3,8-triaza-spiro[4.5]dodec-8-yl]-1-phenyl-propyl}-amide;

4,4-Difluoro-cyclohexanecarboxylic acid {(S)-3-[3-isobutyl-bicyclo[3.2.1[-2,4-dioxo-1α,3,8-triaza-spiro[4.5]dodec-8-yl]-1-phenyl-propyl}-amide;

4,4-Difluoro-cyclohexanecarboxylic acid {(S)-3-[1-isopropyl-bicyclo[3.2.1]-2,4-dioxo-1β,3,8-triaza-spiro[4.5]dodec-8-yl]-1-phenyl-propyl}-amide;

4,4-Difluoro-cyclohexanecarboxylic acid {(S)-3-[3-cyanomethyl-1-isopropyl-bicyclo[3.2.1]-2,4-dioxo-1β,3,8-triaza-spiro[4.5]dodec-8-yl]-1-phenyl-propyl}-amide;

4,4-Difluoro-cyclohexanecarboxylic acid {(S)-3-[3-cyclopropylmethyl-1-isopropyl-bicyclo[3.2.1]-2,4-dioxo-1β,3,8-triaza-spiro[4.5]dodec-8-yl]-1-phenyl-propyl}-amide;

4,4-Difluoro-cyclohexanecarboxylic acid {(S)-3-[1-isopropyl-3-phenyl-bicyclo[3.2.1]-2,4-dioxo-1β,3,8-triaza-spiro[4.5]dodec-8-yl]-1-phenyl-propyl}-amide;

4,4-Difluoro-cyclohexanecarboxylic acid {(S)-3-[3-ethyl-1-isopropyl-bicyclo[3.2.1]-2-oxo-1β,3,8-triaza-spiro[4.5]dodec-8-yl]-1-phenyl-propyl}-amide;

4,4-Difluoro-cyclohexanecarboxylic acid {(S)-3-[1-cyclopropylmethyl-3-methyl-bicyclo[3.2.1]-2-oxo-1β,3,8-triaza-spiro[4.5]dodec-8-yl]-1-phenyl-propyl}-amide;

4,4-Difluoro-cyclohexanecarboxylic acid {(S)-3-[3-(2-hydroxy-ethyl)-1-isopropyl-bicyclo[3.2.1]-2-oxo-1β,3,8-triaza-spiro[4.5]dodec-8-yl]-1-phenyl-propyl}-amide;

4,4-Difluoro-cyclohexanecarboxylic acid {(S)-3-[1-isopropyl-3-(2-methoxy-ethyl)-bicyclo[3.2.1]-2-oxo-1β,3,8-triaza-spiro[4.5]dodec-8-yl]-1-phenyl-propyl}-amide;

4,4-Difluoro-cyclohexanecarboxylic acid {(S)-3-[3-(2-ethoxy-ethyl)-1-isopropyl-bicyclo[3.2.1]-2-oxo-1β,3,8-triaza-spiro[4.5]dodec-8-yl]-1-phenyl-propyl}-amide;

4,4-Difluoro-cyclohexanecarboxylic acid {(S)-3-[1-isobutyl-3-(2-methoxy-ethyl)-bicyclo[3.2.1]-2-oxo-1β,3,8-triaza-spiro[4.5]dodec-8-yl]-1-phenyl-propyl}-amide;

4,4-Difluoro-cyclohexanecarboxylic acid {(S)-3-[1-isopropyl-3-(tetrahydro-furan-3-yl)-bicyclo[3.2.1]-2-oxo-1β,3,8-triaza-spiro[4.5]dodec-8-yl]-1-phenyl-propyl}-amide;

4,4-Difluoro-cyclohexanecarboxylic acid {(S)-3-[1-isopropyl-3-(tetrahydro-pyran-4-yl)-bicyclo[3.2.1-2-oxo-1β,3,8-triaza-spiro[4.5]dodec-8-yl]-1-phenyl-propyl}-amide;

N-(S)-1-(3-Fluoro-phenyl)-{3-[1-isopropyl-3-methyl-bicyclo[3.2.1]-2,4-dioxo-1β,3,8-triaza-spiro[4.5]dodec-8-yll-propyl}-isobutyramide;

Cyclobutanecarboxylic acid-(S)-1-(3-fluoro-phenyl)-{3-[1-isopropyl-3-methyl-bicyclo[3.2.1]-2,4-dioxo-1β,3,8-triaza-spiro[4.5]dodec-8-yl]-propyl}-amide;

(S)-1-(3-Fluoro-phenyl)-{3-[1-isopropyl-3-methyl-bicyclo[3.2.1]-2,4-dioxo-1β,3,8-triaza-spiro[4.5]dodec-8-yl]-propyl}-acetamide;

4-Methyl-cyclohexanecarboxylic acid {(S)-3-[1-isopropyl-3-methyl-bicyclo[3.2.1]-2,4-dioxo-1β,3,8-triaza-spiro[4.5]dodec-8-yl1-1-phenyl-propyl}-amide;

Cyclohexanecarboxylic acid-(S)-1-(3-fluoro-phenyl)-{3-[1-isopropyl-3-methyl-bicyclo[3.2.1]-2,4-dioxo-1β,3,8-triaza-spiro[4.5]dodec-8-yl]-propyl}-amide;

4-Methyl-cyclohexanecarboxylic acid-(S)-1-(3-fluoro-phenyl)-{3-[1-isopropyl-3-methyl-bicyclo[3.2.1]-2,4-dioxo-1β,3,8-triaza-spiro[4.5]dodec-8-yl]-propyl}-amide;

N-{(S)-3-[1-Isopropyl-3-methyl-bicyclo[3.2.1-2,4-dioxo-1β,3,8-triaza-spiro[4.5]dodec-8-yl]-1-phenyl-propyl}-isobutyramide;

Cyclobutanecarboxylic acid {(S)-3-[1-is opropyl-3-methyl-bicyclo[3.2.1]-2,4-dioxo-1β,3,8-triaza-spiro[4.5]dodec-8-yl]-1-phenyl-propyl}-amide;

Cyclopentanecarboxylic acid {(S)-3-[1-isopropyl-3-methyl-bicyclo[3.2.1]-2,4-dioxo-1β,3,8-triaza-spiro[4.5]dodec-8-yl]-1-phenyl-propyl}-amide;

Cyclohexanecarboxylic acid {(S)-3-[1-is opropyl-3-methyl-bicyclo[3.2.1]-2,4-dioxo-1β,3,8-triaza-spiro[4.5]dodec-8-yl]-1-phenyl-propyl}-amide;

and pharmaceutically acceptable salts thereof.

* * * * *

UNITED STATES PATENT AND TRADEMARK OFFICE
CERTIFICATE OF CORRECTION

| | |
|---|---|
| PATENT NO. | : 7,960,403 B2 |
| APPLICATION NO. | : 11/792581 |
| DATED | : June 14, 2011 |
| INVENTOR(S) | : Chan Chun Kong et al. |

It is certified that error appears in the above-identified patent and that said Letters Patent is hereby corrected as shown below:

IN THE CLAIMS:

Column 111, Claim 19, line 2 reads "$R_4$ or $R_5$ are independently phenyl or benzyl which are" should read -- $R_4$ or $R_5$ is phenyl or benzyl which in each case is --

Signed and Sealed this
Fifteenth Day of January, 2013

David J. Kappos
*Director of the United States Patent and Trademark Office*